United States Patent
Sundermann et al.

(10) Patent No.: US 7,276,518 B2
(45) Date of Patent: Oct. 2, 2007

(54) SUBSTITUTED CYCLOHEXANE-1,4-DIAMINE COMPOUNDS

(75) Inventors: Bernd Sundermann, Aachen (DE); Hagen-Heinrich Hennies, Simmerath (DE); Werner Englberger, Stolberg (DE); Babette-Yvonne Koegel, Langerwehe-Hamaich (DE)

(73) Assignee: Gruenenthal GmbH, Aachen (DE)

( * ) Notice: Subject to any disclaimer, the term of this patent is extended or adjusted under 35 U.S.C. 154(b) by 202 days.

(21) Appl. No.: 10/704,329

(22) Filed: Nov. 10, 2003

(65) Prior Publication Data

US 2004/0162287 A1 Aug. 19, 2004

(30) Foreign Application Priority Data

May 9, 2001 (DE) ................................ 101 23 163

(51) Int. Cl.
*C07D 471/12* (2006.01)
*C07D 209/14* (2006.01)
*C07C 211/49* (2006.01)
*A61K 31/404* (2006.01)
*A61K 31/136* (2006.01)

(52) U.S. Cl. ...................... 514/301; 514/359; 514/367; 514/416; 514/438; 514/443; 514/466; 514/649; 546/114; 548/152; 548/257; 548/506; 549/49; 549/74; 549/434; 564/306

(58) Field of Classification Search ...................... None
See application file for complete search history.

(56) References Cited

U.S. PATENT DOCUMENTS

| | | | |
|---|---|---|---|
| 4,113,866 A * | 9/1978 | Lednicer ................ | 514/239.5 |
| 4,447,454 A * | 5/1984 | Lednicer ................ | 514/647 |
| 5,153,226 A | 10/1992 | Chucholowski et al. | |
| 5,200,408 A | 4/1993 | Bru-Magniez et al. | |
| 5,565,568 A | 10/1996 | Cho et al. | |
| 5,773,441 A | 6/1998 | Hipskind et al. | |
| 6,194,437 B1 | 2/2001 | Horwell et al. | |
| 6,307,017 B1 | 10/2001 | Coy et al. | |
| 6,849,622 B2 * | 2/2005 | Yasuda et al. ......... | 514/217.08 |
| 7,138,397 B2 * | 11/2006 | Yasuda et al. ......... | 514/254.01 |
| 2002/0028799 A1 | 3/2002 | Naylor et al. | |
| 2002/0055759 A1 | 5/2002 | Shibuya | |
| 2002/0169101 A1 | 11/2002 | Gonzalez et al. | |
| 2002/0177689 A1 | 11/2002 | Benson et al. | |
| 2003/0119714 A1 | 6/2003 | Naylor et al. | |
| 2004/0023862 A1 | 2/2004 | Smart et al. | |
| 2004/0087561 A1 | 5/2004 | Gonzalez et al. | |
| 2004/0110768 A1 | 6/2004 | Higginbottom et al. | |
| 2004/0116440 A1 | 6/2004 | Higginbottom et al. | |

FOREIGN PATENT DOCUMENTS

| | | |
|---|---|---|
| EP | 0 380 063 A1 | 3/1990 |
| EP | 0 415 413 A1 | 3/1991 |
| WO | WO95/00542 A1 | 1/1995 |
| WO | WO96/31214 A1 | 10/1996 |
| WO | WO97/06803 A1 | 2/1997 |
| WO | WO98/07718 A1 | 2/1998 |
| WO | WO 01/68120 A2 | 9/2001 |
| WO | WO 02/30890 * | 4/2002 |
| WO | WO 02/30891 * | 4/2002 |
| WO | WO 02/40008 A2 | 5/2002 |
| WO | WO 02/40022 A1 | 5/2002 |
| WO | WO 02/40069 A2 | 5/2002 |
| WO | WO 02/40468 A1 | 5/2002 |
| WO | WO 02/40469 A1 | 5/2002 |
| WO | WO 02/40475 A1 | 5/2002 |

OTHER PUBLICATIONS

Crawford et al, "Steroid Injection for Heel Pain: Evidence of Short-Term Effectiveness. A Randomized Controlled Trial," Rheumatology, vol. 38, p. 974-977 (1999).*

Richard J. Lewis, Sr., Hawley's Condensed Chemical Dictionary (14th Ed.) (2001).*

Lednicer, STN International, HCAPLUS Database, Columbus, OH, Accession No. 1979:86991, Reg. Nos. 68967-88-4 and 68967-89-5.*

James M. Wu, et al., "Discovery of High Affinity Bombesin Receptor Subtype 3 Agonists", Molecular Pharmacology, (1996) pp. 1355-1363, vol. 50, The American Society for Pharmacology and Experimental Therapeutics.

Kazuyuki Yamada, et al., "Hyperrsponsiveness to Platable and Aversive Taste Stimuli in Genetically Obese (Bonbesin Receptor Subtype-3-Deficient) Mice", Physiology & behavior, (1999), pp. 863-867, vol. 66, No. 5, the Elsevier Science Inc., PII S0031-9384(99)00032-3.

Zahra Fathi, et al., "BRS-3: A Novel Bombesin Receptor Subtype Selectively Expressed in Testis and Lung Carcinoma Cells", The Journal of Biological Chemistry, (1993), pp. 5979-5984, vol. 268, No. 8.

Valentin Gorbulev, et al., "Molecular Cloning of a New Bombesin Receptor Subtype Expressed in Uterus During Pregnancy", Eur. J. Biochem., (1992), pp. 405-410, vol. 208.

Antonello Mai, et al., "5-Alkyl-2-(Alkylthlo)-6-(2,6-Dihalophenylmethyl)-3,4-Dihydropyrimidin-4(3H)-C Novel Potent and Selective Dihydro-Alkoxy-Benzyl-Oxoprimdine Derivative", J. Med. Chem., (1999), pp. 619-627, vol. 42, The American Chemical Society.

Christopher J. Moody, et al., "Diels-Alder Reactively of Pyrano [4,3-b]Indol-3-Ones, Indole 2,3-Quinodimethane Analogues", J. Chem. Soc. Perkin Trans., (1990), pp. 673-679.

Dirk Webber, et al., "Systematic Optimization of a Lead-Structure Identities for a Selective Short Peptide Agonist for the Human Orphan Receptor BRS-3", Journal of Peptide Science, (2002), pp. 461-475, vol. 8, Wiley Interscience.

(Continued)

*Primary Examiner*—Rebecca Anderson
*Assistant Examiner*—Andrew B. Freistein
(74) *Attorney, Agent, or Firm*—Crowell & Moring LLP

(57) ABSTRACT

Substituted cyclohexane-1,4-diamine compounds, methods for production thereof, pharmaceutical compositions comprising these compounds and methods of treatment using these compounds.

62 Claims, No Drawings

OTHER PUBLICATIONS

Samuel A. Mantey, et al., "Discovery of a High Affinity Radioligand for the Human Orphan Receptor, Bombesin Receptor Subtype 3, Which Demonstrates that it has a Unique Pharmacology Compared with the Other Mammalian Bombesin Receptors", The Journal of Biological Chemistry, (1997), pp. 26062-26071, vol. 272, No. 41.

Tapas K. Pradhan, et al., "Identification of a Unique Ligand Which had High Affinity for all Four Bombesin Receptor Subtypes", European Journal of Pharmacology, (1998), pp. 275-287, vol. 343.

K Yamada, et al., "Role of Bombesin (BN)-Like Peptides/Receptors in Emotional Behavior by Comparison of Three Strains of BN-Like Peptide Receptor knockout Mice", Molecular Psychiatry, (2002), pp. 113-117, vol. 7, Nature Publishing Group.

A. Floersheimer, et al., "Solid-Phase Synthesis of Peptides with the Highly Acid-Sensitive HMPB Linker", Peptides, (1990), pp. 131-132, ESCOM Science Publishers B.V.

Kazuyuki Yamada, et al., "Differential Effects of Social Isolation Upon Body Weight, Food Consumption, and Responsiveness to Novel and Social Environment in Bombesin Receptor Subtype-3 (BRS-3) Dedicient Mice", Physiology & Behavior, (2000), pp. 555-561, vol. 68.

Dirk Weber, et al., "Design of Selective Peptidomimetic Agonists for the Human Orphan Receptor BRS-3", Journal of Medicinal Chemistry, (2003), pp. 1919-1930, vol. 46, No. 10, The American Chemical Society.

Baodong Sun, et al., "Presence of Receptors for Bombesin/Gastrin-Releasing Peptide and mRNA for Three Receptor Subtypes in Human Prostate Cancers", The Prostate, (2000), pp. 295-303, vol. 42, Wiley-Liss Inc.

Hiroko Ohki-Hamzaki, et al., "Mice lacking Bombesin Receptor Subtype-3 Develop Metalbolic Defects and Obesity", Letters to Nature, (Nov. 1997), pp. 165-169, vol. 390.

Samuel A. Mantey, et al., Rational Design of a Peptide Agonist That Interacts Selectively with the Orphan Receptor, Bombesin Receptor Subtyoe 3*:, Selective BRS-3 Ligand, (2000), pp. 9219-9228).

Achim Fleischmann, et al., "Bombesin Receptors in Distant Tissue Compartments of Human Pancreatic Diseases", Laboratory Investigation, (2000), pp. 1807-1817, vol. 80, No. 12, The United States and Canadian Academy of Pathology, Inc.

Barber Doerner, et al., "Preparation of Carboxy-Modified Peptide Fragments Using Alkyoxybenzaldehyde Resins", Peptides, (1998), pp. 90-91.

Valetin Gorbulev, et al., "Organization and Chromosomal Localization of the Gene for the Human Bombesin Receptor Subtype Expressed in Pregnant Uterus", FEBS Letters, (1994), pp. 260-264, vol. 340, Federation of European Biochemical Societies.

Baodong Sun, et al., "The Presence of Receptors for Bombesin/GRP and mRNA for Three Receptor Subtypes in Human Ovarian Epithellal Cancers", Regulatory Peptides, (2000), pp. 77-84, vol. 90, Elsevier Science B.V.

Ali Ardati, et al., "Interaction of [$^3$H] Orphanin FQ and $^{125}$I-Tyr14-Orphanin FQ with the Orphanin FQ Receptor: Kinetics and Modulation by Cations and Guanine Nucleotides", Molecular Pharmacy, (1997), pp. 816-824, vol. 51, The American Society for Pharmacology and Experimental Therapeutics (1997), pp. 816-824, vol. 51, The American Society for Pharmacology and Experimental Therapeutics.

Fuad A. Abdulla, et al., "Axotomy Reduces the Effect of Analgesic Opioids yet Increases the Effect of Nociceptin on Dorsal Root Ganglion Neurons", The Journal of Neuroscience, (Dec. 1, 1998), pp. 9685-9694, vol. 18.

Girolamo Calo, et al., "Pharmacology of Nociceptin and its Receptor: A Novel Therapeutic Target", British Journal of Pharmacology, (2000), pp. 1261-1283, vol. 129, Mcmillan Publishers Ltd.

Hunter C. Champion, et al., "[Tyr$^1$]-Nociceptin, a Novel Nociceptin Analog, Decreases Systemic Arterial Pressure by a Naloxone-Insensitive Mechanism In the Rat", Biochemical and Biophysical Research Communications, (1997), pp. 309-312, vol. 234, The Academic Press.

Mark Conner, et al., "The Effect of Nociceptin on $Ca^{2+}$ Channel Current and Intracellular $Ca^{2+}$ In the SH-SY5Y Human Neuroblastoma Cell Line", British Journal of Pharmacology, (1996), pp. 205-207, vol. 118, Stockton Press.

Tristan Darland, et al., "Orphanin FQ/Nociceptin: a Role in Pain and Analgesia, But so Much More", Extracellular Space, (1998), pp. 215-221, vol. 21, No. 5, Elsevier Science Ltd.

E.S.L. Faber, et al., "Depression of Glutamatergic Transmission by Nociceptin in the Neonatal Rat Hemisected Spinal Cord Preparation in Vitro", Special Report.

Bulent Gumusel, et al., "Nociceptin: An Endogenous Agonist for Central Opioid Like$_1$ (ORL$_1$) Receptors Possesses Systemic Vasorelaxant Properties", Life Sciences, (1997), pp. 141-145, vol. 60, No. 8, Elsevier Science Inc.

Naoki Hara, et al., Characterization of Nociceptin Hyperalgesia and Allodynia in Conscious Mice, British Journal of Pharmacology, (1997), pp. 401-408, vol. 121, The Stockton Press.

Francois Jenck, et al., "Orphanin FQ Acts as a Anxiolytic to Attenuate Bhavioral Responses to Stress", Poc. Natl. Acad. Sci., (Dec. 1997), pp. 14854-14858, vol. 94.

Daniel R. Kapusta, et al., "Diuretic and Antinatriuretic Responses Produced by the Endogenes Opioid-Like Peptide, Nociceptin (Orphanin FQ)", Life Sciences, (1997), pp. 15-21, vol. 60, No. 1, Elsevier Science Inc.

Michael A. King, et al., "Spinal Analgesic Activity of Orphanin FQ/Nociceptin and its Fragments", Neuroscience Letters, (1997), pp. 113-116, vol. 223, Elsevier Science Ireland Ltd.

Frederic Knoflach, et al., "Modulation of Voltage-Gated Calcium Channels by Orphanin FQ in Freshly Dissociated Hippocampal Neurons", The Journal of Neuroscience, (Nov. 1, 1996), pp. 6657-6664, vol. 16, No. 21.

Toshiya Manabe, et al., "Facilitation of Long-Term Potentiation and Memory in Mice Lacking Nociceptin Receptors", Letters to Nature, (Aug. 6, 1998), pp. 577-581, vol. 394, Mcmillan Publishers Ltd.

Hans Matthes, et al., "Functional Selectively of Orphanin FQ for its Receptors Coexpressed with Potassium Channel Subunits in Xenopus Laevis Oocytes", Molecular Pharmacology, (1996), pp. 447-450, vol. 50, The American Society for Pharmacology and Experimental Therapeutics.

Jean-Claude Meunier, et al., "Isolation and Structure of the Endogenous Agonist of Opioid Receptor-Like ORL$_1$ Receptor", Letters to Nature, (Oct. 12, 1995), pp. 532-535, vol. 377.

Jeffrey S. Mogil, et al., "Functional Antagonism of u-,@-and k-Opioid Antinociceptin by Orphanin FQ", Neuroscience Letters, (1996), pp. 131-134, vol. 214, Elsevier Science Ireland Ltd.

J. S. Mogil, et al., "Orphanin FQ is a Functional Anti-Opioid Peptide", Neuroscience, (1996), pp. 333-337, vol. 75, No. 2, The Elsevier Science Ltd., PII: S0306-4522(96)00338-7.

Christiane Mollereau, et al., "ORL1, a Novel Member of the Opioid Receptor Family", FEBS Letters, (1994), pp. 33-38, vol. 341, Federation of European Biochemical Societies.

Miyuki Nishi, et al. "Unrestrained Nociceptin Response and Disregulation of Hearing Ability in Mice Lacking the Nociceptin/Orphanin FQ Receptor", The EMBO Journal, (1997), pp. 1858-1864, vol. 16, No. 8, Oxford University Press.

James D. Pomonis, et al., "Orphanin FQ, Agonist of Orphan Opioid Receptor ORL$_1$, Stimulates Feeding in Rats", NeuroReport, (1996), pp. 369-371, vol. 8.

Rainer K. Reinscheid, et al., "Orphanin FQ: A Neuropeptide that Activates an Opioidlike G Protein-Coupled Receptor", Science, (Nov. 3, 1995), pp. 792-794, vol. 270.

Y.-S. Shu, et al., "Orphanin FQ/Nociceptin Modualtes Glutamate- and Kainic Acid-Induced Currents in Acutely Isolated Rat Spinal Dorsal Horn Neurons", Neuropeptides, (1998), pp. 567-571, vol. 32, No. 6, Harcourt Brace& Co., Ltd.

Christopher W. Vaughan, et al., "Increase by the ORL$_1$Receptor (Opioid Receptor-Like$_1$ ) Ligand, Nociceptin, of Inwardly Rectifying K Conductance in Dorsal Raphe Nucleus Neurons", Special Report, 1609-1611.

Xiao-Jun Xu, et al., "Nociceptin or Antinociceptin: Potent Spinal Antinociceptive Effect of Orphanin FQ/Nociceptin in the Rat", NeuroReport, (Sep. 2, 1996), pp. 2092-2094, vol. 7, No. 13, Rapid Science Publishers.

Tatsuo Yamamoto, M.D., et al., "Effects of Intrathecally Administered Nociceptin, and Opioid Receptor-Like$_1$ Receptor Agonist, and N-Methyl-D-Aspartate Receptor Antagonists on the Thermal Hyperalgesia Induced by Partical Siatic Nerve Injury in the Rat", Anesthesiology, (1997), pp. 1145-1152, vol. 87, American Society of Anesthesiologists, Inc.

T. Yamamoto, et al., "Analgesic Effect of Intrathecally Administered Nociceptin, An Opioid Receptor-Like$_1$ Receptor Agonist, in the Rat Formalin Test", Neuroscience, (1997), pp. 249-254, vol. 81, No. 1, Elsevier Science Ltd., PII: S0306-4522(97)00166-8.

* cited by examiner

SUBSTITUTED CYCLOHEXANE-1,4-DIAMINE COMPOUNDS

CROSS-REFERENCE TO RELATED APPLICATIONS

This application is a continuation of International Patent Application No. PCT/EP02/05051, filed May 8, 2002, designating the United States of America, and published in German as WO 02/090317, the entire disclosure of which is incorporated herein by reference. Priority is claimed based on Federal Republic of Germany Patent Application No. DE 101 23 163.6, filed May 9, 2001.

FIELD OF THE INVENTION

The present invention relates to substituted cyclohexane-1,4-diamine compounds, processes for their preparation, medicaments comprising these compounds and the use of substituted cyclohexane-1,4-diamine compounds for the preparation of medicaments and for methods of treatment.

BACKGROUND OF THE INVENTION

The heptadecapeptide nociceptin is an endogenous ligand of the ORL1 (opioid receptor-like) receptor (Meunier et al., Nature 377, 1995, p. 532-535) which belongs to the family of opioid receptors and is to be found in many regions of the brain and spinal cord (Mollereau et al., FEBS Letters, 341, 1994, p. 33-38, Darland et al., Trends in Neurosciences, 21, 1998, p. 215-221). The peptide is characterized by a high affinity, with a Kd value of approximately 56 pM (Ardati et al., Mol. Pharmacol. 51, p. 816-824), and by a high selectivity for the ORL1 receptor. The ORL1 receptor is homologous to the μ, κ and δ opioid receptors, and the amino acid sequence of the nociceptin peptide has a strong similarity with those of the known opioid peptides. The nociceptin-induced activation of the receptor leads to an inhibition of adenylate cyclase via coupling with $G_{i/o}$ proteins (Meunier et al., Nature 377, 1995, p. 532-535). Functional similarities of the μ, κ and δ opioid receptors with the ORL1 receptor also exist at the cellular level in respect of activation of the potassium channel (Matthes et al., Mol. Pharmacol. 50, 1996, p. 447-450; Vaughan et al., Br. J. Pharmacol. 117, 1996, p. 1609-1611) and inhibition of the L-, N- and P/Q-type calcium channels (Conner et al., Br. J. Pharmacol. 118, 1996, p. 205-207; Knoflach et al., J. Neuroscience 16, 1996, p. 6657-6664).

After intercerebroventricular administration, the nociceptin peptide shows a pronociceptive and hyperalgesic activity in various animal models (Reinscheid et al., Science 270, 1995, p. 792-794; Hara et al., Br. J. Pharmacol. 121, 1997, p. 401-408). These findings can be explained as an inhibition of stress-induced analgesia (Mogil et al., Neurosci. Letters 214, 1996, p 131-134; and Neuroscience 75, 1996, p. 333-337). It has also been possible to detect an anxiolytic activity of nociceptin in this connection (Jenck et al., Proc. Natl. Acad. Sci. USA 94, 1997, 14854-14858).

On the other hand, it has also been possible to demonstrate an antinociceptive effect of nociceptin in various animal models, in particular after intrathecal administration. Nociceptin inhibits the activity of kainate- or glutamate-stimulated posterior route ganglia neurones (Shu et al., Neuropeptides, 32, 1998, 567-571) or glutamate-stimulated spinal cord neurones (Faber et al., Br. J. Pharmacol., 119, 1996, p. 189-190); it has an antinociceptive action in the tail flick test in the mouse (King et al., Neurosci. Lett., 223, 1997, 113-116), in the flexor-reflex model in the rat (Xu et al., NeuroReport, 7, 1996, 2092-2094) and in the formalin test on the rat (Yamamoto et al., Neuroscience, 81, 1997, p. 249-254). It has also been possible to demonstrate an antinociceptive action of nociceptin in models for neuropathic pain (Yamamoto and Nozaki-Taguchi, Anesthesiology, 87, 1997), which is particularly interesting in as much as the activity of nociceptin increases after axotomy of spinal nerves. This is in contrast to conventional opioids, the activity of which decreases under these conditions (Abdulla and Smith, J. Neurosci. 18, 1998, p. 9685-9694).

The ORL1 receptor is furthermore also involved in the regulation of further physiological and pathophysiological processes. These include, inter alia, learning and memory formation (Sandin et al., Eur. J. Neurosci., 9, 1997, p. 194-197; Manabe et al., Nature, 394, 1997, p. 577-581), hearing ability (Nishi et al., EMBO J., 16, 1997, p. 1858-1864), food intake (Pomonis et al., NeuroReport, 8, 1996, p. 369-371), regulation of blood pressure (Gumusel et al., Life Sci., 60, 1997, p. 141-145; Campion and Kadowitz, Biochem. Biophys. Res. Comm., 234, 1997, p. 309-312), epilepsy (Gutiérrez et al., Abstract 536.18, Society for Neuroscience, vol 24, 28th Ann. Meeting, Los Angeles, Nov. 7th-12th, 1998) and diuresis (Kapista et al., Life Sciences, 60, 1997, PL 15-21). An overview article by Calo et al. (Br. J. Pharmacol., 129, 2000, 1261-1283) gives an overview of the indications or biological processes in which the ORL1 receptor plays or with high probability could play a role. Those mentioned are, inter alia: analgesia, stimulation and regulation of food intake, influence on μ-agonists, such as morphine, treatment of withdrawal symptoms, reduction in the addiction potential of morphines, anxiolysis, modulation of motor activity, memory disorders, epilepsy; modulation of neurotransmitter secretion, in particular of glutamate, serotonin and dopamine, and therefore neurodegenerative diseases; influencing of the cardiovascular system, initiation of an erection, diuresis, antinatriuresis, electrolyte balance, arterial blood pressure, water retention diseases, intestinal motility (diarrhoea), relaxing effects on the respiratory tract, micturition reflex (urinary incontinence). The use of agonists and antagonists as anoretics, analgesics (also in co-administration with opioids) or nootropics is furthermore discussed.

The possible uses of compounds which bind to the ORL1 receptor and activate or inhibit this are correspondingly diverse.

The object of the present invention was to provide medicaments which act on the nociceptin/ORL1 receptor system and are therefore suitable for medicaments, in particular for treatment of the various diseases connected with this system according to the prior art or for use in the indications mentioned there.

The invention therefore provides substituted cyclohexane-1,4-diamine compounds, called compound group (A) in the following, of the general formula I

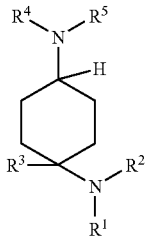

I wherein $R^1$ and $R^2$ independently of one another are chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted; wherein $R^1$ and $R^2$ may not both be H, or the radicals $R^1$ and $R^2$ together form a ring and denote $CH_2CH_2OCH_2CH_2$, $CH_2CH_2NR^6CH_2CH_2$ or $(CH_2)_{3-6}$, where $R^6$ is chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-8}$-alkylene and in each case mono- or polysubstituted or unsubstituted;

$R^3$ is chosen from $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-8}$-alkyl group and in each case unsubstituted or mono- or polysubstituted;

$R^4$ is chosen from H, $C_{1-8}$-alkyl, saturated or unsaturated, branched or unbranched, mono- or polysubstituted or unsubstituted; or $C(X)R^7$, $C(X)NR^7R^8$, $C(X)OR^9$, $C(X)SR^9$, $S(O_2)R^9$ where X=O or S, where $R^7$ is chosen from H, $C_{1-8}$s-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

where $R^8$ is chosen from H, $C_{1-4}$-alkyl, saturated or unsaturated, branched or unbranched, mono- or polysubstituted or unsubstituted or the radicals $R^7$ and $R^8$ together form a ring and denote $CH_2CH_2OCH_2CH_2$, $CH_2CH_2NR^{10}CH_2CH_2$ or $(CH_2)_{3-6}$, where $R^{10}$ is chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted;

where $R^9$ is chosen from $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

$R^5$ is chosen from $C_{3-8}$-cycloalkyl, aryl or heteroaryl, in each case unsubstituted or mono- or polysubstituted; $—CHR^{11}R^{12}$, $—CHR^{11}—CH_2R^{12}$, $—CHR^{11}—CH_2—CH_2R^{12}$, $—CHR^{11}—CH_2—CH_2—CH_2R^{12}$, $—C(Y)—CH_2R^{12}$, $—C(Y)—CH_2—CH_2R^{12}$ or $—C(Y)—CH_2—CH_2—CH_2R^{12}$ where Y=O, S or $H_2$, where $R^{11}$ is chosen from H, $C_{1-7}$-alkyl, saturated or unsaturated, branched or unbranched, mono- or polysubstituted or unsubstituted; or $C(O)O—C_{1-6}$-alkyl, saturated or unsaturated, branched or unbranched, mono- or polysubstituted or unsubstituted;

and where $R^{12}$ is chosen from

H; $C_{3-8}$-cycloalkyl, aryl or heteroaryl, in each case unsubstituted or mono- or polysubstituted, or $R^4$ and $R^5$ together form a heterocyclic radical having between 3 and 8 atoms in the ring, saturated or unsaturated; mono- or polysubstituted or unsubstituted, which heterocyclic radical may optionally be fused to further rings, with the proviso, that if $R^3$ is substituted or unsubstituted phenyl and at least one of $R^1$ or $R^2$ is H or $C_{1-8}$-alkyl, $R^4$ may not be alkyl and $R^4$ and $R^5$ may not together form a heterocyclic radical or that if $R^3$ is unsubstituted phenyl and $R^1$ and $R^2$ together denote $(CH_2)_5$, $R^4$ is chosen from H or $C_{1-8}$-alkyl, Y is not O or S and $R^5$ is not $C_{1-6}$-alkyl, optionally in the form of their racemates, of their pure stereoisomers, in particular enantiomers or diastereomers, or in the form of mixtures of the stereoisomers, in particular of the enantiomers or diastereomers, in any mixing ratio;

in the prepared form or in the form of their acids or their bases or in the form of their salts, in particular the physiologically acceptable salts or salts of physiologically acceptable acids or cations; or in the form of their solvates, in particular the hydrates.

A further object of the invention is achieved by providing substituted cyclohexane-1,4-diamine compounds, called compound group (B) in the following, of the general formula I

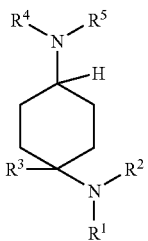

wherein

R¹ and R² independently of one another are chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted; wherein R¹ and R² may not both be H, or the radicals R¹ and R² together form a ring and denote $CH_2CH_2OCH_2CH_2$, $CH_2CH_2NR^6CH_2CH_2$ or $(CH_2)_{3-6}$, where R⁶ is chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted;

R³ is chosen from $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

R⁴ is chosen from H, $C_{1-8}$-alkyl, saturated or unsaturated, branched or unbranched, mono- or polysubstituted or unsubstituted; or $C(X)R^7$, $C(X)NR^7R^8$, $C(X)OR^9$, $C(X)SR^9$, $S(O_2)R^9$ where X=O or S, where R⁷ is chosen from H, $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

where R⁸ is chosen from H, $C_{1-4}$-alkyl, saturated or unsaturated, branched or unbranched, mono- or polysubstituted or unsubstituted or the radicals R⁷ and R⁸ together form a ring and denote $CH_2CH_2OCH_2CH_2$, $CH_2CH_2NR^{10}CH_2CH_2$ or $(CH_2)_{3-6}$, where R¹⁰ is chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted;

where R⁹ is chosen from $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

R⁵ is chosen from $C_{3-8}$-cycloalkyl, aryl or heteroaryl, in each case unsubstituted or mono- or polysubstituted; $-CHR^{11}R^{12}$, $-CHR^{11}-CH_2R^{12}$, $-CHR^{11}-CH_2-CH_2R^{12}$, $-CHR^{11}-CH_2-CH_2-CH_2R^{12}$, $-C(Y)R^{12}$, $-C(Y)-CH_2R^{12}$, $-C(Y)-CH_2-CH_2R^{12}$ or $-C(Y)-CH_2-CH_2-CH_2R^{12}$ where Y=O, S or $H_2$, where R¹¹ is chosen from H, $C_{1-7}$-alkyl, saturated or unsaturated, branched or unbranched, mono- or polysubstituted or unsubstituted; or $C(O)O-C_{1-6}$-alkyl, saturated or unsaturated, branched or unbranched, mono- or polysubstituted or unsubstituted;

and where R¹² is chosen from

H; $C_{3-8}$-cycloalkyl, aryl or heteroaryl, in each case unsubstituted or mono- or polysubstituted, optionally in the form of their racemates, of their pure stereoisomers, in particular enantiomers or diastereomers, or in the form of mixtures of the stereoisomers, in particular of the enantiomers or diastereomers, in any mixing ratio;

in the prepared form or in the form of their acids or their bases or in the form of their salts, in particular the physiologically acceptable salts or salts of physiologically acceptable acids or cations; or in the form of their solvates, in particular the hydrates.

A further object of the invention is achieved by providing substituted cyclohexane-1,4-diamine compounds, called compound group (C) in the following, of the general formula I

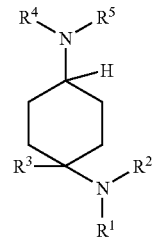

wherein

R¹ and R² independently of one another are chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted; wherein $R^1$ and $R^2$ may not both be H, $R^3$ is chosen from $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

$R^4$ is chosen from H, $C(X)R^7$, $C(X)NR^7R^8$, $C(X)OR^9$ or $C(X)SR^9$, $S(O_2)R^9$ where X=O or S, where $R^7$ is chosen from H, $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

where $R^8$ is chosen from H, $C_{1-4}$-alkyl, saturated or unsaturated, branched or unbranched, mono- or polysubstituted or unsubstituted or the radicals $R^7$ and $R^8$ together form a ring and denote $CH_2CH_2OCH_2CH_2$, $CH_2CH_2NR^{10}CH_2CH_2$ or $(CH_2)_{3-6}$, where $R^{10}$ is chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted;

where $R^9$ is chosen from $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

$R^5$ is chosen from $C_{3-8}$-cycloalkyl, aryl or heteroaryl, in each case unsubstituted or mono- or polysubstituted; —$CHR^{11}R^{12}$, —$CHR^{11}$—$CH_2R^{12}$, —$CHR^{11}$—$CH_2$—$CH_2R^{12}$, —$CHR^{11}$—$CH_2$—$CH_2$—$CH_2R^{12}$, —$C(Y)R^{12}$, —$C(Y)$—$CH_2R^{12}$, —$C(Y)$—$CH_2$—$CH_2R^{12}$ or —$C(Y)$—$CH_2$—$CH_2$—$CH_2R^{12}$ where Y=O, S or $H_2$, where $R^{11}$ is chosen from H, $C_{1-7}$-alkyl, saturated or unsaturated, branched or unbranched, mono- or polysubstituted or unsubstituted; or C(O)O—$C_{1-6}$-alkyl, saturated or unsaturated, branched or unbranched, mono- or polysubstituted or unsubstituted;

and where $R^{12}$ is chosen from

H; $C_{3-8}$-cycloalkyl, aryl or heteroaryl, in each case unsubstituted or mono- or polysubstituted, optionally in the form of their racemates, of their pure stereoisomers, in particular enantiomers or diastereomers, or in the form of mixtures of the stereoisomers, in particular of the enantiomers or diastereomers, in any mixing ratio;

in the prepared form or in the form of their acids or their bases or in the form of their salts, in particular the physiologically acceptable salts or salts of physiologically acceptable acids or cations; or in the form of their solvates, in particular the hydrates.

A further object of the invention is achieved by providing substituted cyclohexane-1,4-diamine compounds, called compound group (D) in the following, of the general formula I

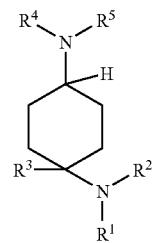

wherein $R^1$ and $R^2$ independently of one another are chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted; wherein $R^1$ and $R^2$ may not both be H, or the radicals $R^1$ and $R^2$ together form a ring and denote $CH_2CH_2OCH_2CH_2$, $CH_2CH_2NR^6CH_2CH_2$ or $(CH_2)_{3-6}$, where $R^6$ is chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted;

$R^3$ is chosen from $C_{1-8}$-alkyl or $C_{3-8}$-cycloalkyl, in each case saturated or unsaturated, branched or unbranched, mono- or polysubstituted or unsubstituted; heteroaryl, unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

$R^4$ is chosen from H, $C_{1-8}$-alkyl, saturated or unsaturated, branched or unbranched, mono- or polysubstituted or unsubstituted or $C(X)R^7$, $C(X)NR^7R^8$, $C(X)OR^9$, $C(X)SR^9$, $S(O_2)R^9$ where X=O or S, where $R^7$ is chosen from H, $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted C$_{1-4}$-alkyl group and in each case unsubstituted or mono- or polysubstituted;

where R$^8$ is chosen from H, C$_{1-4}$-alkyl, saturated or unsaturated, branched or unbranched, mono- or polysubstituted or unsubstituted or the radicals R$^7$ and R$^8$ together form a ring and denote CH$_2$CH$_2$OCH$_2$CH$_2$, CH$_2$CH$_2$NR$^{10}$CH$_2$CH$_2$ or (CH$_2$)$_{3-6}$, where R$^{10}$ is chosen from H; C$_{3-8}$-alkyl or C$_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, C$_{3-8}$-cycloalkyl or heteroaryl, bonded via C$_{1-3}$-alkylene and in each case mono- or polysubstituted or unsubstituted;

where R$^9$ is chosen from C$_{1-8}$-alkyl or C$_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, C$_{3-8}$-cycloalkyl or heteroaryl, bonded via a saturated or unsaturated, branched or unbranched, substituted or unsubstituted C$_{1-4}$-alkyl group and in each case unsubstituted or mono- or polysubstituted;

R$^5$ is chosen from C$_{3-8}$-cycloalkyl, aryl or heteroaryl, in each case unsubstituted or mono- or polysubstituted; —CHR$^{11}$R$^{12}$, —CHR$^{11}$—CH$_2$R$^{12}$, —CHR$^{11}$CH$_2$—CH$_2$R$^{12}$, —CHR$^{11}$—CH$_2$—CH$_2$—CH$_2$R$^{12}$, —C(Y)R$^{12}$, —C(Y)—CH$_2$R$^{12}$, —C(Y)—CH$_2$—CH$_2$R$^{12}$ or —C(Y)—CH$_2$—CH$_2$—CH$_2$R$^{12}$ where Y=O, S or H$_2$, where R$^{11}$ is chosen from H, C$_{1-7-7}$-alkyl, saturated or unsaturated, branched or unbranched, mono- or polysubstituted or unsubstituted; or C(O)O—C$_{1-6}$-alkyl, saturated or unsaturated, branched or unbranched, mono- or polysubstituted or unsubstituted;

and where R$^{12}$ is chosen from

H; C$_{3-8}$-cycloalkyl, aryl or heteroaryl, in each case unsubstituted or mono- or polysubstituted, or R$^4$ and R$^5$ together form a heterocyclic radical having between 3 and 8 atoms in the ring, saturated or unsaturated; mono- or polysubstituted or unsubstituted, which heterocyclic radical may optionally be fused to further rings, optionally in the form of their racemates, of their pure stereoisomers, in particular enantiomers or diastereomers, or in the form of mixtures of the stereoisomers, in particular of the enantiomers or diastereomers, in any mixing ratio;

in the prepared form or in the form of their acids or their bases or in the form of their salts, in particular the physiologically acceptable salts or salts of physiologically acceptable acids or cations; or in the form of their solvates, in particular the hydrates.

A further object of the invention is achieved by providing substituted cyclohexane-1,4-diamine compounds, called compound group (E) in the following, of the general formula I

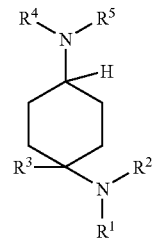

I wherein the radicals R$^1$ and R$^2$ together form a ring and denote CH$_2$CH$_2$OCH$_2$CH$_2$, CH$_2$CH$_2$NR$^6$CH$_2$CH$_2$ or (CH$_2$)$_{3-6}$, where R$^6$ is chosen from H; C$_{1-8}$-alkyl or C$_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, C$_{3-8}$-cycloalkyl or heteroaryl, bonded via C$_{1-3}$-alkylene and in each case mono- or polysubstituted or unsubstituted;

R$^3$ is chosen from C$_{1-8}$-alkyl or C$_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, C$_{3-8}$-cycloalkyl or heteroaryl, bonded via a saturated or unsaturated, branched or unbranched, substituted or unsubstituted C$_{1-4}$-alkyl group and in each case unsubstituted or mono- or polysubstituted;

R$^4$ is chosen from H, C$_{1-8}$-alkyl, saturated or unsaturated, branched or unbranched, mono- or polysubstituted or unsubstituted or C(X)R$^7$, C(X)NR$^7$R$^8$, C(X)OR$^9$, C(X)SR$^9$, S(O$_2$)R$^9$ where X=O or S, where R$^7$ is chosen from H, C$_{1-8}$-alkyl or C$_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, C$_{3-8}$-cycloalkyl or heteroaryl, bonded via a saturated or unsaturated, branched or unbranched, substituted or unsubstituted C$_{1-4}$-alkyl group and in each case unsubstituted or mono- or polysubstituted;

where R$^8$ is chosen from H, C$_{1-4}$-alkyl, saturated or unsaturated, branched or unbranched, mono- or polysubstituted or unsubstituted or the radicals R$^7$ and R$^8$ together form a ring and denote CH$_2$CH$_2$OCH$_2$CH$_2$, CH$_2$CH$_2$NR$^{10}$CH$_2$CH$_2$ or (CH$_2$)$_{3-6}$, where R$^{10}$ is chosen from H; C$_{1-8}$-alkyl or C$_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, C$_{3-8}$-cycloalkyl or heteroaryl, bonded via C$_{1-3}$-alkylene and in each case mono- or polysubstituted or unsubstituted;

where R$^9$ is chosen from C$_{1-8}$-alkyl or C$_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

$R^5$ is chosen from $C_{3-8}$-cycloalkyl, aryl or heteroaryl, in each case unsubstituted or mono- or polysubstituted; —CHR$^{11}$R$^{12}$, —CHR$^{11}$—CH$_2$R$^{12}$, —CHR$^{11}$—CH$_2$—CH$_2$R$^{12}$, —CHR$^{11}$—CH$_2$—CH$_2$—CH$_2$R$^{12}$, —C(Y)R$^{12}$, —C(Y)—CH$_2$R$^{12}$, —C(Y)—CH$_2$—CH$_2$R$^{12}$ or —C(Y)—CH$_2$—CH$_2$—CH$_2$R$^{12}$ where Y=O, S or H$_2$, where $R^{11}$ is chosen from
H, $C_{1-7}$-alkyl, saturated or unsaturated, branched or unbranched, mono- or polysubstituted or unsubstituted; or C(O)O—$C_{1-6}$-alkyl, saturated or unsaturated, branched or unbranched, mono- or polysubstituted or unsubstituted;
and where $R^{12}$ is chosen from $C_{3-8}$-cycloalkyl, aryl or heteroaryl, in each case unsubstituted or mono- or polysubstituted, or $R^4$ and $R^5$ together form a heterocyclic radical having between 3 and 8 atoms in the ring, saturated or unsaturated; mono- or polysubstituted or unsubstituted, which heterocyclic radical may optionally be fused to further rings, optionally in the form of their racemates, of their pure stereoisomers, in particular enantiomers or diastereomers, or in the form of mixtures of the stereoisomers, in particular of the enantiomers or diastereomers, in any mixing ratio;

in the prepared form or in the form of their acids or their bases or in the form of their salts, in particular the physiologically acceptable salts or salts of physiologically acceptable acids or cations; or in the form of their solvates, in particular the hydrates.

All these compounds and compound groups according to the invention show outstanding binding to the ORL1 receptor.

Compounds which show a certain relationship to the compounds proposed here are known from the following publications:

The connected U.S. Pat. Nos. 4,460,604, 4,447,454 and 4,113,866 (Lednicer et al.). In these, the compounds mentioned are described as having an analgesic reaction, without reference being made to the ORL1 receptor.

U.S. Pat. No. 5,304,479 (Lin et al.). The compounds described there are intended for use in analytical test systems for the determination of phencyclidine (PCP), in particular in body fluids, without reference being made to the ORL1 receptor.

De Costa et al., J. Chem. Soc., Perkin Trans. 1 (1992), 1671-80. The compounds mentioned are mentioned in connection with the synthesis of irreversible ligands at the dopamine reuptake site, without reference being made to the ORL1 receptor.

In the context of this invention, alkyl and cycloalkyl radicals are understood as meaning saturated and unsaturated (but not aromatic), branched, unbranched and cyclic hydrocarbons, which can be unsubstituted or mono- or polysubstituted. $C_{1-2}$-Alkyl means C1- or C2-alkyl, $C_{1-3}$-alkyl means C1-, C2- or C3-alkyl, $C_{1-4}$-alkyl means C1-, C2-, C3- or C4-alkyl, $C_{1-5}$-alkyl means C1-, C2-, C3, C4- or C5-alkyl, $C_{1-6}$-alkyl means C1-, C2-, C3-, C4-, C5- or C6-alkyl, $C_{1-7}$-alkyl means C1-, C2-, C3-, C4-, C5-, C6- or C7-alkyl, $C_{1-8}$-alkyl means C1-, C2-, C3-, C4-, C5-, C6-, C7 or C8-alkyl, $C_{1-10}$-alkyl means C1-, C2-, C3-, C4-, C5-, C6-, C7-, C8-, C9-, C10-alkyl and $C_{1-18}$-alkyl means C1-, C2-, C3-, C4-, C5-, C6-, C7-, C8-, C9-, C10-, C11-, C12-, C13-, C14-, C15-, C16-, C17 or C18-alkyl. Furthermore, $C_{3-4}$-cycloalkyl means C3- or C4-cycloalkyl, $C_{3-5}$-cycloalkyl means C3-, C4- or C5-cycloalkyl, $C_{3-6}$-cycloalkyl means C3-, C4-, C5- or C6-cycloalkyl, $C_{3-7}$-cycloalkyl means C3-, C4-, C5-, C6- or C7-cycloalkyl, $C_{3-8}$-cycloalkyl means C3-, C4-, C5-, C6-, C7 or C8-cycloalkyl, $C_{4-5}$-cycloalkyl means C4- or C5-cycloalkyl, $C_{4-6}$-cycloalkyl means C4-, C5- or C6-cycloalkyl, $C_{4-7}$-cycloalkyl means C4-, C5-, C6- or C7-cycloalkyl, $C_{5-6}$-cycloalkyl means C5- or C6-cycloalkyl and $C_{5-7}$-cycloalkyl means C5-, C6- or C7-cycloalkyl. In respect of cycloalkyl, the term also includes saturated cycloalkyls in which one or 2 carbon atoms are replaced by a heteroatom, S, N or O. However, the term cycloalkyl also includes in particular mono- or polyunsaturated, preferably monounsaturated, cycloalkyls without a heteroatom in the ring, provided the cycloalkyl is not an aromatic system. The alkyl and cycloalkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, and also adamantyl, CHF$_2$, CF$_3$ or CH$_2$OH, as well as pyrazolinone, oxopyrazolinone, [1,4]dioxane or dioxolane.

In connection with alkyl and cycloalkyl—unless expressly defined elsewhere—the term substituted here is understood in the context of this invention as meaning substitution of at least one (optionally also of more than one) hydrogen radical by F, Cl, Br, I, NH$_2$, SH or OH, where "polysubstituted" or "substituted" in the case of polysubstitution is to be understood as meaning that the substitution occurs several times with the same or different substituents both on different and on the same atoms, for example three times on the same C atom, as in the case of CF$_3$, or at different places, as in the case of —CH(OH)—CH=CH—CHCl$_2$. Particularly preferred substituents here are F, Cl and OH. In respect of cycloalkyl, the hydrogen radical can also be replaced by OC$_{1-3}$-alkyl or C$_{1-3}$-alkyl (in each case mono- or polysubstituted or unsubstituted), in particular methyl, ethyl, n-propyl, isopropyl, CF$_3$, methoxy or ethoxy.

The term (CH$_3$)$_{3-6}$ is understood as meaning —CH$_2$—CH$_2$—CH$_2$—, —CH$_2$—CH$_2$—CH$_2$—CH$_2$—, —CH$_2$—CH$_2$—CH$_2$—CH$_2$—CH$_2$— and —CH$_2$—CH$_2$—CH$_2$—CH$_2$—CH$_2$—CH$_2$—, (CH$_2$)$_{1-4}$ is understood as meaning —CH$_2$—, —CH$_2$—CH$_2$—, —CH$_2$—CH$_2$—CH$_2$— and —CH$_2$—CH$_2$—CH$_2$—CH$_2$—, (CH$_2$)$_{4-5}$ is understood as meaning —CH$_2$—CH$_2$—CH$_2$—CH$_2$— and —CH$_2$—CH$_2$—CH$_2$—CH$_2$—CH$_2$—, etc.

An aryl radical is understood as meaning ring systems with at least one aromatic ring but without heteroatoms in even only one of the rings. Examples are phenyl, naphthyl, fluoranthenyl, fluorenyl, tetralinyl or indanyl, in particular 9H-fluorenyl or anthracenyl radicals, which can be unsubstituted or mono- or polysubstituted.

A heteroaryl radical is understood as meaning heterocyclic ring systems with at least one unsaturated ring, which contain one or more heteroatoms from the group consisting of nitrogen, oxygen and/or sulfur and can also be mono- or polysubstituted. Examples which may be mentioned from the group of heteroaryls are furan, benzofuran, thiophene, benzothiophene, pyrrole, pyridine, pyrimidine, pyrazine, quinoline, isoquinoline, phthalazine, benzo[1,2,5]-thiadiazole, benzothiazole, indole, benzotriazole, benzodioxolane, benzodioxane, carbazole, indole and quinazoline.

In connection with aryl and heteroaryl, substituted here is understood as meaning substitution of the aryl or heteroaryl with $R^{22}$, $OR^{22}$ a halogen, preferably F and/or Cl, a $CF_3$, a CN, an $NO_2$, an $NR^{23}R^{24}$, a $C_{1-6}$-alkyl (saturated), a $C_{1-6}$-alkoxy, a $C_{3-8}$-cycloalkoxy, a $C_{3-8}$-cycloalkyl or a $C_{2-6}$-alkylene.

The radical $R^{22}$ here represents H, a $C_{1-6}$-alkyl, preferably a $C_{1-6}$-alkyl, an aryl or heteroaryl or an aryl or heteroaryl radical bonded via $C_{1-3}$-alkyl, saturated or unsaturated, or via a $C_{1-3}$-alkylene group, wherein these aryl and heteroaryl radicals may not themselves be substituted by aryl or heteroaryl radicals, the radicals $R^{23}$ and $R^{24}$, which are identical or different, denote H, a $C_{1-10}$-alkyl, preferably a $C_{1-6}$-alkyl, an aryl, a heteroaryl or an aryl or heteroaryl radical bonded via $C_{1-3}$-alkyl, saturated or unsaturated, or via a $C_{1-3}$-alkylene group, wherein these aryl and heteroaryl radicals may not themselves be substituted by aryl or heteroaryl radicals, or the radicals $R^{23}$ and $R^{24}$ together denote $CH_2CH_2OCH_2CH_2$, $CH_2CH_2NR^{25}CH_2CH_2$ or $(CH_2)_{3-6}$, and the radical $R^{25}$ denotes H, a $C_{1-10}$-alkyl, preferably a $C_{1-6}$-alkyl, an aryl or heteroaryl radical or an aryl or heteroaryl radical bonded via $C_{1-3}$-alkyl, saturated or unsaturated, or via a $C_{1-3}$-alkylene group, wherein these aryl and heteroaryl radicals may not themselves be substituted by aryl or heteroaryl radicals.

The term salt is understood as meaning any form of the active compound according to the invention in which the active compound assumes an ionic form or is charged and is coupled with a counter-ion (a cation or anion) or is in solution. The term is also understood as meaning complexes of the active compound with other molecules and ions, in particular complexes complexed via ionic interactions. In particular, the term is understood as meaning (and this is also a preferred embodiment of this invention) physiologically acceptable salts, in particular physiologically acceptable salts with cations or bases and physiologically acceptable salts with anions or acids or also a salt formed with a physiologically acceptable acid or a physiologically acceptable cation.

The term of the physiologically acceptable salt with anions or acids is understood in the context of this invention as meaning salts of at least one of the active compounds according to the invention—in most cases protonated, for example at the nitrogen—as the cation with at least one anion, which are physiologically—especially when used in humans and/or mammals—acceptable. In particular, the term is understood in the context of this invention as meaning the salt formed with a physiologically acceptable acid, namely salts of the particular active compound with inorganic or organic acids which are physiologically—especially when used in humans and/or mammals—acceptable. Examples of physiologically acceptable salts of particular acids are salts of:

hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, 1,1-dioxo-1,2-dihydro1b6-benzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethyl-benzoic acid, a-liponic acid, acetylglycine, acetyl- salicylic acid, hippuric acid and/or aspartic acid. The hydrochloride salt is particularly preferred.

The term of the salt formed with a physiologically acceptable acid is understood in the context of this invention as meaning salts of the particular active compound with inorganic or organic acids which are physiologically—especially when used in humans and/or mammals—acceptable. The hydrochloride is particularly preferred. Examples of physiologically acceptable acids are: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydro1$\lambda^6$-benzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, acetylsalicylic acid, hippuric acid and/or aspartic acid. The hydrochloride salt is particularly preferred.

The term of the physiologically acceptable salt with cations or bases is understood in the context of this invention as meaning salts of at least one of the compounds according to the invention—in most cases of a (deprotonated) acid—as the anion with at least one cation, preferably an inorganic cation, which are physiologically—especially when used in humans and/or mammals—acceptable. The salts of the alkali metals and alkaline earth metals and also $NH_4^+$ are particularly preferred, but in particular (mono-) or (di-) sodium, (mono-) or (di-) potassium, magnesium or calcium salts.

The term of the salt formed with a physiologically acceptable cation is understood in the context of this invention as meaning salts of at least one of the particular compounds as the anion with at least one inorganic cation which is physiologically—especially when used in humans and/or mammals—acceptable. The salts of the alkali metals and alkaline earth metals and also $NH_4^+$ are particularly preferred, but in particular (mono-) or (di-)sodium, (mono-) or (di-) potassium, magnesium or calcium salts.

In a preferred embodiment of the compound groups (A), (B) or (D), the substituted cyclohexane-1,4-diamine compounds are built up such that, according to formula I, $R^1$ and $R^2$ independently of one another are chosen from H; $C_{1-8}$-alkyl, saturated or unsaturated, branched or unbranched, mono- or polysubstituted or unsubstituted; wherein $R^1$ and $R^2$ may not both be H, or the radicals $R^1$ and $R^2$ together form a ring and denote $CH_2CH_2OCH_2CH_2$, $CH_2CH_2NR^6CH_2CH_2$ or $(CH_2)_{3-6}$, where $R^6$ is chosen from H; $C_{1-8}$-alkyl, saturated or unsaturated, branched or unbranched, mono- or polysubstituted or unsubstituted, preferably $R^1$ and $R^2$ independently of one another are chosen from H; $C_{3-8}$-alkyl, saturated or unsaturated, branched or unbranched, mono- or polysubstituted or unsubstituted; wherein $R^1$ and $R^2$ may not both be H, or the radicals $R^1$ and $R^2$ together form a ring and denote $(CH_2)_{4-5}$, in particular $R^1$ and $R^2$ independently of one another are chosen from methyl or ethyl or the radicals $R^1$ and $R^2$ together form a ring and denote $(CH_2)_5$.

In a preferred embodiment of the compound group (E), the substituted cyclohexane-1,4-diamine compounds are built up such that, according to formula I R$^1$ and R$^2$ together form a ring and denote CH$_2$CH$_2$OCH$_2$CH$_2$, CH$_2$CH$_2$NR$^6$CH$_2$CH$_2$ or (CH$_2$)$_{3-6}$;
where R$^6$ is chosen from H; C$_{1-8}$-alkyl, saturated or unsaturated, branched or unbranched, mono- or polysubstituted or unsubstituted,
preferably
R$^1$ and R$^2$ together form a ring and denote (CH$_2$)$_{4-5}$,
in particular
R$^1$ and R$^2$ together form a ring and denote (CH$_2$)$_5$.

In a preferred embodiment of compound group (C), the substituted cyclohexane-1,4-diamine compounds are built up such that, according to formula I,
R$^1$ and R$^2$ independently of one another are chosen from H; C$_{1-8}$-alkyl, saturated or unsaturated, branched or unbranched, mono- or polysubstituted or unsubstituted; wherein R$^1$ and R$^2$ may not both be H,
preferably
R$^1$ and R$^2$ independently of one another are chosen from H; C$_{1-4}$-alkyl, saturated or unsaturated, branched or unbranched, mono- or polysubstituted or unsubstituted; wherein R$^1$ and R$^2$ may not both be H,
in particular
R$^1$ and R$^2$ independently of one another are chosen from methyl or ethyl.

In a preferred embodiment of compound groups (A), (B) or (C), the substituted cyclohexane-1,4-diamine compounds are built up such that, according to formula I,
R$^3$ is chosen from C$_{3-8}$-cycloalkyl, aryl or heteroaryl, in each case unsubstituted or mono- or polysubstituted; aryl, C$_{3-8}$-cycloalkyl or heteroaryl, bonded via a saturated or unsaturated, unbranched, substituted or unsubstituted C$_{1-2}$-alkyl group and in each case unsubstituted or mono- or polysubstituted;
preferably
R$^3$ is chosen from C$_{5-6}$-cycloalkyl, phenyl, naphthyl, anthracenyl, thiophenyl, benzothiophenyl, furyl, benzofuranyl, benzodioxolanyl, indolyl, indanyl, benzodioxanyl, pyrrolyl, pyrimidyl or pyrazinyl, in each case unsubstituted or mono- or polysubstituted; C$_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl, bonded via a saturated, unbranched C$_{1-2}$-alkyl group and in each unsubstituted or mono- or polysubstituted;
in particular
R$^3$ is chosen from phenyl, furyl, thiophenyl, cyclohexanyl, naphthyl, benzofuranyl, indolyl, indanyl, benzodioxanyl, benzodioxolanyl, pyrrolyl, pyrimidyl, pyrazinyl or benzothiophenyl, in each case unsubstituted or mono- or polysubstituted; phenyl, furyl or thiophenyl, bonded via a saturated, unbranched C$_{1-2}$-alkyl group and in each case unsubstituted or mono- or polysubstituted.

In a preferred embodiment of compound group (D), the substituted cyclohexane-1,4-diamine compounds are built up such that, according to formula I
R$^3$ is chosen from C$_{3-8}$-cycloalkyl or heteroaryl, in each case unsubstituted or mono- or polysubstituted; aryl, C$_{3-8}$-cycloalkyl or heteroaryl, bonded via a saturated or unsaturated, unbranched, substituted or unsubstituted C$_{1-4}$-alkyl group and in each case unsubstituted or mono- or polysubstituted;
preferably
R$^3$ is chosen from C$_{5-6}$-cycloalkyl, thiophenyl, benzothiophenyl, furyl, benzofuranyl, benzodioxolanyl, indolyl, indanyl, benzodioxanyl, pyrrolyl, pyrimidyl or pyrazinyl, in each case unsubstituted or mono- or polysubstituted; C$_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl, bonded via a saturated, unbranched C$_{1-2}$-alkyl group and in each case unsubstituted or mono- or polysubstituted;
in particular
R$^3$ is chosen from furyl, thiophenyl, cyclohexanyl, benzofuranyl, indolyl, indanyl, benzodioxanyl, benzodioxolanyl, pyrrolyl, pyrimidyl, pyrazinyl or benzothiophenyl, in each case unsubstituted or polysubstituted; phenyl, furyl or thiophenyl, bonded via a saturated, unbranched C$_{1-2}$-alkyl group and in each case unsubstituted or mono- or polysubstituted.

In a preferred embodiment of all the above compounds and compound groups according to the invention, the substituted cyclohexane-1,4-diamine compounds are built up such that, according to formula I, R$^4$ is H.

In a preferred embodiment of all the above compounds and compound groups according to the invention, the substituted cyclohexane-1,4-diamine compounds are built up such that, according to formula I
R$^4$ is chosen from H, C(X)R$^7$, C(X)NR$^7$R$^8$, C(X)OR$^9$, C(X)SR$^9$ or S(O$_2$)R$^9$, where X=O or S,
preferably
R$^4$ is chosen from H, C(X)R$^7$, C(X)NR$^7$R$^8$ or C(X)OR$^9$, where X=O,
in particular
R$^4$ is chosen from H or C(O)R$^7$; preferably where R$^7$ is chosen from
H; or C$_{1-8}$-alkyl, saturated or unsaturated, branched or unbranched, mono- or polysubstituted or unsubstituted;
preferably
H; or C$_{1-3}$-alkyl, saturated, unsubstituted, branched or unbranched;
in particular CH$_3$.

In a preferred embodiment of compound groups (A), (D) or (E), the substituted cyclohexane-1,4-diamine compounds are built up such that, according to formula I,
R$^4$ and R$^5$ together form a heterocyclic radical having between 3 and 8 atoms in the ring, saturated or unsaturated; mono- or polysubstituted or unsubstituted, preferably having between 5 and 7 atoms in the ring, of which, in addition to the obligatory N, 0 to 1 further heteroatoms chosen from N, S or O are in the ring;
wherein the heterocyclic radical formed by R$^4$ and R$^5$ together may optionally be fused to further rings,
preferably to aromatic and/or heteroaromatic rings, wherein those rings can be fused to further aromatic and/or heteroaromatic rings,
in particular the heterocyclic radical formed by R$^4$ and R$^5$ together is fused to one or two further rings,
preferably the heterocyclic radical formed by R$^4$ and R$^5$ together is so fused to two further rings that R$^4$ and R$^5$ together denote

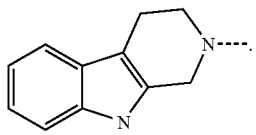

In a preferred embodiment of compound groups (A), (D) or (E), the substituted cyclohexane-1,4-diamine compounds are built up such that, according to formula I $R^4$ is chosen from H or $C_{1-8}$-alkyl, saturated or unsaturated, branched or unbranched, mono- or polysubstituted or unsubstituted,
preferably
H or $C_{1-6}$-alkyl, saturated or unsaturated, branched or unbranched, mono- or polysubstituted or unsubstituted,
in particular
H or $C_{1-3}$-alkyl, saturated, unbranched and unsubstituted.

In a preferred embodiment of all the above compounds and compound groups according to the invention, the substituted cyclohexane-1,4-diamine compounds are built up such that, according to formula I $R^5$ is chosen from $C_{3-8}$-cycloalkyl, aryl or heteroaryl, in each case unsubstituted or mono- or polysubstituted;
preferably
$R^5$ is chosen from cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, in each case unsubstituted or mono- or polysubstituted;
in particular
$R^5$ is chosen from cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, in each case unsubstituted or mono- or polysubstituted.

In a further particularly preferred embodiment of all the above compounds and compound groups according to the invention, the substituted cyclohexane-1,4-diamine compounds are built up such that, according to formula I, $R^5$ is chosen from —$CHR^{11}R^{12}$, —$CHR^{11}$—$CH_2R^{12}$, —$CHR^{11}$—$CH_2$—$CH_2R^{12}$, —$CHR^{11}$—$CH_2$—$CH_2$—$CH_2R^{12}$, —$C(Y)R^{12}$, —$C(Y)$—$CH_2R^{12}$, —$C(Y)$—$CH_2$—$CH_2R^{12}$ or —$C(Y)$—$CH_2$—$CH_2$—$CH_2R^{12}$
where Y=O, S or $H_2$,
preferably
$R^5$ is chosen from —$CHR^{11}R^{12}$, —$CHR^{11}$—$CH_2R^{12}$, —$CHR^{11}$—$CH_2$—$CH_2R^{12}$, —$C(Y)R^{12}$, —$C(Y)$—$CH_2R^{12}$ or —$C(Y)$—$CH_2$—$CH_2R^{12}$
where Y=O or S,
in particular
$R^5$ is chosen from —$CHR^{11}R^{12}$, —$CHR^{11}$—$CH_2R^{12}$, —$CHR^{11}$—$CH_2$—$CH_2R^{12}$, —$C(Y)R^{12}$ or —$C(Y)$—$CH_2R^{12}$
where Y=O.

In respect of this embodiment, it is particularly preferable if $R^{11}$ is chosen from
H, $C_{1-4}$-alkyl, saturated or unsaturated, branched or unbranched, mono- or polysubstituted or unsubstituted; or C(O)O—$C_{1-4}$-alkyl, saturated or unsaturated, branched or unbranched, mono- or polysubstituted or unsubstituted;
preferably
H, $C_{1-4}$-alkyl, saturated or unsaturated, branched or unbranched, mono- or polysubstituted or unsubstituted; or C(O)O—$C_{1-2}$-alkyl, saturated, unbranched, mono- or poly-substituted or unsubstituted;
in particular
H, $CH_3$, $C_2H_5$ and C(O)O—$CH_3$;

and/or it is also particularly preferable if
$R^{12}$ is chosen from $C_{3-8}$-cycloalkyl, aryl or heteroaryl, in each case unsubstituted or mono- or polysubstituted;
preferably
$R^{12}$ is chosen from cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, in each case unsubstituted or mono- or polysubstituted;
in particular
$R^{12}$ is chosen from cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, in each case unsubstituted or mono- or polysubstituted.

Furthermore, it is particularly preferable for the substituted cyclohexane-1,4-diamine compounds according to the invention to be chosen in particular from the following group:

N'-benzyl-N,N-dimethyl-1-phenyl-cyclohexane-1,4-diamine hydrochloride, nonpolar diastereomer
N'-benzyl-N,N-dimethyl-1-phenyl-cyclohexane-1,4-diamine hydrochloride, polar diastereomer
1,N'-dibenzyl-N,N-dimethyl-cyclohexane-1,4-diamine hydrochloride, nonpolar diastereomer
1,N'-dibenzyl-N,N-dimethyl-cyclohexane-1,4-diamine hydrochloride, polar diastereomer
N-(4-benzyl-4-dimethylamino-cyclohexyl)-N-propyl-benzamide hydrochloride
N,N-dimethyl-1-phenyl-N'-propyl-cyclohexane-1,4-diamine hydrochloride, nonpolar diastereomer
N-(4-dimethylamino-4-phenyl-cyclohexyl)-N-propyl-benzamide hydrochloride, nonpolar diastereomer
N-(4-dimethylamino-4-phenyl-cyclohexyl)-N-propyl-benzamide hydrochloride, polar diastereomer
1,N'-dibenzyl-N,N,N'-trimethyl-cyclohexane-1,4-diamine hydrochloride, nonpolar diastereomer
1,N'-dibenzyl-N,N,N'-trimethyl-cyclohexane-1,4-diamine hydrochloride, polar diastereomer
N-(4-benzyl-4-dimethylamino-cyclohexyl)-N-methyl-benzamide hydrochloride, polar diastereomer N-(4-benzyl-4-dimethylamino-cyclohexyl)-N-ethyl-benzamide hydrochloride, polar diastereomer
1-benzyl-N'-(1H-indol-3-ylmethyl)-N,N-dimethyl-cyclohexane-1,4-diamine dihydrochloride
1-benzyl-N'-[2-(1H-indol-3-yl)-1-methyl-ethyl]-N,N-dimethyl-cyclohexane-1,4-diamine, cis/trans mixture
1-benzyl-N'-indan-5-yl-N,N-dimethyl-cyclohexane-1,4-diamine hydrochloride
1-benzyl-N'-indan-1-yl-N,N-dimethyl-cyclohexane-1,4-diamine dihydrochloride, cis/trans mixture
N'-indan-1-yl-N,N-dimethyl-1-phenyl-cyclohexane-1,4-diamine
N'-(1H-indol-5-yl)-N,N-dimethyl-1-phenyl-cyclohexane-1,4-diamine
N'-(1H-indol-3-ylmethyl)-N,N-dimethyl-1-phenyl-cyclohexane-1,4-diamine, cis/trans mixture
N'-(1H-indol-3-ylmethyl)-N,N-dimethyl-1-phenyl-cyclohexane-1,4-diamine, nonpolar diastereomer
N'-[2-(1H-indol-3-yl)-ethyl]-N,N-dimethyl-1-phenyl-cyclohexane-1,4-diamine, nonpolar diastereomer
N'-[2-(1H-indol-3-yl)-ethyl]-N,N-dimethyl-1-phenyl-cyclohexane-1,4-diamine, cis/trans mixture
N'-indan-5-yl-N,N-dimethyl-1-phenyl-cyclohexane-1,4-diamine, nonpolar diastereomer
N'-[2-(1H-indol-3-yl)-1-methyl-ethyl]-N,N-dimethyl-1-phenyl-cyclohexane-1,4-diamine, nonpolar diastereomer
N'-[2-(1H-indol-3-yl)-1-methyl-ethyl]-N,N-dimethyl-1-phenyl-cyclohexane-1,4-diamine, cis/trans mixture
N'-[2-(5-benzyloxy-1H-indol-3-yl)-ethyl]-N,N-dimethyl-1-phenyl-cyclohexane-1,4-diamine, cis/trans mixture
N'-(9H-fluoren-1-yl)-N,N-dimethyl-1-phenyl-cyclohexane-1,4-diamine dihydrochloride
N'-indan-2-yl-N,N-dimethyl-1-phenyl-cyclohexane-1,4-diamine dihydrochloride, cis/trans mixture
N'-(9H-fluoren-9-yl)-N,N-dimethyl-1-phenyl-cyclohexane-1,4-diamine dihydrochloride, cis/trans mixture
1-benzyl-N'-(9H-fluoren-9-yl)-N,N-dimethyl-cyclohexane-1,4-diamine
1-benzyl-N'-(1H-indol-3-ylmethyl)-N,N-dimethyl-cyclohexane-1,4-diamine, cis/trans mixture
N,N-dimethyl-N'-(1-methyl-1H-indol-3-ylmethyl)-1-phenyl-cyclohexane-1,4-diamine, cis/trans mixture
N,N-dimethyl-N'-(1-methyl-1H-indol-3-ylmethyl)-1-phenyl-cyclohexane-1,4-diamine, polar diastereomer
N'-(2-benzo[b]thiophen-3-yl-ethyl)-N,N-dimethyl-1-phenyl-cyclohexane-1,4-diamine dihydrochloride, cis/trans mixture
N'-(2-benzo[b]thiophen-3-yl-ethyl)-1-benzyl-N,N-dimethylcyclohexane-1,4-diamine dihydrochloride, cis/trans mixture
N'-acenaphthen-1-yl-N,N-dimethyl-1-phenyl-cyclohexane-1,4-diamine dihydrochloride, polar diastereomer
N'-acenaphthen-1-yl-N,N-dimethyl-1-phenyl-cyclohexane-1,4-diamine dihydrochloride, nonpolar diastereomer
N'-benzo[b]thiophen-5-yl-1-benzyl-N,N-dimethyl-cyclohexane-1,4-diamine dihydrochloride, nonpolar diastereomer
N'-benzo[b]thiophen-5-yl-N,N-dimethyl-1-phenyl-cyclohexane-1,4-diamine hydrochloride, nonpolar diastereomer
N'-benzothiazol-6-yl-N,N-dimethyl-1-phenyl-cyclohexane-1,4-diamine dihydrochloride, nonpolar diastereomer
N'-benzo[1,2,5]thiadiazol-4-yl-N,N-dimethyl-1-phenyl-cyclohexane-1,4-diamine dihydrochloride, polar diastereomer
N'-[2-(1H-indol-3-yl)-1-methyl-ethyl]-N,N-dimethyl-1-phenyl-cyclohexane-1,4-diamine dihydrochloride, nonpolar diastereomer
N'-adamantan-2-yl-N,N-dimethyl-1-phenyl-cyclohexane-1,4-diamine dihydrochloride
N'-(9-ethyl-9H-carbazol-3-yl)-N,N-dimethyl-1-phenyl-cyclohexane-1,4-diamine dihydrochloride, nonpolar diastereomer
N'-(3H-benzotriazol-5-yl)-N,N-dimethyl-1-phenyl-cyclohexane-1,4-diamine hydrochloride, nonpolar diastereomer
N'-(3H-benzotriazol-5-yl)-N,N-dimethyl-1-phenyl-cyclohexane-1,4-diamine hydrochloride, polar diastereomer
N'-(9H-fluoren-9-yl)-N,N-dimethyl-1-thiophen-2-yl-cyclohexane-1,4-diamine dihydrochloride, cis/trans mixture
N'-cyclooctyl-N,N-dimethyl-1-phenyl-cyclohexane-1,4-diamine dihydrochloride
N'-(1H-indol-3-ylmethyl)-N,N-dimethyl-1-phenyl-cyclohexane-1,4-diamine dihydrochloride, nonpolar diastereomer
N'-(1H-indol-3-ylmethyl)-N,N-dimethyl-1-phenyl-cyclohexane-1,4-diamine dihydrochloride, polar diastereomer
N'-benzo[b]thiophen-3-ylmethyl-N,N-dimethyl-1-phenyl-cyclohexane-1,4-diamine dihydrochloride, nonpolar diastereomer
N'-benzo[b]thiophen-3-ylmethyl-N,N-dimethyl-1-phenyl-cyclohexane-1,4-diamine dihydrochloride, polar diastereomer
N'-anthracen-2-yl-N,N-dimethyl-1-phenyl-cyclohexane-1,4-diamine hydrochloride, nonpolar diastereomer
N'-benzo[b]thiophen-3-ylmethyl-1-benzyl-N,N-dimethyl-cyclohexanae-1,4-diamime dihydrochloride, nonpolar diastereomer
N'-benzo[b]thiophen-3-ylmethyl-1-benzyl-N,N-dimethyl-cyclohexane-1,4-diamine dihydrochloride, polar diastereomer
N'-[2-(1H-indol-3-yl)-ethyl]-N,N-dimethyl-1-naphthalen-2-yl-cyclohexane-1,4-diamine dihydrochloride, nonpolar diastereomer
N'-[2-(1H-indol-3-yl)-ethyl]-N,N-dimethyl-1-phenyl-cyclohexane-1,4-diamine dihydrochloride, nonpolar diastereomer
N'-[2-(1H-indol-3-yl)-ethyl]-N,N-dimethyl-1-phenyl-cyclohexane-1,4-diamine dihydrochloride, polar diastereomer
N'-[2-(1H-indol-3-yl)-1-methyl-ethyl]-N,N-dimethyl-1-phenyl-cyclohexane-1,4-diamine dihydrochloride, polar diastereomer
Methyl 2-(4-dimethylamino-4-phenyl-cyclohexylamino)-3-(1H-indol-3-yl)-propionate dihydrochloride, nonpolar diastereomer
Methyl 2-(4-dimethylamino-4-phenyl-cyclohexylamino)-3-(1H-indol-3-yl)-propionate dihydrochloride, polar diastereomer
N'-[2-(1H-indol-3-yl)-1-methyl-ethyl]-N,N, -dimethyl-1-naphthalen-2-yl-cyclohexane-1,4-diamine dihydrochloride, nonpolar diastereomer
N'-benzo[1,3]dioxol-5-ylmethyl-N,N-dimethyl-1-phenyl-cyclohexane-1,4-diamine dihydrochloride, cis/trans mixture N'-[2-(6-fluoro-1H-indol-3-yl)-ethyl]-N,N-dimethyl-1-phenyl-cyclohexane-1,4-diamine dihydrochloride, nonpolar diastereomer N'[2-(6-fluoro-1H-indol-3-yl)-ethyl]-N,N-dimethyl-1-phenyl-cyclohexane-1,4-diamine dihydrochloride, polar diastereomer N'-[2-(1H-indol-3-yl)-ethyl]-N,N,N'-trimethyl-1-phenyl-cyclohexane-1,4-diamine dihydrochloride, nonpolar diastereomer N'-[2-(1H-indol-3-yl)-ethyl]-N,N,N'-trimethyl-1-phenyl-cyclohexane-1,4-diamine dihydrochloride, polar diastereomer N,N-dimethyl-N'-[2-(7-methyl-1H-indol-3-yl)-ethyl]-1-phenyl-cyclohexane-1,4-diamine dihydrochloride, nonpolar diastereomer N,N-dimethyl-N'-[2-(7-methyl-1H-indol-3-yl)-ethyl]-1-phenyl-cyclohexane-1,4-diamine dihydrochloride, polar diastereomer N'-[2-(5-fluoro-1H-indol-3-yl)-ethyl]-N,N-dimethyl-1-phenyl-cyclohexane-1,4-diamine dihydrochloride, nonpolar diastereomer N'-[2-(5-fluoro-1H-indol-3-yl)-ethyl]-N,N-dimethyl-1-phenyl-cyclohexane-1,4-diamine dihydrochloride, polar diastereomer N'-acenaphthen-5-ylmethyl-N,N-dimethyl-1-phenyl-cyclohexane-1,4-diamine dihydrochloride, nonpolar diastereomer N'-[2-(1H-indol-3-yl)-1-methyl-ethyl]-N,N-dimethyl-1-thiophen-2-yl-cyclohexane-1,4-diamine dihydrochloride, nonpolar diastereomer N'-[2-(1H-indol-3-yl)-1-methyl-ethyl]-N,N-dimethyl-1-thiophen-2-yl-cyclohexane-1,4-diamine dihydrochloride, cis/trans mixture N'-[2-(7-benzyloxy-1H-indol-3-yl)-ethyl]-N,N-dimethyl-1-phenyl-cyclohexane-1,4-diamine dihydrochloride, nonpolar diastereomer N'-cyclooctyl-N,N-dimethyl-1-thiophen-2-yl-cyclohexane-1,4-diamine dihydrochloride, nonpolar diastereomer N'-adamantan-2-yl-N,N-dimethyl-1-thiophen-2-yl-cyclohexane-1,4-diamine dihydrochloride, nonpolar diastereomer 3-[2-(4-dimethylamino-4-phenyl-cyclohexylamino)-ethyl]-1H-indol-5-ol dihydrochloride, nonpolar diastereomer 3-[2-(4-dimethylamino-4-phenyl-cyclohexylamino)-ethyl]-1H-indol-5-ol dihydrochloride, polar diastereomer N'-[2-(5-methoxy-1H-indol-3-yl)-ethyl]-N,N-dimethyl-1-phenyl-cyclohexane-1,4-diamine dihydrochloride, nonpolar diastereomer N'-[2-(5-methoxy-1H-indol-3-yl)-ethyl]-N,N-dimethyl-1-phenyl-cyclohexane-1,4-diamine dihydrochloride, polar diastereomer N,N-dimethyl-N'-[2-(5-methyl-1H-indol-3-yl)-ethyl]-1-phenyl-cyclohexane-1,4-diamine dihydrochloride, nonpolar diastereomer N,N-dimethyl-N'-[2-(5-methyl-1H-indol-3-yl)-ethyl]-1-phenyl-cyclohexane-1,4-diamine dihydrochloride, polar diastereomer dimethyl-[1-phenyl-4-(1,3,4,9-tetrahydro-b-carbolin-2-yl)-cyclohexyl]-amine dihydrochloride N-(4-dimethylamino-4-phenyl-cyclohexyl)-N-[2-(4-fluoro-phenyl)-ethyl]-acetamide hydrochloride, nonpolar diastereomer 2-(4-dimethylamino-4-phenyl-cyclohexylamino)-3-(5-fluoro-1H-indol-3-yl)-propionic acid methyl ester dihydrochloride, nonpolar diastereomer N-(4-dimethylamino-4-phenyl-cyclohexyl)-N-(3-phenyl-propyl)-acetamide hydrochloride, nonpolar diastereomer 2-(4-dimethylamino-4-phenyl-cyclohexylamino)-3-(6-fluoro-1H-indol-3-yl)-propionic acid methyl ester dihydrochloride, nonpolar diastereomer N-(4-dimethylamino-4-phenyl-cyclohexyl)-2-(1H-indol-3-yl)-acetamide hydrochloride, polar diastereomer 2-(4-dimethylamino-4-thiophen-2-yl-cyclohexylamino)-3-(1H-indol-3-yl)-propionic acid methyl ester dihydrochloride, nonpolar diastereomer N-(4-dimethylamino-4-phenyl-cyclohexyl)-2-(5-methoxy-1H-indol-3-yl)-acetamide hydrochloride, nonpolar diastereomer optionally also in the form of their racemates, of the mentioned or other pure stereoisomers, in particular enantiomers or diastereomers, or in the form of mixtures of the stereoisomers, in particular of the enantiomers or diastereomers, in any mixing ratio;

optionally also in the form of the acids or bases or in the form of other salts, in particular physiologically acceptable salts or salts of physiologically acceptable acids or cations; or in the form of their solvates, in particular the hydrates.

The substances according to the invention are toxicologically acceptable, so that they are suitable as a pharmaceutical active compound in medicaments.

The invention therefore also provides medicaments comprising at least one substituted cyclohexane-1,4-diamine compound from the compound group, called (F) in the following, according to the general formula I

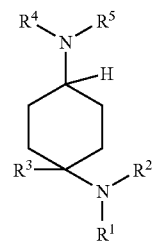

I wherein
R$^1$ and R$^2$ independently of one another are chosen from H; C$_{1-8}$-alkyl or C$_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, C$_{3-8}$-cycloalkyl or heteroaryl, bonded via C$_{1-3}$-alkylene and in each case mono- or polysubstituted or unsubstituted; wherein R$^1$ and R$^2$ may not both be H, or the radicals R$^1$ and R$^2$ together form a ring and denote CH$_2$CH$_2$OCH$_2$CH$_2$, CH$_2$CH$_2$NR$^6$CH$_2$CH$_2$ or (CH$_2$)$_{3-6}$,
where R$^6$ is chosen from H; C$_{1-8}$-alkyl or C$_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, C$_{3-8}$-cycloalkyl or heteroaryl, bonded via C$_{1-3}$-alkylene and in each case mono- or polysubstituted or unsubstituted;

$R^3$ is chosen from $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

$R^4$ is chosen from H, $C_{1-8}$-alkyl, saturated or unsaturated, branched or unbranched, mono- or polysubstituted or unsubstituted; or $C(X)R^7$, $C(X)NR^7R^8$, $C(X)OR^9$, $C(X)SR^9$, $S(O_2)R^9$ where X=O or S, where $R^7$ is chosen from H, $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

where $R^8$ is chosen from H, $C_{1-4}$-alkyl, saturated or unsaturated, branched or unbranched, mono- or polysubstituted or unsubstituted or the radicals $R^7$ and $R^8$ together form a ring and denote $CH_2CH_2OCH_2CH_2$, $CH_2CH_2NR^{10}CH_2CH_2$ or $(CH_2)_{3-6}$, where $R^{10}$ is chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted;

where $R^9$ is chosen from $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

$R^5$ is chosen from $C_{3-8}$-cycloalkyl, aryl or heteroaryl, in each case unsubstituted or mono- or polysubstituted; —$CHR^{11}R^{12}$, —$CHR^{11}$—$CH_2R^{12}$, —$CHR^{11}$—$CH_2$—$CH_2R^{12}$, —$CHR^{11}$—$CH_2$—$CH_2$—$CH_2R^{12}$, —$C(Y)R^{12}$, —$C(Y)$—$CH_2R^{12}$, —$C(Y)$—$CH_2$—$CH_2R^{12}$ or —$C(Y)$—$CH_2$—$CH_2$—$CH_2R^{12}$ where Y=O, S or $H_2$, where $R^{11}$ is chosen from H, $C_{1-7}$-alkyl, saturated or unsaturated, branched or unbranched, mono- or polysubstituted or unsubstituted; or $C(O)O$—$C_{1-6}$-alkyl, saturated or unsaturated, branched or unbranched, mono- or polysubstituted or unsubstituted;

and where $R^{12}$ is chosen from

H; $C_{3-8}$-cycloalkyl, aryl or heteroaryl, in each case unsubstituted or mono- or polysubstituted, or $R^4$ and $R^5$ together form a heterocyclic radical having between 3 and 8 atoms in the ring, saturated or unsaturated; mono- or polysubstituted or unsubstituted, which heterocyclic radical may optionally be fused to further rings, with the proviso, that if $R^3$ is substituted or unsubstituted phenyl and at least one of or $R^2$ is H or $C_{1-8}$-alkyl, $R^4$ may not be alkyl and $R^4$ and $R^5$ may not gether form a heterocyclic radical optionally in the form of its racemate, of the pure stereoisomers, in particular enantiomers or diastereomers, or in the form of mixtures of the stereoisomers, in particular of the enantiomers or diastereomers, in any mixing ratio;

in the prepared form or in the form of its acids or its bases or in the form of its salts, especially the physiologically acceptable salts or salts of physiologically acceptable acids or cations; or in the form of its solvates, in particular the hydrates, and optionally comprising suitable additives and/or auxiliary substances and/or optionally further active compounds.

The invention likewise also provides medicaments comprising at least one substituted cyclohexane-1,4-diamine compound from the compound group, called (G) in the following, according to the general formula I

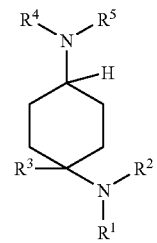

wherein $R^1$ and $R^2$ independently of one another are chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted; wherein $R^1$ and $R^2$ may not both be H, or the radicals $R^1$ and $R^2$ together form a ring and denote $CH_2CH_2OCH_2CH_2$, $CH_2CH_2NR^6CH_2CH_2$ or $(CH_2)_{3-6}$, where $R^6$ is chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted;

$R^3$ is chosen from $C_{1-8}$-alkyl or $C_{3-8}$-cycloalkyl, in each case saturated or unsaturated, branched or unbranched, mono- or polysubstituted or unsubstituted; heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

$R^4$ is chosen from H, $C_{1-8}$-alkyl, saturated or unsaturated, branched or unbranched, mono- or polysubstituted or unsubstituted or C(X)R$^7$, C(X)NR$^7$R$^8$, C(X)OR$^9$, C(X)SR$^9$, S(O$_2$)R$^9$ where X=O or S, where R$^7$ is chosen from H, C$_{1-8}$-alkyl or C$_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, C$_{3-8}$-cycloalkyl or heteroaryl, bonded via a saturated or unsaturated, branched or unbranched, substituted or unsubstituted C$_{1-4}$-alkyl group and in each case unsubstituted or mono- or polysubstituted;

where R$^8$ is chosen from H, C$_{1-4}$-alkyl, saturated or unsaturated, branched or unbranched, mono- or polysubstituted or unsubstituted or the radicals R$^7$ and R$^8$ together form a ring and denote CH$_2$CH$_2$OCH$_2$CH$_2$, CH$_2$CH$_2$NR$^{10}$CH$_2$CH$_2$ or (CH$_2$)$_{3-6}$, where R$^{10}$ is chosen from H; C$_{1-8}$-alkyl or C$_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, C$_{3-8}$-cycloalkyl or heteroaryl, bonded via C$_{1-3}$-alkylene and in each case mono- or polysubstituted or unsubstituted;

where R$^9$ is chosen from C$_{1-8}$-alkyl or C$_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, C$_{3-8}$-cycloalkyl or heteroaryl, bonded via a saturated or unsaturated, branched or unbranched, substituted or unsubstituted C$_{1-4}$-alkyl group and in each case unsubstituted or mono- or polysubstituted;

R$^5$ is chosen from C$_{3-8}$-cycloalkyl, aryl or heteroaryl, in each case unsubstituted or mono- or polysubstituted; —CHR$^{11}$R$^{12}$, —CHR$^{11}$—CH$_2$R$^{12}$, —CHR$^{11}$—CH$_2$—CH$_2$R$^{12}$, —CHR$^{11}$—CH$_2$—CH$_2$—CH$_2$R$^{12}$, —C(Y)R$^{12}$, —C(Y)—CH$_2$R$^{12}$, —C(Y)—CH$_2$—CH$_2$R$^{12}$ or —C(Y)—CH$_2$—CH$_2$—CH$_2$R$^{12}$ where Y=O, S or H$_2$, where R$^{11}$ is chosen from H, C$_{1-7}$-alkyl, saturated or unsaturated, branched or unbranched, mono- or polysubstituted or unsubstituted; or C(O)O—C$_{1-6}$-alkyl, saturated or unsaturated, branched or unbranched, mono- or polysubstituted or unsubstituted;

and where R$^{12}$ is chosen from

H; C$_{3-8}$-cycloalkyl, aryl or heteroaryl, in each case unsubstituted or mono- or polysubstituted, or R$^4$ and R$^5$ together form a heterocyclic radical having between 3 and 8 atoms in the ring, saturated or unsaturated; mono- or polysubstituted or unsubstituted, which heterocyclic radical may optionally be fused to further rings, optionally in the form of its racemate, of the pure stereoisomers, in particular enantiomers or diastereomers, or in the form of mixtures of the stereoisomers, in particular of the enantiomers or diastereomers, in any mixing ratio;

in the prepared form or in the form of its acids or its bases or in the form of its salts, in particular the physiologically acceptable salts or salts of physiologically acceptable acids or cations; or in the form of its solvates, in particular the hydrates, and optionally comprising suitable additives and/or auxiliary substances and/or optionally further active compounds.

The invention likewise also provides medicaments comprising at least one substituted cyclohexane-1,4-diamine compound from the compound group, called (H) in the following, according to the general formula I

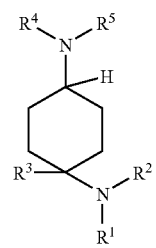

wherein

R$^1$ and R$^2$ together form a ring and denote CH$_2$CH$_2$OCH$_2$CH$_2$, CH$_2$CH$_2$NR$^6$CH$_2$CH$_2$ or (CH$_2$)$_{3-6}$, where R$^6$ is chosen from H; C$_{1-8}$-alkyl or C$_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, C$_{3-8}$-cycloalkyl or heteroaryl, bonded via C$_{1-3}$-alkylene and in each case mono- or polysubstituted or unsubstituted;

R$^3$ is chosen from C$_{1-8}$-alkyl or C$_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, C$_{3-8}$-cycloalkyl or heteroaryl, bonded via a saturated or unsaturated, branched or unbranched, substituted or unsubstituted C$_{1-4}$-alkyl group and in each case unsubstituted or mono- or polysubstituted;

R$^4$ is chosen from H, C$_{1-8}$-alkyl, saturated or unsaturated, branched or unbranched, mono- or polysubstituted or unsubstituted or C(X)R$^7$, C(X)NR$^7$R$^8$, C(X)OR$^9$, C(X)SR$^9$, S(O$_2$)R$^9$ where X=O or S, where R$^7$ is chosen from H, C$_{1-8}$-alkyl or C$_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, C$_{3-8}$-cycloalkyl or heteroaryl, bonded via a saturated or unsaturated, branched or unbranched, substituted or unsubstituted C$_{1-4}$-alkyl group and in each case unsubstituted or mono- or polysubstituted;

where R$^8$ is chosen from H, C$_{1-4}$-alkyl, saturated or unsaturated, branched or unbranched, mono- or polysubstituted or unsubstituted or the radicals R$^7$ and R$^8$ together form a ring and denote CH$_2$CH$_2$OCH$_2$CH$_2$, CH$_2$CH$_2$NR$^{10}$CH$_2$CH$_2$ or (CH$_2$)$_{3-6}$, where R$^{10}$ is chosen from H; C$_{1-8}$-alkyl or C$_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, C$_{3-8}$-cycloalkyl or heteroaryl, bonded via C$_{1-3}$-alkylene and in each case mono- or polysubstituted or unsubstituted;

where R⁹ is chosen from $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

$R^5$ is chosen from $C_{3-8}$-cycloalkyl, aryl or heteroaryl, in each case unsubstituted or mono- or polysubstituted; —CHR¹¹R¹², —CHR¹¹—CH₂R¹², —CHR¹¹—CH₂—CH₂R¹², —CHR¹¹—CH₂—CH₂—CH₂R¹², —C(Y)R¹², —C(Y)—CH₂R¹², —C(Y)—CH₂—CH₂R¹² or —C(Y)—CH₂—CH₂—CH₂R¹² where Y=O, S or H₂, where $R^{11}$ is chosen from
H, $C_{1-7}$-alkyl, saturated or unsaturated, branched or unbranched, mono- or polysubstituted or unsubstituted; or C(O)O—$C_{1-6}$-alkyl, saturated or unsaturated, branched or unbranched, mono- or polysubstituted or unsubstituted;

and where $R^{12}$ is chosen from
H; $C_{3-8}$-cycloalkyl, aryl or heteroaryl, in each case unsubstituted or mono- or polysubstituted, or $R^4$ and $R^5$ together form a heterocyclic radical having between 3 and 8 atoms in the ring, saturated or unsaturated; mono- or polysubstituted or unsubstituted, which heterocyclic radical may optionally be fused to further rings, optionally in the form of its racemate, of the pure stereoisomers, in particular enantiomers or diastereomers, or in the form of mixtures of the stereoisomers, in particular of the enantiomers or diastereomers, in any mixing ratio;

in the prepared form or in the form of its acids or its bases or in the form of its salts, in particular the physiologically acceptable salts or salts of physiologically acceptable acids or cations; or in the form of its solvates, in particular the hydrates, and optionally comprising suitable additives and/or auxiliary substances and/or optionally further active compounds.

The invention likewise also provides medicaments comprising at least one substituted cyclohexane-1,4-diamine compound from the compound group, called (J) in the following, according to the general formula I

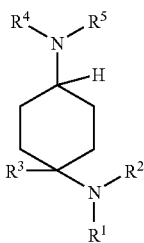

I wherein
$R^1$ and $R^2$ independently of one another are chosen from H; $C_{1-8}$-lkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted; wherein $R^1$ and $R^2$ may not both be H, or the radicals $R^1$ and $R^2$ together form a ring and denote CH₂CH₂OCH₂CH₂, CH₂CH₂NR⁶CH₂CH₂ or (CH₂)₃₋₆, where $R^6$ is chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted;

$R^3$ is chosen from $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

$R^4$ is chosen from H, C(X)R⁷, C(X)NR⁷R⁸, C(X)OR⁹, C(X)SR⁹, S(O₂)R⁹
where X=O or S,
where $R^7$ is chosen from H, $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

where $R^8$ is chosen from H, $C_{1-4}$-alkyl, saturated or unsaturated, branched or unbranched, mono- or polysubstituted or unsubstituted or the radicals $R^7$ and $R^8$ together form a ring and denote CH₂CH₂OCH₂CH₂, CH₂CH₂NR¹⁰CH₂CH₂ or (CH₂)₃₋₆, where $R^{10}$ is chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted;

where $R^9$ is chosen from $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

$R^5$ is chosen from $C_{3-8}$-cycloalkyl, aryl or heteroaryl, in each case unsubstituted or mono- or polysubstituted; —CHR¹¹R¹², —CHR¹¹—CH₂R¹², —CHR¹¹—CH₂—CH₂R¹², —CHR¹¹—CH₂—CH₂—CH₂R¹², —C(Y)R¹², —C(Y)—CH₂R¹², —C(Y)—CH₂—CH₂R¹² or —C(Y)—CH₂—CH₂—CH₂R¹²
where Y=O, S or H₂,
where $R^{11}$ is chosen from H, $C_{1-7}$-alkyl, saturated or unsaturated, branched or unbranched, mono- or polysubstituted or unsubstituted; or $C(O)O$—$C_{1-6}$-alkyl, saturated or unsaturated, branched or unbranched, mono- or polysubstituted or unsubstituted;

and where $R^{12}$ is chosen from

H; $C_{3-8}$-cycloalkyl, aryl or heteroaryl, in each case unsubstituted or mono- or polysubstituted, optionally in the form of its racemate, of the pure stereoisomers, in particular enantiomers or diastereomers, or in the form of mixtures of the stereoisomers, in particular of the enantiomers or diastereomers, in any mixing ratio;

in the prepared form or in the form of its acids or its bases or in the form of its salts, in particular the physiologically acceptable salts or salts of physiologically acceptable acids or cations; or in the form of its solvates, in particular the hydrates, and optionally comprising suitable additives and/or auxiliary substances and/or optionally further active compounds.

Preferred medicaments according to the invention comprise at least one cyclohexane-1,4-diamine compound from one of the compound groups (F) or (G) according to formula I, wherein $R^1$ and $R^2$ independently of one another are chosen from H; $C_{1-8}$-alkyl, saturated or unsaturated, branched or unbranched, mono- or polysubstituted or unsubstituted; wherein $R^1$ and $R^2$ may not both be H, or the radicals $R^1$ and $R^2$ together form a ring and denote $CH_2CH_2OCH_2CH_2$, $CH_2CH_2NR^6CH_2CH_2$ or $(CH_2)_{3-6}$, where $R^6$ is chosen from H; $C_{1-8}$-alkyl, saturated or unsaturated, branched or unbranched, mono- or polysubstituted or unsubstituted, preferably $R^1$ and $R^2$ independently of one another are chosen from H; $C_{1-4}$-alkyl, saturated or unsaturated, branched or unbranched, mono- or polysubstituted or unsubstituted; wherein $R^1$ and $R^2$ may not both be H, or the radicals $R^1$ and $R^2$ together form a ring and denote $(CH_2)_{4-5}$, in particular $R^1$ and $R^2$ independently of one another are chosen from methyl or ethyl or the radicals $R^1$ and $R^2$ together form a ring and denote $(CH_2)_5$.

Preferred medicaments according to the invention comprise at least one cyclohexane-1,4-diamine compound from the compound group (H) according to formula I, wherein $R^1$ and $R^2$ together form a ring and denote $CH_2CH_2OCH_2CH_2$, $CH_2CH_2NR^6CH_2CH_2$ or $(CH_2)_{3-6}$, where $R^6$ is chosen from H; $C_{1-8}$-alkyl, saturated or unsaturated, branched or unbranched, mono- or polysubstituted or unsubstituted, preferably $R^1$ and $R^2$ together form a ring and denote $(CH_2)_{4-5}$, in particular $R^1$ and $R^2$ together form a ring and denote $(CH_2)_5$.

Preferred medicaments according to the invention comprise at least one cyclohexane-1,4-diamine compound from the compound group (J) according to formula I, wherein $R^1$ and $R^2$ independently of one another are chosen from H; $C_{1-8}$-alkyl, saturated or unsaturated, branched or unbranched, mono- or polysubstituted or unsubstituted; wherein $R^1$ and $R^2$ may not both be H, preferably $R^1$ and $R^2$ independently of one another are chosen from H; $C_{1-4}$-alkyl, saturated or unsaturated, branched or unbranched, mono- or polysubstituted or unsubstituted; wherein $R^1$ and $R^2$ may not both be H, in particular $R^1$ and $R^2$ independently of one another are chosen from methyl or ethyl;

or $R^1$ and $R^2$ together form a ring and denote $CH_2CH_2OCH_2CH_2$, $CH_2CH_2NR^6CH_2CH_2$ or $(CH_2)_{3-6}$, where $R^6$ is chosen from H; $C_{1-8}$-alkyl, saturated or unsaturated, branched or unbranched, mono- or polysubstituted or unsubstituted, preferably $R^1$ and $R^2$ together form a ring and denote $(CH_2)_{4-5}$, in particular $R^1$ and $R^2$ together form a ring and denote $(CH_2)_5$.

Preferred medicaments according to the invention comprise at least one cyclohexane-1,4-diamine compound from one of the compound groups (F), (H) or (J) according to formula I, wherein $R^3$ is chosen from $C_{3-8}$-cycloalkyl, aryl or heteroaryl, in each case unsubstituted or mono- or polysubstituted; aryl, $C_{3-8}$-cycloalkyl or heteroaryl, bonded via a saturated or unsaturated, unbranched, substituted or unsubstituted $C_{1-2}$-alkyl group and in each case unsubstituted or mono- or polysubstituted;

preferably $R^3$ is chosen from $C_{5-6}$-cycloalkyl, phenyl, naphthyl, anthracenyl, thiophenyl, benzothiophenyl, furyl, benzofuranyl, benzodioxolanyl, indolyl, indanyl, benzodioxanyl, pyrrolyl, pyrimidyl or pyrazinyl, in each case unsubstituted or mono- or polysubstituted; $C_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl, bonded via a saturated, unbranched $C_{1-2}$-alkyl group and in each unsubstituted or mono- or polysubstituted;

in particular $R^3$ is chosen from phenyl, furyl, thiophenyl, cyclohexanyl, naphthyl, benzofuranyl, indolyl, indanyl, benzodioxanyl, benzodioxolanyl, pyrrolyl, pyrimidyl, pyrazinyl or benzothiophenyl, in each case unsubstituted or mono- or polysubstituted; phenyl, furyl or thiophenyl, bonded via a saturated, unbranched $C_{1-2}$-alkyl group and in each case unsubstituted or mono- or polysubstituted.

Preferred medicaments according to the invention comprise at least one cyclohexane-1,4-diamine compound from the compound group (G) according to formula I, wherein $R^3$ is chosen from $C_{3-8}$-cycloalkyl or heteroaryl, in each case unsubstituted or mono- or polysubstituted; aryl, $C_{3-8}$-cycloalkyl or heteroaryl, bonded via a saturated or unsaturated, unbranched, substituted or unsubstituted $C_{1-4}$-alkyl group and in each case unsubstituted or mono- or polysubstituted;

preferably $R^3$ is chosen from $C_{5-6}$-cycloalkyl, thiophenyl, benzothiophenyl, furyl, benzofuranyl, benzodioxolanyl, indolyl, indanyl, benzodioxanyl, pyrrolyl, pyrimidyl or pyrazinyl, in each case unsubstituted or mono- or polysubstituted; $C_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl, bonded via a saturated, unbranched $C_{1-2}$-alkyl group and in each case unsubstituted or mono- or polysubstituted;

in particular $R^3$ is chosen from furyl, thiophenyl, cyclohexanyl, benzofuranyl, indolyl, indanyl, benzodioxanyl, benzodioxolanyl, pyrrolyl, pyrimidyl, pyrazinyl or benzothiophenyl, in each case unsubstituted or mono- or polysubstituted; phenyl, furyl or thiophenyl, bonded via a saturated, unbranched $C_{1-2}$-alkyl group and in each case unsubstituted or mono- or polysubstituted.

Preferred medicaments according to the invention comprise at least one cyclohexane-1,4-diamine compound from the compound groups (F), (G), (H) or (J) according to formula I, wherein $R^4$ is H.

Preferred medicaments according to the invention comprise at least one cyclohexane-1,4-diamine compound from the compound groups (F), (G), (H) or (J) according to formula I, wherein $R^4$ is chosen from H, $C(X)R^7$, $C(X)NR^7R^8$, $C(X)OR^9$, $C(X)SR^9$ or $S(O_2)R^9$, where X=O or S, preferably $R^4$ is chosen from H, $C(X)R^7$, $C(X)NR^7R^8$ or $C(X)OR^9$, where X=O, in particular $R^4$ is chosen from H or $C(O)R^7$; preferably where $R^7$ is chosen from H; or $C_{1-8}$-alkyl, saturated or unsaturated, branched or unbranched, mono- or polysubstituted or unsubstituted;

preferably

H; or $C_{1-3}$-alkyl, saturated, unsubstituted, branched or unbranched;

in particular $CH_3$.

Further preferred medicaments according to the invention comprise at least one cyclohexane-1,4-diamine compound from the compound groups (F), (G) or (H) according to formula I, wherein $R^4$ and $R^5$ together form a heterocyclic radical having between 3 and 8 atoms in the ring, saturated or unsaturated; mono- or polysubstituted or unsubstituted, preferably having between 5 and 7 atoms in the ring, of which, in addition to the obligatory N, 0 to 1 further heteroatoms chosen from N, S or O are in the ring;

wherein the heterocyclic radical formed by $R^4$ and $R^5$ together may optionally be fused to further rings, preferably to aromatic and/or heteroaromatic rings, wherein those rings can be fused to further aromatic and/or heteroaromatic rings, in particular the heterocyclic radical formed by $R^4$ and $R^5$ together is fused to one or two further rings, preferably the heterocyclic radical formed by $R^4$ and $R^5$ together is so fused to two further rings that $R^4$ and $R^5$ together denote

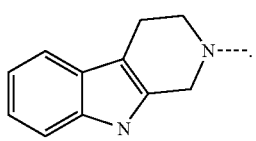

Preferred medicaments according to the invention comprise at least one cyclohexane-1,4-diamine compound from the compound groups (F), (G) or (H) according to formula I, wherein $R^4$ is chosen from H, $C_{1-8}$-alkyl, saturated or unsaturated, branched or unbranched, mono- or polysubstituted or unsubstituted, preferably H, $C_{1-6}$-alkyl, saturated or unsaturated, branched or unbranched, mono- or polysubstituted or unsubstituted, in particular H, $C_{1-3}$-alkyl, saturated, unbranched and unsubstituted.

Preferred medicaments according to the invention comprise at least one cyclohexane-1,4-diamine compound from the compound groups (F), (G), (H) or (J) according to formula I, wherein $R^5$ is chosen from $C_{3-8}$-cycloalkyl, aryl or heteroaryl, in each case unsubstituted or mono- or polysubstituted;

preferably $R^5$ is chosen from cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, in each case unsubstituted or mono- or polysubstituted;

in particular $R^5$ is chosen from cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, in each case unsubstituted or mono- or polysubstituted.

Medicaments according to the invention which are likewise preferred comprise at least one cyclohexane-1,4-diamine compound from the compound groups (F), (G), (H) or (J) according to formula I, wherein $R^5$ is chosen from $—CHR^{11}R^{12}$, $—CHR^{11}—CH_2R^{12}$, $—CHR^{11}—CH_2—CH_2R^{12}$, $—CHR^{11}—CH_2—CH_2—CH_2R^{12}$, $—C(Y)R^{12}$, $—C(Y)—CH_2R^{12}$, $—C(Y)—CH^2—CH_2R^{12}$ or $—C(Y)—CH_2—CH_2—CH_2R^{12}$ where Y=O, S or $H_2$, preferably $R^5$ is chosen from $—CHR^{11}R^{12}$, $—CHR^{11}—CH_2R^{12}$, $—CHR^{11}—CH_2—CH_2R^{12}$, $—C(Y)R^{12}$, $—C(Y)—CH^2R^{12}$ or $—C(Y)—CH_2—CH_2R^{12}$ where Y=O or S, in particular $R^5$ is chosen from $—CHR^{11}R^{12}$, $—CHR^{11}—CH_2R^{12}$, $—CHR^{11}—CH_2—CH_2R^{12}$, $—C(Y)R^{12}$ or $—C(Y)—CH_2R^{12}$ where Y=O.

In respect of the last group of preferred medicaments, it is particularly preferable here if $R^{11}$ is chosen from H, $C_{1-4}$-alkyl, saturated or unsaturated, branched or unbranched, mono- or polysubstituted or unsubstituted; or $C(O)O$—$C_{1-4}$-alkyl, saturated or unsaturated, branched or unbranched, mono- or polysubstituted or unsubstituted;

preferably

H, $C_{1-4}$-alkyl, saturated or unsaturated, branched or unbranched, mono- or polysubstituted or unsubsti tuted; or C(O)O—C$_{1-2}$-alkyl, saturated, unbranched, mono- or polysubstituted or unsubstituted;
in particular
H, CH$_3$, C$_2$H$_5$ and C(O)O—CH$_3$, and/or if R$^{12}$ is chosen from C$_{3-8}$-cycloalkyl, aryl or heteroaryl, in each case unsubstituted or mono- or polysubstituted; preferably R$^{12}$ is chosen from cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, in each case unsubstituted or mono- or polysubstituted;

in particular

R$^{12}$ is chosen from cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, in each case unsubstituted or mono- or polysubstituted.

In addition to at least one substituted cyclohexane-1,4-diamine compound according to the invention, the medicaments according to the invention optionally comprise suitable additives and/or auxiliary substances, that is to say also carrier materials, fillers, solvents, diluents, dyestuffs and/or binders, and can be administered as liquid medicament forms in the form of injection solutions, drops or juices, as semi-solid medicament forms in the form of granules, tablets, pellets, patches, capsules, plasters or aerosols. The choice of the auxiliary substances etc. and the amounts thereof to be employed depend on whether the medicament is to be administered orally, perorally, parenterally, intravenously, intraperitoneally, intradermally, intramuscularly, intranasally, buccally, rectally or locally, for example to the skin, the mucous membranes or in the eyes. Formulations in the form of tablets, coated tablets, capsules, granules, drops, juices and syrups are suitable for oral administration, solutions, suspensions, easily reconstitutable dry formulations and sprays are suitable for parenteral, topical and inhalatory administration. Substituted cyclohexane-1,4-diamine compounds according to the invention in a depot, in dissolved form or in a plaster, optionally with the addition of agents which promote penetration through the skin, are suitable formulations for percutaneous administration. Formulation forms which can be used orally or percutaneously can release the substituted cyclohexane-1,4-diamine compounds according to the invention in a delayed manner. Other further active compounds known to the expert can in principle be added to the medicaments according to the invention.

The amount of active compound to be administered to the patients varies according to the weight of the patient, the mode of administration, the indication and the severity of the disease. 0.005 to 1,000 mg/kg, preferably 0.05 to 5 mg/kg of at least one substituted cyclohexane-1,4-diamine compound according to the invention are conventionally administered.

For all the above forms of the medicaments according to the invention, it is particularly preferable if, in addition to at least one substituted cyclohexane-1,4-diamine compound, the medicament also comprises an opioid, preferably a potent opioid, in particular morphine, or an anaesthetic, preferably hexobarbital or halothane.

In a preferred form of the medicament, a substituted cyclohexane-1,4-diamine compound according to the invention contained therein is present as the pure diastereomer and/or enantiomer, as a racemate or as a non-equimolar or equimolar mixture of the diastereomers and/or enantiomers.

As can be seen in the introduction from the prior art, the ORL1 receptor has been identified in particular in the pain event. Substituted cyclohexane-1,4-diamine compounds according to the invention can accordingly be used for the preparation of a medicament for treatment of pain, and for the treatment thereof, in particular acute, neuropathic or chronic pain.

The invention therefore also provides the use of substituted cyclohexane-1,4-diamine compounds, called compound group (K) in the following, according to the general formula I

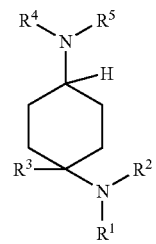

wherein

R$^1$ and R$^2$ independently of one another are chosen from H; C$_{1-8}$-alkyl or C$_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, C$_{3-8}$-cycloalkyl or heteroaryl, bonded via C$_{1-3}$-alkylene and in each case mono- or polysubstituted or unsubstituted; wherein R$^1$ and R$^2$ may not both be H, or the radicals R$^1$ and R$^2$ together form a ring and denote CH$_2$CH$_2$OCH$_2$CH$_2$, CH$_2$CH$_2$NR$^6$CH$_2$CH$_2$ or (CH$_2$)$_{3-6}$, where R$^6$ is chosen from H; C$_{1-8}$-alkyl or C$_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, C$_{3-8}$-cycloalkyl or heteroaryl, bonded via C$_{1-3}$-alkylene and in each case mono- or polysubstituted or unsubstituted;

R$^3$ is chosen from C$_{1-8}$-alkyl or C$_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, C$_{3-8}$-cycloalkyl or heteroaryl, bonded via a saturated or unsaturated, branched or unbranched, substituted or unsubstituted C$_{1-4}$-alkyl group and in each case unsubstituted or mono- or polysubstituted;

R$^4$ is chosen from H, C$_{1-8}$-alkyl, saturated or unsaturated, branched or unbranched, mono- or polysubstituted or unsubstituted or C(X)R$^7$, C(X)NR$^7$R$^8$, C(X)OR$^9$, C(X)SR$^9$, S(O$_2$)R$^9$ where X=O or S, where $R^7$ is chosen from H, $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

where $R^8$ is chosen from H, $C_{1-4}$-alkyl, saturated or unsaturated, branched or unbranched, mono- or polysubstituted or unsubstituted or the radicals $R^7$ and $R^8$ together form a ring and denote $CH_2CH_2OCH_2CH_2$, $CH_2CH_2NR^{10}CH_2CH_2$ or $(CH_2)_{3-6}$, where $R^{10}$ is chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted;

where $R^9$ is chosen from $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

$R^5$ is chosen from $C_{3-8}$-cycloalkyl, aryl or heteroaryl, in each case unsubstituted or mono- or polysubstituted; —$CHR^{11}R^{12}$, —$CHR^{11}$—$CH_2R^{12}$, —$CHR^{11}$—$CH_2$—$CH_2R^{12}$, —$CHR^{11}$—$CH_2$—$CH_2$—$CH_2R^{12}$, —$C(Y)R^{12}$, —$C(Y)$—$CH_2R^{12}$, —$C(Y)$—$CH_2$—$CH_2R^{12}$ or —$C(Y)$—$CH_2$—$CH_2$—$CH_2R^{12}$ where Y=O, S or $H_2$, where $R^{11}$ is chosen from H, $C_{1-7}$-alkyl, saturated or unsaturated, branched or unbranched, mono- or polysubstituted or unsubstituted; or C(O)O—$C_{1-6}$-alkyl, saturated or unsaturated, branched or unbranched, mono- or polysubstituted or unsubstituted;

and where $R^{12}$ is chosen from

H; $C_{3-8}$-cycloalkyl, aryl or heteroaryl, in each case unsubstituted or mono- or polysubstituted, or $R^4$ and $R^5$ together form a heterocyclic radical having between 3 and 8 atoms in the ring, saturated or unsaturated; mono- or polysubstituted or unsubstituted, which heterocyclic radical may optionally be fused to further rings, with the proviso, that if $R^3$ is substituted or unsubstituted phenyl and at least one of $R^1$ or $R^2$ is H or $C_{1-8}$-alkyl, $R^4$ may not be alkyl and $R^4$ and $R^5$ may not together form a heterocyclic radical optionally in the form of their racemates, of their pure stereoisomers, in particular enantiomers or diastereomers, or in the form of mixtures of the stereoisomers, in particular of the enantiomers or diastereomers, in any mixing ratio;

in the prepared form or in the form of their acids or their bases or in the form of their salts, in particular the physiologically acceptable salts or salts of physiologically acceptable acids or cations; or in the form of their solvates, in particular the hydrates; for the preparation of a medicament for treatment of pain, in particular acute, neuropathic or chronic pain.

The invention therefore also provides the use of substituted cyclohexane-1,4-diamine compounds, called compound group (L) in the following, according to the general formula I

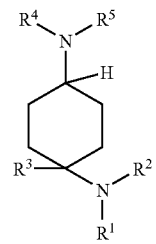

I wherein $R^1$ and $R^2$ independently of one another are chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted; wherein $R^1$ and $R^2$ may not both be H, or the radicals $R^1$ and $R^2$ together form a ring and denote $CH_2CH_2OCH_2CH_2$, $CH_2CH_2NR^6CH_2CH_2$ or $(CH_2)_{3-6}$, where $R^6$ is chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted;

$R^3$ is chosen from $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

$R^4$ is chosen from H, $C_{1-8}$-alkyl, saturated or unsaturated, branched or unbranched, mono- or polysubstituted or unsubstituted or $C(X)R^7$, $C(X)NR^7R^8$, $C(X)OR^9$, $C(X)SR^9$, $S(O_2)R^9$ where X=O or S, where $R^7$ is chosen from H, $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

where $R^8$ is chosen from H, $C_{1-4}$-alkyl, saturated or unsaturated, branched or unbranched, mono- or polysubstituted or unsubstituted or the radicals $R^7$ and $R^8$ together form a ring and denote $CH_2CH_2OCH_2CH_2$, $CH_2CH_2NR^{10}CH_2CH_2$ or $(CH_2)_{3-6}$, where $R^{10}$ is chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted;

where $R^9$ is chosen from $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

$R^5$ is chosen from $C_{3-8}$-cycloalkyl, aryl or heteroaryl, in each case unsubstituted or mono- or polysubstituted; —$CHR^{11}R^{12}$, —$CHR^{11}$—$CH_2R^{12}$, —$CHR^{11}$—$CH_2$—$CH_2R^{12}$, —$CHR^{11}$—$CH_2$—$CH_2$—$CH_2R^{12}$, —$C(Y)R^{12}$, —$C(Y)$—$CH_2R^{12}$, —$C(Y)$—$CH_2$—$CH_2R^{12}$ or —$C(Y)$—$CH_2$—$CH_2$—$CH_2R^{12}$ where $Y=O$, S or $H_2$, where $R^{11}$ is chosen from H, $C_{1-7}$-alkyl, saturated or unsaturated, branched or unbranched, mono- or polysubstituted or unsubstituted; or $C(O)O$—$C_{1-6}$-alkyl, saturated or unsaturated, branched or unbranched, mono- or polysubstituted or unsubstituted;

and where $R^{12}$ is chosen from

H; $C_{3-8}$-cycloalkyl, aryl or heteroaryl, in each case unsubstituted or mono- or polysubstituted, or $R^4$ and $R^5$ together form a heterocyclic radical having between 3 and 8 atoms in the ring, saturated or unsaturated; mono- or polysubstituted or unsubstituted, which heterocyclic radical may optionally be fused to further rings, optionally in the form of their racemates, of their pure stereoisomers, in particular enantiomers or diastereomers, or in the form of mixtures of the stereoisomers, in particular of the enantiomers or diastereomers, in any mixing ratio;

in the prepared form or in the form of their acids or their bases or in the form of their salts, in particular the physiologically acceptable salts or salts of physiologically acceptable acids or cations; or in the form of their solvates, in particular the hydrates; for the preparation of a medicament for treatment of pain, in particular acute, neuropathic or chronic pain.

The invention therefore also provides the use of substituted cyclohexane-1,4-diamine compounds, called compound group (M) in the following, according to the general formula I

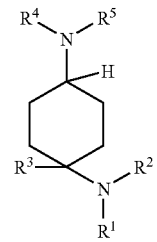

wherein $R^1$ and $R^2$ together form a ring and denote $CH_2CH_2OCH_2CH_2$, $CH_2CH_2NR^6CH_2CH_2$ or $(CH_2)_{3-6}$, where $R^6$ is chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted;

$R^3$ is chosen from $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

$R^4$ is chosen from H, $C_{1-8}$-alkyl, saturated or unsaturated, branched or unbranched, mono- or polysubstituted or unsubstituted or $C(X)R^7$, $C(X)NR^7R^8$, $C(X)OR^9$, $C(X)SR^9$, $S(O_2)R^9$ where $X=O$ or S, where $R^7$ is chosen from H, $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

where $R^8$ is chosen from H, $C_{1-4}$-alkyl, saturated or unsaturated, branched or unbranched, mono- or polysubstituted or unsubstituted or the radicals $R^7$ and $R^8$ together form a ring and denote $CH_2CH_2OCH_2CH_2$, $CH_2CH_2NR^{10}CH_2CH_2$ or $(CH_2)_{3-6}$, where $R^{10}$ is chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted;

where $R^9$ is chosen from $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

$R^5$ is chosen from $C_{3-8}$-cycloalkyl, aryl or heteroaryl, in each case unsubstituted or mono- or polysubstituted; —$CHR^{11}R^{12}$, —$CHR^{11}$—$CH_2R^{12}$, —$CHR^{11}$—$CH_2$—$CH_2R^{12}$, —$CHR^{11}$—$CH_2$—$CH_2$—$CH_2R^{12}$, —$C(Y)R^{12}$, —$C(Y)$—$CH_2R^{12}$, —$C(Y)$—$CH_2$—$CH_2R^{12}$ or —$C(Y)$—$CH_2$—$CH_2$—$CH_2R^{12}$ where Y=O, S or $H_2$, where $R^{11}$ is chosen from H, $C_{1-7}$-alkyl, saturated or unsaturated, branched or unbranched, mono- or polysubstituted or unsubstituted; or C(O)O—$C_{1-6}$-alkyl, saturated or unsaturated, branched or unbranched, mono- or polysubstituted or unsubstituted;

and where $R^{12}$ is chosen from

H; $C_{3-8}$-cycloalkyl, aryl or heteroaryl, in each case unsubstituted or mono- or polysubstituted, or $R^4$ and $R^5$ together form a heterocyclic radical having between 3 and 8 atoms in the ring, saturated or unsaturated; mono- or polysubstituted or unsubstituted, which heterocyclic radical may optionally be fused to further rings, optionally in the form of their racemates, of their pure stereoisomers, in particular enantiomers or diastereomers, or in the form of mixtures of the stereoisomers, in particular of the enantiomers or diastereomers, in any mixing ratio;

in the prepared form or in the form of their acids or their bases or in the form of their salts, in particular the physiologically acceptable salts or salts of physiologically acceptable acids or cations; or in the form of their solvates, in particular the hydrates; for the preparation of a medicament for treatment of pain, in particular acute, neuropathic or chronic pain.

The invention therefore also provides the use of substituted cyclohexane-1,4-diamine compounds, called compound group (N) in the following, according to the general formula I

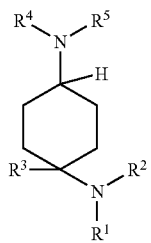

I wherein $R^1$ and $R^2$ independently of one another are chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted; wherein $R^1$ and $R^2$ may not both be H, or the radicals $R^1$ and $R^2$ together form a ring and denote $CH_2CH_2OCH_2CH_2$, $CH_2CH_2NR^6CH_2CH_2$ or $(CH_2)_{3-6}$, where $R^6$ is chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted;

$R^3$ is chosen from $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

$R^4$ is chosen from H, $C(X)R^7$, $C(X)NR^7R^8$, $C(X)OR^9$, $C(X)SR^9$ or $S(O_2)R^9$ where X=O or S, where $R^7$ is chosen from H, $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

where $R^8$ is chosen from H, $C_{1-4}$-alkyl, saturated or unsaturated, branched or unbranched, mono- or polysubstituted or unsubstituted or the radicals $R^7$ and $R^8$ together form a ring and denote $CH_2CH_2OCH_2CH_2$, $CH_2CH_2NR^{10}CH_2CH_2$ or $(CH_2)_{3-6}$, where $R^{10}$ is chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted;

where $R^9$ is chosen from $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

$R^5$ is chosen from $C_{3-8}$-cycloalkyl, aryl or heteroaryl, in each case unsubstituted or mono- or polysubstituted; —$CHR^{11}R^{12}$, —$CHR^{11}$—$CH_2R^{12}$, —$CHR^{11}$—$CH_2$—$CH_2R^{12}$, —$CHR^{11}$—$CH_2$—$CH_2$—$CH_2R^{12}$, —$C(Y)R^{12}$, —$C(Y)$—$CH_2R^{12}$, —$C(Y)$—$CH_2$—$CH_2R^{12}$ or —$C(Y)$—$CH_2$—$CH_2$—$CH_2R^{12}$ where Y=O, S or $H_2$, where $R^{11}$ is chosen from H, $C_{1-7}$-alkyl, saturated or unsaturated, branched or unbranched, mono- or polysubstituted or unsubstituted; or C(O)O—$C_{1-6}$-alkyl, saturated or unsaturated, branched or unbranched, mono- or polysubstituted or unsubstituted;

and where $R^{12}$ is chosen from

H; $C_{3-8}$-cycloalkyl, aryl or heteroaryl, in each case unsubstituted or mono- or polysubstituted, optionally in the form of their racemates, of their pure stereoisomers, in particular enantiomers or diastereomers, or in the form of mixtures of the stereoisomers, in particular of the enantiomers or diastereomers, in any mixing ratio;

in the prepared form or in the form of their acids or their bases or in the form of their salts, in particular the physiologically acceptable salts or salts of physiologically acceptable acids or cations; or in the form of their solvates, in particular the hydrates; for the preparation of a medicament for treatment of pain, in particular acute, neuropathic or chronic pain.

As already stated in the introduction, in addition to the function in the pain event, the ORL1 receptor also plays a role in a large number of other physiological processes, in particular of medically relevant importance, so that the invention also provides the use of substituted cyclohexane-1,4-diamine compounds, called compound group (O) in the following, according to the general formula I

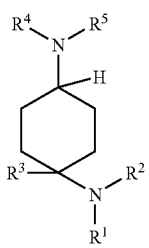

I wherein $R^1$ and $R^2$ independently of one another are chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted; wherein $R^1$ and $R^2$ may not both be H, or the radicals $R^1$ and $R^2$ together form a ring and denote $CH_2CH_2OCH_2CH_2$, $CH_2CH_2NR^6CH_2CH_2$ or $(CH_2)_{3-6}$, where $R^6$ is chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted;

$R^3$ is chosen from $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

$R^4$ is chosen from H, $C_{1-8}$-alkyl, saturated or unsaturated, branched or unbranched, mono- or polysubstituted or unsubstituted or $C(X)R^7$, $C(X)NR^7R^8$, $C(X)OR^9$, $C(X)SR^9$, $S(O_2)R^9$ where X=O or S, where $R^7$ is chosen from H, $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

where $R^8$ is chosen from H, $C_{1-4}$-alkyl, saturated or unsaturated, branched or unbranched, mono- or polysubstituted or unsubstituted or the radicals $R^7$ and $R^8$ together form a ring and denote $CH_2CH_2OCH_2CH_2$, $CH_2CH_2NR^{10}CH_2CH_2$ or $(CH_2)_{3-6}$, where $R^{10}$ is chosen from H; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted;

where $R^9$ is chosen from $C_{1-8}$-alkyl or $C_{3-8}$-cycloalkyl, in each case saturated or unsaturated, branched or unbranched, mono- or polysubstituted or unsubstituted; aryl, heteroaryl, in each case unsubstituted or mono- or polysubstituted; aryl, $C_{3-8}$-cycloalkyl or heteroaryl, bonded via a saturated or unsaturated, branched or unbranched, substituted or unsubstituted $C_{1-4}$-alkyl group and in each case unsubstituted or mono- or polysubstituted;

$R^5$ is chosen from $C_{3-8}$-cycloalkyl, aryl or heteroaryl, in each case unsubstituted or mono- or polysubstituted; —$CHR^{11}R^{12}$, —$CHR^{11}$—$CH_2R^{12}$, —$CHR^{11}$—$CH_2$—$CH_2R^{12}$, —$CHR^{11}$—$CH_2$—$CH_2$—$CH_2R^{12}$, —C(Y)R^2$, —$C(Y)$—$CH_2R^{12}$, —$C(Y)$—$CH_2$—$CH_2R^{12}$ or —$C(Y)$—$CH_2$—$CH_2$—$CH_2R^{12}$ where Y=O, S or $H_2$, where $R^{11}$ is chosen from H, $C_{1-7}$-alkyl, saturated or unsaturated, branched or unbranched, mono- or polysubstituted or unsubstituted; or $C(O)O$—$C_{1-6}$-alkyl, saturated or unsaturated, branched or unbranched, mono- or polysubstituted or unsubstituted;

and where $R^{12}$ is chosen from

H; $C_{3-8}$-cycloalkyl, aryl or heteroaryl, in each case unsubstituted or mono- or polysubstituted, or $R^4$ and $R^5$ together form a heterocyclic radical having between 3 and 8 atoms in the ring, saturated or unsaturated; mono- or polysubstituted or unsubstituted, which heterocyclic radical may optionally be fused to further rings, optionally in the form of their racemates, of their pure stereoisomers, in particular enantiomers or diastereomers, or in the form of mixtures of the stereoisomers, in particular of the enantiomers or diastereomers, in any mixing ratio;

in the prepared form or in the form of their acids or their bases or in the form of their salts, in particular the physiologically acceptable salts or salts of physiologically acceptable acids or cations; or in the form of their solvates, in particular the hydrates; for the preparation of a medicament for treatment of anxiety states, of stress and stress-associated syndromes, depression, epilepsy, Alzheimer's disease, senile dementia, general cognitive dysfunctions, learning and memory difficulties (as a nootropic), withdrawal symptoms, alcohol and/or drug and/or medicament abuse and/or dependency, sexual dysfunctions, cardiovascular diseases, hypotension, hypertension, tinnitus, pruritus, migraine, impaired hearing, deficient intestinal motility, impaired food intake, anorexia, obesity, locomotor disorders, diarrhoea, cachexia, urinary incontinence or as a muscle relaxant, anticonvulsive or anaesthetic or for co-administration in treatment with an opioid analgesic or with an anaesthetic, for diuresis or antinatriuresis and/or anxiolysis.

In one of the above uses, it may be preferable if a substituted cyclohexane-1,4-diamine compound used is in the form of the pure diastereomer and/or enantiomer, as a racemate or as a non-equimolar or equimolar mixture of the diastereomers and/or enantiomers.

In one of the above uses of a substituted cyclohexane-1, 4-diamine compound from one of the compound groups (K), (L) or (O), it may be preferable if, in formula I, $R^1$ and $R^2$ independently of one another are chosen from H; $C_{1-8}$-alkyl, saturated or unsaturated, branched or unbranched, mono- or polysubstituted or unsubstituted; wherein $R^1$ and $R^2$ may not both be H,
or the radicals $R^1$ and $R^2$ together form a ring and denote $CH_2CH_2OCH_2CH_2$, $CH_2CH_2NR^6CH_2CH_2$ or $(CH_2)_{3-6}$,
where $R^6$ is chosen from H; $C_{1-8}$-alkyl, saturated or unsaturated, branched or unbranched, mono- or polysubstituted or unsubstituted,
preferably
$R^1$ and $R^2$ independently of one another are chosen from H; $C_{1-4}$-alkyl, saturated or unsaturated, branched or unbranched, mono- or polysubstituted or unsubstituted; wherein $R^1$ and $R^2$ may not both be H,
or the radicals $R^1$ and $R^2$ together form a ring and denote $(CH_2)_{4-5}$,
in particular
$R^1$ and $R^2$ independently of one another are chosen from methyl or ethyl or the radicals $R^1$ and $R^2$ together form a ring and denote $(CH_2)_5$.

In one of the above uses of a substituted cyclohexane-1, 4-diamine compound from the compound group (M), it may be preferable if, in formula I,
$R^1$ and $R^2$ together form a ring and denote $CH_2CH_2OCH_2CH_2$, $CH_2CH_2NR^6CH_2CH_2$ or $(CH_2)_{3-6}$,
where $R^6$ is chosen from H; $C_{1-8}$-alkyl, saturated or unsaturated, branched or unbranched, mono- or polysubstituted or unsubstituted,
preferably
$R^1$ and $R^2$ together form a ring and denote $(CH_2)_{4-5}$,
in particular
$R^1$ and $R^2$ together form a ring and denote $(CH_2)_5$.

In one of the above uses of a substituted cyclohexane-1, 4-diamine compound from the compound group (N), it may be preferable if, in formula I,
$R^1$ and $R^2$ independently of one another are chosen from H; $C_{1-8}$-alkyl, saturated or unsaturated, branched or unbranched, mono- or polysubstituted or unsubstituted; wherein $R^1$ and $R^2$ may not both be H,
preferably
$R^1$ and $R^2$ independently of one another are chosen from H; $C_{1-4}$-alkyl, saturated or unsaturated, branched or unbranched, mono- or polysubstituted or unsubstituted; wherein $R^1$ and $R^2$ may not both be H,
in particular $R^1$ and $R^2$ independently of one another are chosen from methyl or ethyl;
or
$R^1$ and $R^2$ together form a ring and denote $CH_2CH_2OCH_2CH_2$, $CH_2CH_2NR^6CH_2CH_2$ or $(CH_2)_{3-6}$,
where $R^6$ is chosen from H; $C_{1-8}$-alkyl, saturated or unsaturated, branched or unbranched, mono- or polysubstituted or unsubstituted,
preferably
$R^1$ and $R^2$ together form a ring and denote $(CH_2)_{4-5}$,
in particular
$R^1$ and $R^2$ together form a ring and denote $(CH_2)_5$.

In one of the above uses of a substituted cyclohexane-1, 4-diamine compound from one of the compound groups (K), (M), (N) or (O), it may be preferable if, in formula I,
$R^3$ is chosen from $C_{3-8}$-cycloalkyl, aryl or heteroaryl, in each case unsubstituted or mono- or polysubstituted; aryl, $C_{3-8}$-cycloalkyl or heteroaryl, bonded via a saturated or unsaturated, unbranched, substituted or unsubstituted $C_{1-2}$-alkyl group and in each case unsubstituted or mono- or polysubstituted;
preferably
$R^3$ is chosen from $C_{5-6}$-cycloalkyl, phenyl, naphthyl, anthracenyl, thiophenyl, benzothiophenyl, furyl, benzofuranyl, benzodioxolanyl, indolyl, indanyl, benzodioxanyl, pyrrolyl, pyrimidyl or pyrazinyl, in each case unsubstituted or mono- or polysubstituted; $C_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl, bonded via a saturated, unbranched $C_{1-2}$-alkyl group and in each unsubstituted or mono- or polysubstituted;
in particular
$R^3$ is chosen from phenyl, furyl, thiophenyl, cyclohexanyl, naphthyl, benzofuranyl, indolyl, indanyl, benzodioxanyl, benzodioxolanyl, pyrrolyl, pyrimidyl, pyrazinyl or benzothiophenyl, in each case unsubstituted or mono- or polysubstituted; phenyl, furyl or thiophenyl, bonded via a saturated, unbranched $C_{1-2}$-alkyl group and in each case unsubstituted or mono- or polysubstituted.

In one of the above uses of a substituted cyclohexane-1, 4-diamine compound from the compound group (L), it may be preferable if, in formula I,
$R^3$ is chosen from $C_{3-8}$-cycloalkyl or heteroaryl, in each case unsubstituted or mono- or polysubstituted; aryl, $C_{3-8}$-cycloalkyl or heteroaryl, bonded via a saturated or unsaturated, unbranched, substituted or unsubstituted $C_{1-4}$-alkyl group and in each case unsubstituted or mono- or polysubstituted;
preferably
$R^3$ is chosen from $C_{5-6}$-cycloalkyl, thiophenyl, benzothiophenyl, furyl, benzofuranyl, benzodioxolanyl, indolyl, indanyl, benzodioxanyl, pyrrolyl, pyrimidyl or pyrazinyl, in each case unsubstituted or mono- or polysubstituted; $C_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl, bonded via a saturated, unbranched $C_{1-2}$-alkyl group and in each case unsubstituted or mono- or polysubstituted;
in particular
$R^3$ is chosen from furyl, thiophenyl, cyclohexanyl, benzofuranyl, indolyl, indanyl, benzodioxanyl, benzodioxolanyl, pyrrolyl, pyrimidyl, pyrazinyl or benzothiophenyl, in each case unsubstituted or mono- or polysubstituted; phenyl, furyl or thiophenyl, bonded via a saturated, unbranched $C_{1-2}$-alkyl group and in each case unsubstituted or mono- or polysubstituted.

In one of the above uses of a substituted cyclohexane-1,4-diamine compound from one of the compound groups (K), (L), (M), (N) or (O), it may be preferable if, in formula I, $R^4$ is H.

It may likewise be preferable in one of the above uses of a substituted cyclohexane-1,4-diamine compound from one of the compound groups (K), (L), (M), (N) or (O), it may be preferable if, in formula I, $R^4$ is chosen from H, $C(X)R^7$, $C(X)NR^7R^8$, $C(X)OR^9$, $C(X)SR^9$ or $S(O_2)R^9$, where X=O or S, preferably $R^4$ is chosen from H, $C(X)R^7$, $C(X)NR^7R^8$ or $C(X)OR^9$, where X=O, in particular $R^4$ is chosen from H or $C(O)R^7$; preferably where $R^7$ is chosen from H; or $C_{1-8}$-alkyl, saturated or unsaturated, branched or unbranched, mono- or polysubstituted or unsubstituted;

preferably

H; or $C_{1-3}$-alkyl, saturated, unsubstituted, branched or unbranched;

in particular $CH_3$.

In one of the above uses of a substituted cyclohexane-1,4-diamine compound from one of the compound groups (K), (L), (M) or (O), it may be preferable if, in formula I, $R^4$ and $R^5$ together form a heterocyclic radical having between 3 and 8 atoms in the ring, saturated or unsaturated; mono- or polysubstituted or unsubstituted, preferably having between 5 and 7 atoms in the ring, of which, in addition to the obligatory N, 0 to 1 further heteroatoms chosen from N, S or O are in the ring;

wherein the heterocyclic radical formed by $R^4$ and $R^5$ together may optionally be fused to further rings, preferably to aromatic and/or heteroaromatic rings, wherein those rings can be fused to further aromatic and/or heteroaromatic rings, in particular the heterocyclic radical formed by $R^4$ and $R^5$ together is fused to one or two further rings, preferably the heterocyclic radical formed by $R^4$ and $R^5$ together is so fused to two further rings that $R^4$ and $R^5$ together denote

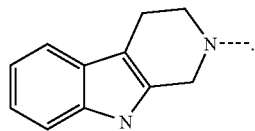

In one of the above uses of a substituted cyclohexane-1,4-diamine compound from one of the compound groups (K), (L), (M) or (O), it may be preferable if, in formula I, $R^4$ is chosen from H, $C_{1-8}$-alkyl, saturated or unsaturated, branched or unbranched, mono- or polysubstituted or unsubstituted, preferably H, $C_{1-6}$-alkyl, saturated or unsaturated, branched or unbranched, mono- or polysubstituted or unsubstituted, in particular H, $C_{1-3}$-alkyl, saturated, unbranched and unsubstituted.

In one of the above uses of a substituted cyclohexane-1,4-diamine compound from one of the compound groups (K), (L), (M), (N) or (O), it may be preferable if, in formula I, $R^5$ is chosen from $C_{3-8}$-cycloalkyl, aryl or heteroaryl, in each case unsubstituted or mono- or polysubstituted;

preferably $R^5$ is chosen from cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, in each case unsubstituted or mono- or polysubstituted;

in particular $R^5$ is chosen from cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, in each case unsubstituted or mono- or polysubstituted.

It may likewise be preferable in one of the above uses of a substituted cyclohexane-1,4-diamine compound from one of the compound groups (K), (L), (M), (N) or (O) if, in formula I, $R^5$ is chosen from $-CHR^{11}R^{12}$, $-CHR^{11}-CH_2R^{12}$, $-CHR^{11}-CH_2-CH_2R^{12}$, $-CHR^{11}-CH_2-CH_2-CH_2R^{12}$, $-C(Y)R^{12}$, $-C(Y)-CH_2R^{12}$, $-C(Y)-CH_2-CH_2R^{12}$ or $-C(Y)-CH_2-CH_2-CH_2R^{12}$ where Y=O, S or $H_2$, preferably $R^5$ is chosen from $-CHR^{11}R^{12}$, $-CHR^{11}-CH_2R^{12}$, $-CHR^{11}-CH_2-CH_2R^{12}$, $-C(Y)R^{12}$, $-C(Y)-CH_2R^{12}$, $-C(Y)-CH_2-CH_2R^{12}$ or $-C(Y)-CH_2-CH_2R^{12}$ where Y=O or S, in particular $R^5$ is chosen from $-CHR^{11}R^{12}$, $-CHR^{11}-CH_2R^{12}$, $-CHR^{11}-CH_2-CH_2R^{12}$, $-C(Y)R^{12}$ or $-C(Y)-CH_2R^{12}$ where Y=O.

In respect of the above embodiment, it is particularly preferable if, in the substituted cyclohexane-1,4-diamine compound according to formula I used, $R^{11}$ is chosen from H, $C_{1-4}$-alkyl, saturated or unsaturated, branched or unbranched, mono- or polysubstituted or unsubstituted; or $C(O)O-C_{1-4}$-alkyl, saturated or unsaturated, branched or unbranched, mono- or polysubstituted or unsubstituted;

preferably

H, $C_{1-4}$-alkyl, saturated or unsaturated, branched or unbranched, mono- or polysubstituted or unsubstituted; or $C(O)O-C_{1-2}$-alkyl, saturated, unbranched, mono- or polysubstituted or unsubstituted;

in particular

H, $CH_3$, $C_2H_5$ and $C(O)O-CH_3$;

and/or in the substituted cyclohexane-1,4-diamine compound according to formula I used, $R^{12}$ is chosen from $C_{3-8}$-cycloalkyl, aryl or heteroaryl, in each case unsubstituted or mono- or polysubstituted;

preferably

R$^{12}$ is chosen from cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, in each case unsubstituted or mono- or polysubstituted;

in particular

R$^{12}$ is chosen from cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, in each case unsubstituted or mono- or polysubstituted.

Generally, under particular circumstances it may be favourable for all the substituted cyclohexane-1,4-diamine compounds, medicaments or processes according to the invention which are described above if R$^4$ and R$^5$ together do not form a heterocyclic radical.

The invention also provides a process for treatment, in particular in one of the abovementioned indications, of a non-human mammal or human which or who requires treatment of pain, in particular chronic pain, by administration of a therapeutically active dose of a substituted cyclohexane-1,4-diamine compound according to the invention, or of a medicament according to the invention.

The invention also provides a process for the preparation of the substituted cyclohexane-1,4-diamine compounds according to the invention as described in the following description and examples.

A process, called the main process in the following, for the preparation of a substituted cyclohexane-1,4-diamine compound according to the invention with the following steps is particularly suitable here:

a. a cyclohexane-1,4-dione, protected with groups S$^1$ and S$^2$, according to formula II is reacted with a cyanide, preferably potassium cyanide, in the presence of a compound of the formula HNR$^{01}$R$^{02}$ to give a protected N-substituted 1-amino-4-oxo-cyclohexane-carbonitrile compound according to formula III;

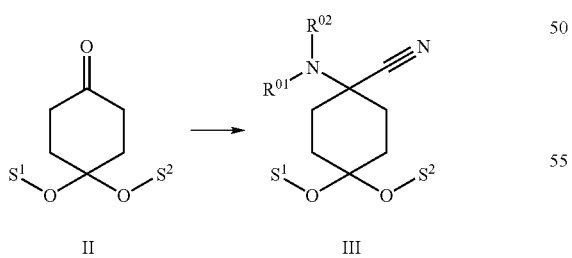

and optionally subsequently, in any desired sequence and optionally repeatedly, acylation, alkylation or sulfonation is carried out and/or in the case of compounds where R$^{01}$ and/or R$^{02}$ and/or R$^{06}$=H protected with a protective group, at least once a protective group is split off and acylation, alkylation or sulfonation is optionally carried out and/or in the case of compounds where R$^{01}$ and/or R$^{02}$ and/or R$^{06}$=H, at least once a protective group is introduced and acylation, alkylation or sulfonation is optionally carried out, b. the aminonitrile according to formula III is reacted with organometallic reagents, preferably Grignard or organolithium reagents, of the formula metal-R$^3$, so that a compound according to formula IVa is formed;

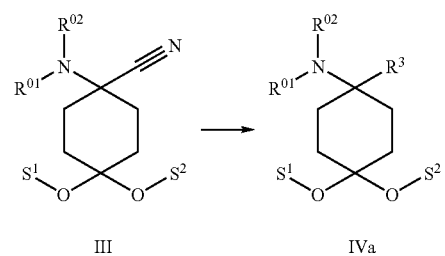

and optionally subsequently, in any desired sequence and optionally repeatedly, acylation, alkylation or sulfonation is carried out and/or in the case of compounds where R$^{01}$ and/or R$^{02}$ and/or R$^{06}$=H protected with a protective group, at least once a protective group is split off and acylation, alkylation or sulfonation is optionally carried out and/or in the case of compounds where R$^{01}$ and/or R$^{02}$ and/or R$^{06}$=H, at least once a protective group is introduced and acylation, alkylation or sulfonation is optionally carried out, c. on the compound according to formula IVa, the protective groups S$^1$ and S$^2$ are split off, so that a 4-substituted 4-aminocyclohexanone compound according to formula IV is formed;

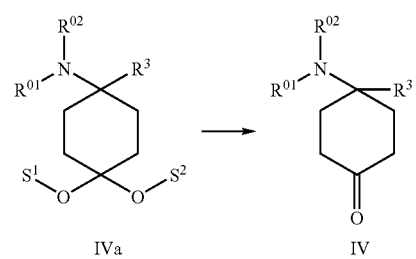

and optionally subsequently, in any desired sequence and optionally repeatedly, acylation, alkylation or sulfonation is carried out and/or in the case of compounds where R$^{01}$ and/or R$^{02}$ and/or R$^{06}$=H protected with a protective group, at least once a protective group is split off and acylation, alkylation or sulfonation is optionally carried out and/or in the case of compounds where R$^{01}$ and/or R$^{02}$ and/or R$^{06}$=H, at least once a protective group is introduced and acylation, alkylation or sulfonation is optionally carried out, d. the 4-substituted 4-aminocyclohexanone compound according to formula IVa is aminated reductively with a compound of the formula HNR$^{04}$R$^{05}$, so that a cyclohexane-1,4-diamine compound according to formula V is formed;

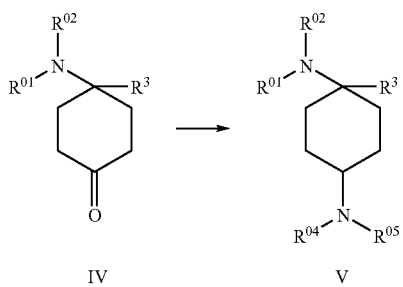

IV          V and optionally subsequently, in any desired sequence and optionally repeatedly, acylation, alkylation or sulfonation is carried out and/or in the case of compounds where $R^{01}$ and/or $R^{02}$ and/or $R^{04}$ and/or $R^{05}$ and/or $R^{06}$=H protected with a protective group, at least once a protective group is split off and acylation, alkylation or sulfonation is optionally carried out and/or in the case of compounds where $R^{01}$ and/or $R^{02}$ and/or $R^{04}$ and/or $R^{05}$ and/or $R^{06}$=H, at least once a protective group is introduced and acylation, alkylation or sulfonation is optionally carried out, until a compound according to formula I is formed, wherein $R^1$, $R^2$, $R^3$ $R^4$ and $R^5$ have the meaning given for compound group (A) according to formula I and $R^{01}$ and $R^{02}$ independently of one another are chosen from
H; H provided with a protective group; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted;
or the radicals $R^{01}$ and $R^{02}$ together form a ring and denote $CH_2CH_2OCH_2CH_2$, $CH_2CH_2NR^{06}CH_2CH_2$ or $(CH_2)_{3-6}$,
where $R^{06}$ is chosen from H; H provided with a protective group; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted;

$R^{04}$ is chosen from H, H provided with a protective group; $C_{1-8}$-alkyl, saturated or unsaturated, branched or unbranched, mono- or polysubstituted or unsubstituted;

$R^{05}$ is chosen from H, H provided with a protective group; $C_{3-8}$-cycloalkyl, aryl or heteroaryl, in each case unsubstituted or mono- or polysubstituted; —$CHR^{11}R^{12}$, —$CHR^{11}$—$CH_2R^{12}$, —$CHR^{11}$—$CH_2$—$CH_2R^{12}$, —$CHR^{11}$—$CH_2$—$CH_2$—$CH_2R^{12}$, —$C(Y)R^{12}$, —$C(Y)$—$CH_2R^{12}$, —$C(Y)$—$CH_2$—$CH_2R^{12}$ or —$C(Y)$—$CH_2$—$CH_2$—$CH_2R^{12}$
where Y=$H_2$,
where $R^{11}$ is chosen from
H, $C_{1-7}$-alkyl, saturated or unsaturated, branched or unbranched, mono- or polysubstituted or unsubstituted;
and where $R^{12}$ is chosen from
H; $C_{3-8}$-cycloalkyl, aryl or heteroaryl, in each case unsubstituted or mono- or polysubstituted, or $R^{04}$ and $R^{05}$ together form a heterocyclic radical having between 3 and 8 atoms in the ring, saturated or unsaturated; mono- or polysubstituted or unsubstituted, and $S^1$ and $S^2$ independently of one another are chosen from protective groups or together denote a protective group, preferably monoacetal.

Alkylation here is also understood as meaning a reductive amination, since it leads to the same result.

The invention furthermore preferably provides a process, called the alternative process in the following, for the preparation of a substituted cyclohexane-1,4-diamine compound according to the invention with the following steps:

a. a cyclohexane-1,4-dione, protected with the groups $S^1$ and $S^2$, according to formula II is aminated reductively with a compound of the formula $HNR^{04}R^{05}$, so that a 4-aminocyclohexanone compound according to formula VI is formed;

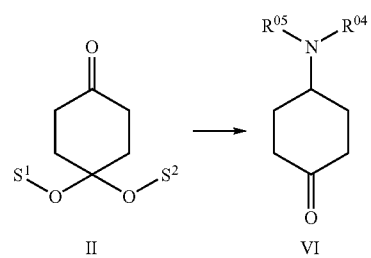

II          VI and optionally subsequently, in any desired sequence and optionally repeatedly, acylation, alkylation or sulfonation is carried out and/or in the case of compounds where $R^{04}$ and/or $R^{05}$=H protected with a protective group, at least once a protective group is split off and acylation, alkylation or sulfonation is optionally carried out and/or in the case of compounds where $R^{04}$ and/or $R^{05}$=H, at least once a protective group is introduced and acylation, alkylation or sulfonation is optionally carried out, b. the 4-aminocyclohexanone compound according to formula VI is reacted with cyanide, preferably potassium cyanide, in the presence of a compound of the formula $HNR^{01}R^{02}$ to give a cyclohexanone-nitrile compound of the formula VII,

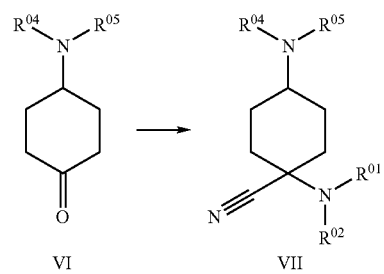

VI          VII and optionally subsequently, in any desired sequence and optionally repeatedly, acylation, alkylation or sulfonation is carried out and/or in the case of compounds where $R^{01}$ and/or $R^{02}$ and/or $R^{04}$ and/or $R^{05}$ and/or $R^{06}$=H protected with a protective group, at least once a protective group is split off and acylation, alkylation or sulfonation is optionally carried out and/or in the case of compounds where $R^{01}$ and/or $R^{02}$ and/or $R^{04}$ and/or $R^{05}$ and/or $R^{06}$=H, at least once a protective group is introduced and acylation, alkylation or sulfonation is optionally carried out, c. the cyclohexanone-nitrile compound of the formula VII is reacted with organometallic reagents, preferably Grignard or organolithium reagents, of the formula metal-$R^3$ and, finally, the protective groups $S^1$ and $S^2$ are split off, so that a cyclohexane-1,4-diamine compound according to formula V is formed,

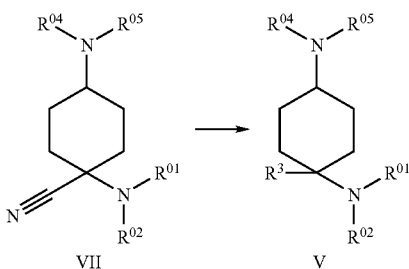

and optionally subsequently, in any desired sequence and optionally repeatedly, acylation, alkylation or sulfonation is carried out and/or in the case of compounds where $R^{01}$ and/or $R^{02}$ and/or $R^{04}$ and/or $R^{05}$ and/or $R^{06}$=H protected with a protective group, at least once a protective group is split off and acylation, alkylation or sulfonation is optionally carried out and/or in the case of compounds where $R^{01}$ and/or $R^{02}$ and/or $R^{04}$ and/or $R^{05}$ and/or $R^{06}$=H, at least once a protective group is introduced and acylation, alkylation or sulfonation is optionally carried out, until a compound according to formula I is formed, wherein $R^1$, $R^2$, $R^3$ $R^4$ and $R^5$ have the meaning given for compound group (A) according to formula I and $R^{01}$ and $R^{02}$ independently of one another are chosen from H; H provided with a protective group; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted; or the radicals $R^{01}$ and $R^{02}$ together form a ring and denote $CH_2CH_2OCH_2CH_2$, $CH_2CH_2NR^{06}CH_2CH_2$ or $(CH_2)_{3-6}$, where $R^{06}$ is chosen from H; H provided with a protective group; $C_{1-8}$-alkyl or $C_{3-8}$-cycloalkyl, in each case saturated or unsaturated, branched or unbranched, mono- or polysubstituted or unsubstituted; aryl-, or heteroaryl, in each case mono- or polysubstituted or unsubstituted; or aryl, $C_{3-8}$-cycloalkyl or heteroaryl, bonded via $C_{1-3}$-alkylene and in each case mono- or polysubstituted or unsubstituted;

$R^{04}$ is chosen from H, H provided with a protective group; $C_{1-8}$-alkyl, saturated or unsaturated, branched or unbranched, mono- or polysubstituted or unsubstituted;

$R^{05}$ is chosen from H, H provided with a protective group; $C_{3-8}$-cycloalkyl, aryl or heteroaryl, in each case unsubstituted or mono- or polysubstituted; —$CHR^{11}R^{12}$, —$CHR^{11}$—$CH_2R^{12}$, —$CHR^{11}$—$CH_2$—$CH_2R^{12}$, —$CHR^{11}$—$CH_2$—$CH_2$—$CH_2R^{12}$, —$C(Y)R^{12}$, —$C(Y)$—$CH_2R^{12}$, —$C(Y)$—$CH_2$—$CH_2R^{12}$ or —$C(Y)$—$CH_2$—$CH_2$—$CH_2R^{12}$ where Y=$H_2$, where $R^{11}$ is chosen from
H, $C_{1-7}$-alkyl, saturated or unsaturated, branched or unbranched, mono- or polysubstituted or unsubstituted;

and where $R^{12}$ is chosen from
H; $C_{3-8}$-cycloalkyl, aryl or heteroaryl, in each case unsubstituted or mono- or polysubstituted, or $R^{04}$ and $R^{05}$ together form a heterocyclic radical having between 3 and 8 atoms in the ring, saturated or unsaturated; mono- or polysubstituted or unsubstituted, and $S^1$ and $S^2$ independently of one another are chosen from protective groups or together denote a protective group, preferably monoacetal.

For both processes it is preferable if the protective groups on the H in $R^{01}$, $R^{02}$, $R^{04}$, $R^{05}$ and/or $R^{06}$ are chosen from alkyl, benzyl or carbamates, for example FMOC, Z or Boc.

It is furthermore preferable for the main process if the reductive amination in step d takes place in the presence of ammonium formate, ammonium acetate or $NaCNBH_3$.

For the main process it is also a particularly favourable embodiment if instead of the reductive amination with $HNR^{04}R^{05}$ in step d, the compound IV is reacted with hydroxylamine and reduction is carried out after the oxime formation.

It is also favourable for the alternative process if in step b the radical $R^{01}$ in formula $HNR^{01}R^{02}$ is H, the reaction with the cyanide is carried out with TMSCN and optionally subsequently a protective group is introduced on $R^{01}$.

The invention is explained further by the following examples which are not intended to and should not be interpreted to limit the scope of the invention in any way.

EXAMPLES

The following examples serve to explain the invention in more detail, but do not limit the general inventive idea.

The yields of the compounds prepared are not optimized.

All temperatures are uncorrected.

The term "ether" means diethyl ether, "EE" means ethyl acetate and "MC" means methylene chloride. The term "equivalents" means substance amount equivalents, "m.p." means melting point or melting range, "RT" means room temperature, "vol. %" means percent by volume, "wt. %" means percent by weight and "M" is the concentration stated in mol/l.

Silica gel 60 (0.040-0.063 mm) from E. Merck, Darmstadt, was employed as the stationary phase for the column chromatography.

The thin layer chromatography analyses were carried out with HPTLC pre-coated plates, silica gel 60 F 254 from E. Merck, Darmstadt.

The mixing ratios of mobile phases for chromatography analyses are always stated in volume/volume.

Example 1

N'-Benzyl-N,N-dimethyl-1-phenyl-cyclohexane-1,4-diamine hydrochloride, nonpolar diastereomer 200 ml methanol, 1,680 ml aqueous dimethylamine solution (40 wt. %), 303 g dimethylamine hydrochloride and 200 g potassium cyanide were added to 200 g 1,4-dioxa-spiro [4.5]decan-8-one and the mixture was stirred for approx. 65 hours. The white suspension obtained was extracted four times with 800 ml ether each time, the combined extracts were concentrated, the residue was taken up in approx. 500 ml methylene chloride and the phases were separated. The methylene chloride phase was dried over sodium sulfate, filtered and concentrated. 265 g 8-dimethylamino-1,4-dioxa-spiro[4.5]decane-8-carbonitrile were obtained as a white solid.

50.0 g 8-dimethylamino-1,4-dioxa-spiro[4.5]decane-8-carbonitrile were dissolved in 400 ml analytical grade tetrahydrofuran, 216 ml of a commercially obtainable two molar solution of phenylmagnesium chloride in tetrahydrofuran were added dropwise under a nitrogen atmosphere, while cooling on an ice-bath, and the mixture was stirred overnight, while warming to room temperature. For working up, 200 ml ice-cold ammonium chloride solution (20 wt. %) were added, while stirring and cooling on an ice-bath, and after 30 minutes the phases were separated. The aqueous phase was extracted twice with 250 ml ether each time, the extracts were combined with the organic phase, the mixture was washed with 200 ml water followed by 200 ml saturated sodium chloride solution, dried over sodium sulfate and filtered and the filtrate was concentrated. 60.0 g dimethyl-(8-phenyl-1,4-dioxa-spiro[4.5]dec-8-yl)-amine were obtained.

165 ml hydrochloric acid (32 wt. %) were diluted with 100 ml water, 60.0 g dimethyl-(8-phenyl-1,4-dioxa-spiro[4.5]dec-8-yl)-amine were added to this approx. six molar hydrochloric acid and the mixture was stirred for 24 hours. The reaction mixture was washed three times with 50 ml diethyl ether each time, rendered alkaline (pH>10) with 100 ml sodium hydroxide solution (32 wt. %) and extracted three times with 100 ml methylene chloride each time. The extracts were combined, dried over sodium sulfate and filtered and the filtrate was concentrated. 36.1 g 4-dimethylamino-4-phenyl-cyclohexanone were obtained.

2.00 g 4-dimethylamino-4-phenyl-cyclohexanone were dissolved in 30 ml analytical grade tetrahydrofuran, and 986 mg benzylamine followed by 794 µl glacial acetic acid were added, while stirring in an ice-bath. 2.72 g sodium triacetoxyborohydride were then added in portions in the course of 15 minutes and the mixture was subsequently stirred for approx. 65 hours. For working up, 15 ml two molar sodium hydroxide solution were added dropwise (pH>10) and the mixture was extracted three times with 25 ml diethyl ether each time. The combined organic phases were then washed twice with 20 ml water each time, dried over sodium sulfate and filtered and the filtrate was concentrated. The crude product obtained was chromatographed over silica gel with diethyl ether with the addition of one percent by volume of aqueous ammonia solution (25 wt. %). 844 mg of the nonpolar diastereoisomer of N'-benzyl-N,N-dimethyl-1-phenyl-cyclohexane-1,4-diamine were obtained, and were converted into 843 mg of the corresponding hydrochloride by dissolving in 6.8 ml 2-butanone and addition of 27.1 µl water followed by 381 µl chlorotrimethylsilane and stirring overnight.

Example 2

N'-Benzyl-N,N-dimethyl-1-phenyl-cyclohexane-1,4-diamine hydrochloride, polar diastereomer As described for example 1, 1.01 g of the polar diastereomer of N'-benzyl-N,N-dimethyl-1-phenyl-cyclohexane-1,4-diamine were also obtained, and were converted into 781 mg of the corresponding hydrochloride by dissolving in 8.1 ml 2-butanone and addition of 32.5 µl water followed by 457 µl chlorotrimethylsilane and stirring overnight.

Example 3

1,N'-Dibenzyl-N,N-dimethyl-cyclohexane-1,4-diamine hydrochloride, nonpolar diastereomer 50.0 g 8-dimethylamino-1,4-dioxa-spiro[4.5]decane-8-carbonitrile (see example 1) were dissolved in 400 ml analytical grade tetrahydrofuran, 214 ml of a commercially obtainable two molar solution of benzylmagnesium chloride in tetrahydrofuran were added dropwise under a nitrogen atmosphere, while cooling on an ice-bath, and the mixture was stirred overnight, while warming to room temperature. For working up, 200 ml ice-cold ammonium chloride solution (20 wt. %) were added, while stirring and cooling on an ice-bath, and after 30 minute the phases were separated. The aqueous phase was extracted twice with 250 ml ether each time, the extracts were combined with the organic phase, the mixture was washed with 200 ml water followed by 200 ml saturated sodium chloride solution, dried over sodium sulfate and filtered and the filtrate was concentrated. 78.4 g crude product which consisted predominantly of (8-benzyl-1,4-dioxa-spiro[4.5]dec-8-yl)-dimethyl-amine and was reacted further without additional purification were obtained.

200 ml hydrochloric acid (32 wt. %) were diluted with 120 ml water, 78.4 g crude (8-benzyl-1,4-dioxa-spiro[4.5]dec-8-yl)-dimethyl-amine were added to this approx. six molar hydrochloric acid and the mixture was stirred for 24 hours. The reaction mixture was washed three times with 100 ml diethyl ether each time, rendered alkaline (pH>10) with 100 ml sodium hydroxide solution (32 wt. %), while cooling on an ice-bath, and extracted three times with 100 ml methylene chloride each time. The extracts were combined, dried over sodium sulfate and filtered and the filtrate was concentrated. 50.4 g 4-benzyl-4-dimethylamino-cyclohexanone were obtained.

2.00 g 4-benzyl-4-dimethylamino-cyclohexanone were dissolved in 30 ml analytical grade tetrahydrofuran, and 926 mg benzylamine followed by 746 µl glacial acetic acid were added, while stirring in an ice-bath. 2.56 g sodium triacetoxyborohydride were then added in portions in the course of 15 minutes and the mixture was subsequently stirred for approx. 65 hours. For working up, 15 ml two molar sodium hydroxide solution were added dropwise (pH>10) and the mixture was extracted three times with 25 ml diethyl ether each time. The combined organic phases were then washed twice with 20 ml water each time, dried over sodium sulfate and filtered and the filtrate was concentrated. The crude product obtained was chromatographed over silica gel with diethyl ether with the addition of one percent by volume of aqueous ammonia solution (25 wt. %). 774 mg of the nonpolar diastereoisomer of 1,N'-dibenzyl-N,N-dimethyl-cyclohexane-1,4-diamine were obtained, and were converted into 731 mg of the corresponding hydrochloride by dissolving in 6.2 ml 2-butanone and addition of 23.8 µl water followed by 334 µl chlorotrimethylsilane and stirring overnight.

Example 4

1,N-Dibenzyl-N,N-dimethyl-cyclohexane-1,4-diamine hydrochloride, polar diastereomer As described for example 3, 820 mg of the polar diastereomer of 1,N'-dibenzyl-N,N-dimethyl-cyclohexane-1,4-diamine were also obtained, and were converted into 793 mg of the corresponding hydrochloride by dissolving in 6.6 ml 2-butanone and addition of 25.2 µl water followed by 354 µl chlorotrimethylsilane and stirring overnight.

Example 5

N-(4-Benzyl-4-dimethylamino-cyclohexyl)-N-propyl-benzamide hydrochloride 6.00 g 4-benzyl-4-dimethylamino-cyclohexanone (see example 3) were dissolved in 90 ml analytical grade tetrahydrofuran, and 1.53 g n-propylamine followed by 3.36 ml glacial acetic acid were added, while stirring in an ice-bath. 7.68 g sodium triacetoxyborohydride were then added in portions in the course of 15 minutes and the mixture was subsequently stirred for approx. 65 hours. For working up, 45 ml two molar sodium hydroxide solution were added dropwise (pH>10) and the mixture was extracted three times with 50 ml diethyl ether each time. The combined organic phases were washed twice with 50 ml water each time, dried over sodium sulfate and filtered and the filtrate was concentrated. The crude product obtained (6.43 g) was chromatographed over silica gel with diethyl ether with the addition of five percent by volume of aqueous ammonia solution (25 wt. %). 707 mg of the nonpolar diastereoisomer of 1-benzyl-N,N-dimethyl-N'-propyl-cyclohexane-1,4-diamine were obtained.

700 mg of the nonpolar diastereomer of 1-benzyl-N,N-dimethyl-N'-propyl-cyclohexane-1,4-diamine were dissolved in 10 ml methylene chloride, and 370 µl triethylamine and approx. 10 mg DMAP (4-dimethylaminopyridine) were added. 311 µl benzoyl chloride were added dropwise, while cooling in an ice/methanol bath, and the reaction mixture was then stirred overnight, while warming to room temperature. For working up, 10 ml five molar KOH solution and 10 ml water were added, the mixture was stirred for ten minutes and extracted three times with 20 ml methylene chloride each time, the combined extracts were dried over magnesium sulfate and filtered and the filtrate was concentrated. From the crude product obtained (834 mg), 909 mg N-(4-benzyl-4-dimethylamino-cyclohexyl)-N-propyl-benzamide hydrochloride were prepared as described for example 1 with water and chlorotrimethylsilane in 2-butanone.

Example 6

N,N-Dimethyl-1-phenyl-N'-propyl-cyclohexane-1,4-diamine hydrochloride, nonpolar diastereomer 10.0 g 4-dimethylamino-4-phenyl-cyclohexanone were dissolved in 160 ml analytical grade tetrahydrofuran, and 2.72 g n-propylamine followed by 5.97 ml glacial acetic acid were added, while stirring in an ice-bath. 13.6 g sodium triacetoxyborohydride were then added in portions in the course of 15 minutes and the mixture was subsequently stirred for approx. 65 hours. For working up, 85 ml two molar sodium hydroxide solution were added dropwise (pH>10) and the mixture was extracted three times with 100 ml diethyl ether each time. The combined organic phases were then washed twice with 100 ml water each time, dried over sodium sulfate and filtered and the filtrate was concentrated. 5.00 g of the crude product obtained (9.79 g) were chromatographed over silica gel with diethyl ether, to which one percent by volume of aqueous ammonia solution (25 wt. %) was added, and an addition of methanol increasing from one to forty per cent by volume. 2.79 g of the nonpolar and 1.33 g of the polar diastereoisomer of N,N-dimethyl-1-phenyl-N'-propyl-cyclohexane-1,4-diamine were obtained.

From a sample of 356 mg of the nonpolar diastereoisomer, 253 mg of the corresponding hydrochloride were obtained as described for example 1 with water and chlorotrimethylsilane in 2-butanone.

Example 7

N-(4-Dimethylamino-4-phenyl-cyclohexyl)-N-propyl-benzamide hydrochloride, nonpolar diastereomer 1.00 g of the nonpolar diastereomer of N,N-dimethyl-1-phenyl-N'-propyl-cyclohexane-1,4-diamine (see example 6) were dissolved in 15 ml methylene chloride, and 560 µl triethylamine and approx. 10 mg DMAP were added. 468 µl benzoyl chloride were added dropwise, while cooling in an ice/methanol bath, and the reaction mixture was then stirred overnight, while warming to room temperature. For working up, 12 ml five molar KOH solution and 12 ml water were added, the mixture was stirred for ten minutes and extracted three times with 25 ml methylene chloride each time, the combined extracts were dried over magnesium sulfate and filtered and the filtrate was concentrated. From the product obtained (1.31 g), 1.01 g of the nonpolar diastereomer of N-(4-benzyl-4-dimethylamino-cyclohexyl)-N-propyl-benzamide hydrochloride were prepared as described for example 1 with water and chlorotrimethylsilane in 2-butanone.

Example 8

N-(4-Dimethylamino-4-phenyl-cyclohexyl)-N-propyl-benzamide hydrochloride, polar diastereomer 1.00 g of the polar diastereomer of N,N-dimethyl-1-phenyl-N'-propyl-cyclohexane-1,4-diamine (see example 6) were dissolved in 15 ml methylene chloride, and 560 µl triethylamine and approx. 10 mg DMAP were added. 468 µl benzoyl chloride were added dropwise, while cooling in an ice/methanol bath, and the reaction mixture was then stirred overnight, while warming to room temperature. For working up, 12 ml five molar KOH solution and 12 ml water were added, the mixture was stirred for ten minutes and extracted three times with 25 ml methylene chloride each time, the combined extracts were dried over magnesium sulfate and filtered and the filtrate was concentrated. From the product obtained (1.29 g), 752 mg of the polar diastereomer of N-(4-benzyl-4-dimethylamino-cyclohexyl)-N-propyl-benzamide hydrochloride were prepared as described for example 1 with water and chlorotrimethylsilane in 2-butanone.

Example 9

1,N'-Dibenzyl-N,N,N'-trimethyl-cyclohexane-1,4-diamine hydrochloride, nonpolar diastereomer 10.0 g 4-benzyl-4-dimethylamino-cyclohexanone (see example 3) were dissolved in 150 ml analytical grade tetrahydrofuran, and 5.24 g benzyl-methyl-amine followed by 5.60 ml glacial acetic acid were added, while stirring in an ice-bath. 12.8 g sodium triacetoxyborohydride were then added in portions in the course of 15 minutes and the mixture was subsequently stirred overnight. For working up, 75 ml two molar sodium hydroxide solution were added dropwise (pH>10) and the mixture was extracted three times with 100 ml diethyl ether each time. The combined organic phases were then washed twice with 100 ml water each time, dried over sodium sulfate and filtered and the filtrate was concentrated. The crude product obtained (13.1 g) was chromatographed over silica gel with ethyl acetate and an addition of methanol increasing from zero to one hundred percent by volume. In addition to a mixed fraction of 5.23 g, 5.37 g of the nonpolar and 1.20 g of the polar diastereoisomer of N,N-dimethyl-1-phenyl-N'-propyl-cyclohexane-1,4-diamine were obtained. From the nonpolar diastereoisomer, 5.44 g of the corresponding hydrochloride were obtained as described for example 1 with water and chlorotrimethylsilane in 2-butanone.

Example 10

1,N'-Dibenzyl-N,N,N'-trimethyl-cyclohexane-1,4-diamine hydrochloride, polar diastereomer As described for example 9, from 1.20 g of the polar diastereomer of 1,N'-dibenzyl-N,N,N'-trimethyl-cyclohexane-1,4-diamine, 1.24 g of the corresponding hydrochloride were obtained.

Example 11

N-(4-Benzyl-4-dimethylamino-cyclohexyl)-N-methyl-benzamide hydrochloride, polar diastereomer 15.0 g 4-benzyl-4-dimethylamino-cyclohexanone (see example 3) were dissolved in 225 ml analytical grade tetrahydrofuran, and 4.38 g methylamine hydrochloride, 8.9 ml triethylamine and 8.40 ml glacial acetic acid were added, while stirring in an ice-bath. 19.2 g sodium triacetoxyborohydride were then added in portions in the course of 15 minutes and the mixture was subsequently stirred overnight. For working up, 110 ml two molar sodium hydroxide solution were added dropwise (pH>10) and the mixture was extracted three times with 200 ml diethyl ether each time. The combined organic phases were washed twice with 200 ml water each time, dried over sodium sulfate and filtered and the filtrate was concentrated. The crude product obtained (15.0 g) was chromatographed over silica gel with methanol with the addition of one percent by volume of aqueous ammonia solution (25 wt. %). 11.6 g of the still significantly contaminated product were obtained, and were chromatographed again over silica gel with ethyl acetate and an addition of methanol rising from twenty-five to fifty percent by volume. 6.67 g 1-benzyl-N,N,N'-trimethyl-cyclohexane-1,4-diamine were obtained as a cis/trans mixture.

3.00 g 1-benzyl-N,N,N'-trimethyl-cyclohexane-1,4-diamine were dissolved in 50 ml methylene chloride, and 1.78 ml triethylamine and approx. 10 mg DMAP were added. 1.41 ml benzoyl chloride were added dropwise, while cooling in an ice/methanol bath, and the reaction mixture was then stirred overnight, while warming to room temperature. For working up, 50 ml five molar KOH solution and 50 ml water were added, the mixture was stirred for ten minutes and extracted three times with 50 ml methylene chloride each time, the combined extracts were dried over magnesium sulfate and filtered and the filtrate was concentrated. The crude product obtained (3.61 g) was chromatographed over silica gel with methanol/ether 1:1. 231 mg of the polar diastereomer of N-(4-benzyl-4-dimethylamino-cyclohexyl)-N-methyl-benzamide were obtained, from which 188 mg of the corresponding hydrochloride were prepared as described for example 1 with water and chlorotrimethylsilane in 2-butanone.

Example 12

N-(4-Benzyl-4-dimethylamino-cyclohexyl)-N-ethyl-benzamide hydrochloride, polar diastereomer 15.0 g 4-benzyl-4-dimethylamino-cyclohexanone (see example 3) were dissolved in 225 ml analytical grade tetrahydrofuran, and 2.89 g ethylamine followed by 8.40 ml glacial acetic acid were added, while stirring in an ice-bath. 19.2 g sodium triacetoxyborohydride were then added in portions in the course of 15 minutes and the mixture was subsequently stirred overnight. For working up, 110 ml two molar sodium hydroxide solution were added dropwise (pH>10) and the mixture was extracted three times with 200 ml diethyl ether each time. The combined organic phases were washed twice with 200 ml water each time, dried over sodium sulfate and filtered and the filtrate was concentrated. The crude product obtained (15.7 g) was chromatographed over silica gel with methanol with the addition of one percent by volume of aqueous ammonia solution (25 wt. %). 14.1 g of the still significantly contaminated product were obtained, and were chromatographed again over silica gel with methanol with the addition of one percent by volume of aqueous ammonia solution (25 wt. %). 12.1 g 1-benzyl-N'-ethyl-N,N-dimethyl-cyclohexane-1,4-diamine were obtained as a cis/trans mixture.

3.00 g 1-benzyl-N'-ethyl-N,N-dimethyl-cyclohexane-1,4-diamine were dissolved in 50 ml methylene chloride, and 1.68 ml triethylamine and approx. 10 mg DMAP were added. 1.40 ml benzoyl chloride were added dropwise, while cooling in an ice/methanol bath, and the reaction mixture was then stirred overnight, while warming to room temperature. For working up, 50 ml five molar KOH solution and 50 ml water were added, the mixture was stirred for ten minutes and extracted three times with 50 ml methylene chloride each time, the combined extracts were dried over magnesium sulfate and filtered and the filtrate was concentrated. The crude product obtained (4.05 g) was chromatographed over silica gel with methanol/ether 1:1. 1.09 g of the polar diastereomer of N-(4-benzyl-4-dimethylamino-cyclohexyl)-N-ethyl-benzamide were obtained, from which 1.01 mg of the corresponding hydrochloride were prepared as described for example 1 with water and chlorotrimethylsilane in 2-butanone.

Example 13

1-Benzyl-N'-(1H-indol-3-ylmethyl)-N,N-dimethyl-cyclohexane-1,4-diamine dihydrochloride 14.5 g 3-formylindole and 13.9 g hydroxylamine hydrochloride were heated at the boiling point in a mixture of dry pyridine (80 ml) and abs. ethanol (80 ml) for two hours. The initially yellow reaction mixture became deep red in color in this time. Thereafter, the solvent mixture was distilled off in vacuo. To remove the pyridine, the residue was evaporated to dryness three more times with ethanol (30 ml each time). Water (100 ml) was then added to the residue and the mixture was stirred vigorously with a magnetic stirrer for 30 minutes. The reaction solution with the pink-colored solid which had formed was cooled in a refrigerator for two hours. The oxime obtained was filtered off with suction, washed with water (3×25 ml) and dried in a desiccator. 15.6 g 1H-indole-3-carbaldehyde (Z)-oxime with a melting point of 190-193° C. were obtained.

4.8 g (1H-indole-3-carbaldehyde (Z)-oxime were suspended in methanol (100 ml) (poorly soluble) and the suspension was diluted with five molar sodium hydroxide solution (100 ml). The reaction vessel was flushed constantly with a gentle stream of argon. Devarda alloy (20 g) was added to the mixture in portions. The addition depended on the vigorousness of the reaction. The mixture was cooled occasionally with ice-water. After two hours, the introduction had ended and the mixture was subsequently stirred at RT for 30 minutes and then diluted with water (100 ml). The methanol was stripped off in vacuo and the aqueous solution was extracted with ether (4×50 ml). After drying and distilling off the ether, the residue was purified by recrystallization from toluene (20 ml). 2.2 g C-(1H-indol-3-yl)-methylamine were obtained as a beige solid with a melting point of 90-94° C., which rapidly changed its color in light and at RT. Storage in dark bottles and in a refrigerator was possible for a few days.

292 mg C-(1H-indol-3-yl)-methylamine were partly dissolved in dry 1,2-dichloroethane (10 ml) under argon. After addition of 463 mg 4-benzyl-4-dimethylamino-cyclohexanone (see example 3), glacial acetic acid (4 mmol) and sodium triacetoxyborohydride (550 mg), the suspension was stirred for 72 hours at room temperature. For working up, water (10 ml) was added to the reaction mixture. The organic phase was separated off and the aqueous phase was extracted twice with ether and then rendered strongly alkaline with sodium hydroxide solution. The mixture was extracted again with ethyl acetate (4×10 ml). A pale precipitate precipitated out of the combined ethyl acetate phases even during the processing. After cooling, this was filtered off with suction, washed twice with cold ethyl acetate and dried. The product obtained in this way (235 mg) was white and solid (m.p. 194-198° C.). 217 mg were dissolved hot in 2-butanone/ethanol (30+10 ml), and saturated ethanolic hydrochloric acid (1.5 ml; 1.85 M) was added at RT, while stirring. After two hours, no precipitate had yet precipitated out. Even after reducing the amount of solvent and cooling, no hydrochloride precipitated out. The mixture was therefore evaporated to dryness at 40° C. in vacuo and excess HCl was driven off. 260 mg 1-benzyl-N'-(1H-indol-3-ylmethyl)-N,N-dimethyl-cyclohexane-1,4-diamine dihydrochloride were obtained as the residue as a pale pink-colored solid of m.p. 170-174° C.

Example 14

1-Benzyl-N'-[2-(1H-indol-3-yl)-1-methylethyl]-N,N-dimethylcyclohexane-1,4-diamine, cis/trans mixture 348 mg DL-α-methyltryptamine were dissolved in dry 1,2-dichloroethane (10 ml) under argon (clear solution), 463 mg 4-benzyl-4-dimethylamino-cyclohexane (see example 3) and glacial acetic acid (229 µl) were added and the mixture was stirred for one hour at RT. 550 mg sodium triacetoxyborohydride were then added and the suspension was stirred for a further 72 hours at RT. For working up, water (20 ml) was added to the reaction mixture, the organic phase was separated off and the aqueous phase was extracted once with ether and then rendered strongly alkaline with sodium hydroxide solution (pH>10). A gelatinous precipitate which dissolved in ethyl acetate thereby precipitated out. The aqueous phase was extracted with ethyl acetate (4×10 ml). All the ethyl acetate phases were combined, dried with sodium sulfate and concentrated to dryness. 766 mg of a mixture of cis- and trans-1-benzyl-N'-[2-(1H-indol-3-yl)-1-methylethyl]-N,N-dimethylcyclohexane-1,4-diamine were obtained as a vitreous solid (m.p. 48-53° C.).

Example 15

1-Benzyl-N'-indan-5-yl-N,N-dimethyl-cyclohexane-1,4-diamine hydrochloride 266 mg 5-aminoindane and 462 mg 4-benzyl-4-dimethylamino-cyclohexanone (see example 3) were dissolved in dry 1,2-dichloroethane under argon and the solution was stirred with 2 g sodium sulfate for 24 hours at RT. 600 mg sodium triacetoxyborohydride were added to this mixture and the mixture was stirred for two hours at RT. For working up, the reaction mixture was concentrated and the residue was adjusted to pH 11 with five molar sodium hydroxide solution. The alkaline phase was diluted with water (10 ml) and extracted with ethyl acetate (4×20 ml). The combined extracts were dried over sodium sulfate and filtered and the filtrate was concentrated. The crude product was chromatographed over silica gel with ethyl acetate. 440 mg 1-benzyl-N'-indan-5-yl-N,N-dimethyl-cyclohexane-1,4-diamine were obtained as a colorless oil. For preparation of the hydrochloride, the base was dissolved in 2-butanone (8 ml), and 1.85 M ethanolic hydrochloric acid (1.75 ml) was added. The solid which had precipitated out was filtered off with suction and dried. 280 mg 1-benzyl-N'-indan-5-yl-N,N-dimethyl-cyclohexane-1,4-diamine hydrochloride were obtained as a white solid (m.p. 200-203° C.)

Example 16

1-Benzyl-N'-indan-1-yl-N,N-dimethyl-cyclohexane-1,4-diamine dihydrochloride, cis/trans mixture 266 mg 1-aminoindane and 462 mg 4-benzyl-4-dimethylamino-cyclohexanone (see example 3) were dissolved in dry 1,2-dichloroethane under argon and the solution was stirred with 2 g sodium sulfate for 24 hours at RT. 600 mg sodium triacetoxyborohydride were added to this mixture and the mixture was stirred for two hours at RT. For working up, the reaction mixture was concentrated and the residue was adjusted to pH 11 with five molar sodium hydroxide solution. The alkaline phase was diluted with water (10 ml) and extracted with ethyl acetate (4×20 ml). The combined extracts were dried over sodium sulfate and filtered and the filtrate was concentrated. The crude product was chromatographed over silica gel with ethyl acetate. 696 mg 1-benzyl-N'-indan-1-yl-N,N-dimethyl-cyclohexane-1,4-diamine were obtained as a colorless oil. For preparation of the hydrochloride, the base was dissolved in 2-butanone (10 ml), and 1.85 M ethanolic hydrochloric acid (2.80 ml) was added. The solid which had precipitated out was filtered off with suction and dried. 540 mg of a mixture of cis- and trans-1-benzyl-N'-indan-1-yl-N,N-dimethyl-cyclohexane-1,4-diamine dihydrochloride were obtained as a white solid (m.p. 170-172° C.)

Example 17

N'-Indan-1-yl-N,N-dimethyl-1-phenyl-cyclohexane-1,4-diamine 266 mg 1-aminoindane and 434 mg 4-dimethylamino-4-phenyl-cyclohexanone were dissolved in dry 1,2-dichloroethane (10 ml) and THF (10 ml) under argon. Glacial acetic acid (2 mmol) and sodium triacetoxyborohydride (600 mg) were added to this mixture and the mixture was stirred for 24 hours at RT. For working up, the mixture was concentrated and the residue was adjusted to pH 11 with five molar sodium hydroxide solution. The alkaline phase was diluted with water (10 ml) and extracted with ethyl acetate (5×20 ml). The combined extracts were dried over sodium sulfate and filtered and the filtrate was concentrated. The crude product was chromatographed over silica gel with ethyl acetate/ethanol (1:1). 200 mg N'-indan-1-yl-N,N-dimethyl-1-phenyl-cyclohexane-1,4-diamine were obtained as a white solid (m.p. 99-101° C.).

Example 18

N'-(1H-Indol-5-yl)-N,N-dimethyl-1-phenylcyclohexane-1,4-diamine 264 mg 5-aminoindane and 434 mg 4-dimethylamino-4-phenyl-cyclohexanone were dissolved in dry 1,2-dichloroethane (10 ml) under argon. Glacial acetic acid (2 mmol) and sodium triacetoxyborohydride (600 mg) were added to this mixture and the mixture was stirred for 24 hours at RT. For working up, the mixture was concentrated and the residue was adjusted to pH 11 with five molar sodium hydroxide solution. The alkaline phase was diluted with water (10 ml) and extracted with ethyl acetate (4×20 ml). The combined extracts were dried over sodium sulfate and filtered and the filtrate was concentrated. The crude product was chromatographed over silica gel with ethyl acetate/ethanol (1:1). 315 mg N'-(1H-indol-5-yl)-N,N-dimethyl-1-phenylcyclohexane-1,4-diamine were obtained as a white solid (m.p. 191-192° C.).

Example 19

N'-(1H-Indol-3-ylmethyl)-N,N-dimethyl-1-phenyl-cyclohexane-1,4-diamine, cis/trans mixture 292 mg C-(1H-indol-3-yl)methylamine were dissolved in dry 1,2-dichloroethane (15 ml) and THF (5 ml) under argon to give an almost clear solution. After addition of 4-dimethylamino-4-phenylcyclohexanone (435 mg), glacial acetic acid (4 mmol) and sodium triacetoxyborohydride (550 mg), a suspension was present, which was stirred for 72 hours at RT. For working up, water (20 ml) was added to the reaction mixture and the mixture was stirred vigorously for one hour. The organic phase was separated off and the aqueous phase was extracted twice with ether (10 ml) and then rendered strongly alkaline with five molar sodium hydroxide solution. The aqueous phase was extracted with ethyl acetate (4×10 ml). A solid, which dissolved in ethyl acetate (50 ml) with warming, thereby precipitated out. The combined extracts were dried over sodium sulfate and filtered and the filtrate was concentrated. The crude product obtained (382 mg) was recrystallized from a mixture of ethanol (1 ml) and ethyl acetate (5 ml). The precipitate was filtered off with suction and washed with a little cold ethyl acetate. 156 mg N'-(1H-indol-3-ylmethyl)-N,N-dimethyl-1-phenyl-cyclohexane-1,4-diamine were obtained as a cis/trans mixture.

Example 20

N'-(1H-Indol-3-ylmethyl)-N,N-dimethyl-1-phenyl-cyclohexane-1,4-diamine, nonpolar diastereomer The mother liquor obtained in example 19 was concentrated. 173 mg of the nonpolar diastereomer of N'-(1H-indol-3-ylmethyl)-N,N-dimethyl-1-phenyl-cyclohexane-1,4-diamine were obtained (m.p. 170-178° C.).

Example 21

N'-[2-(1H-Indol-3-yl)-ethyl]-N,N-dimethyl-1-phenyl-cyclohexane-1,4-diamine, nonpolar diastereomer Tryptamine (320 mg) was dissolved in dry 1,2-dichloroethane (10 ml) under argon. After addition of 4-dimethylamino-4-phenylcyclohexanone (435 mg), glacial acetic acid (229 µl) and sodium triacetoxyborohydride (550 mg), the suspension was stirred for 3 days at RT. For working up, water (20 ml) was added to the reaction mixture. The organic phase was separated off and the aqueous phase was extracted once with ether and then rendered strongly alkaline with sodium hydroxide solution. The aqueous phase was milky-cloudy at pH 10. It was extracted with ethyl acetate (4×10 ml), the extracts were combined, dried over sodium sulfate and filtered and the filtrate was concentrated. The crude product obtained (674 mg) was recrystallized twice from ethyl acetate (5 ml). 22 mg of the nonpolar diastereoisomer of N'-[2-(1H-indol-3-yl)-ethyl]-N,N-dimethyl-1-phenyl-cyclohexane-1,4-diamine were obtained (m.p. 134-138° C.).

Example 22

N'-[2-(1H-Indol-3-yl)-ethyl]-N,N-dimethyl-1-phenyl-cyclohexane-1,4-diamine, cis/trans mixture As described for example 21, 320 mg N'-[2-(1H-indol-3-yl)-ethyl]-N,N-dimethyl-1-phenyl-cyclohexane-1,4-diamine were also obtained as a mixture of the cis/trans isomers (m.p. 149-153° C.).

Example 23

N'-Indan-5-yl-N,N-dimethyl-1-phenyl-cyclohexane-1,4-diamine, nonpolar diastereomer 5-Aminoindane (266 mg) and 4-dimethylamino-4-phenylcyclohexanone (434 mg) were dissolved in dry 1,2-dichloroethane (10 ml) under argon. Glacial acetic acid (2 mmol) and sodium triacetoxyborohydride (600 mg) were added and the mixture was stirred for 24 hours at RT. For working up, the reaction mixture was concentrated and the residue was adjusted to pH 11 with five molar sodium hydroxide solution. The alkaline phase was diluted with water (10 ml) and extracted with ethyl acetate (4×20 ml). The combined extracts were dried over sodium sulfate and filtered and the filtrate was concentrated. The crude product obtained was chromatographed over silica gel with ethyl acetate/ethanol (1:1). 270 mg of the nonpolar diastereoisomer of N'-indan-5-yl-N,N-dimethyl-1-phenyl-cyclohexane-1,4-diamine were obtained as a white solid (m.p. 162-164° C.).

Example 24

N'-[2-(1H-Indol-3-yl)-1-methyl-ethyl]-N,N-dimethyl-1-phenyl-cyclohexane-1,4-diamine, nonpolar diastereomer DL-α-Methyltryptamine (348 mg, 2 mmol) was dissolved in dry 1,2-dichloroethane (10 ml) under argon. After addition of 4-dimethylamino-4-phenylcyclohexanone (435 mg) and glacial acetic acid (229 µl), the mixture was stirred for one hour at RT. Sodium triacetoxyborohydride (550 mg) was then added and the suspension was stirred for four days at RT. For working up, water (15 ml) was added to the reaction mixture. The clear phases were separated and the aqueous phase was washed with ether (10 ml) and then rendered strongly alkaline with sodium hydroxide solution. The aqueous phase was extracted with ethyl acetate (4×10 ml), the combined extracts were dried over sodium sulfate and filtered and the filtrate was concentrated. The crude product obtained (723 mg) was recrystallized twice from a mixture of ethyl acetate/cyclohexane (2 ml/6 ml). A fraction of the nonpolar diastereoisomer of N'-[2-(1H-indol-3-yl)-1-methyl-ethyl]-N,N-dimethyl-1-phenyl-cyclohexane-1,4-diamine (128 mg, m.p. 155-162° C.) was obtained.

Example 25

N'-[2-(1H-Indol-3-yl)-1-methyl-ethyl]-N,N-dimethyl-1-phenyl-cyclohexane-1,4-diamine, cis/trans mixture As described for example 24, 375 mg N'-[2-(1H-indol-3-yl)-1-methyl-ethyl]-N,N-dimethyl-1-phenyl-cyclohexane-1,4-diamine were also obtained as a mixture of the cis/trans isomers (dark yellow oil).

Example 26

N'-[2-(5-Benzyloxy-1H-indol-3-yl)-ethyl]-N,N-dimethyl-1-phenyl-cyclohexane-1,4-diamine, cis/trans mixture 5-Benzyloxytryptamine (440 mg, 1.65 mmol) were dissolved in 1,2-dichloroethane (14 ml) under argon (slightly cloudy solution). After addition of 4-dimethylamino-4-phenylcyclohexanone (359 mg, 1.65 mmol) and glacial acetic acid (189 μl, 3.3 mmol), the mixture was stirred for two hours at RT. Sodium triacetoxyborohydride (462 mg) was then added and the suspension was stirred for four days at RT. For working up, water (15 ml) was added to the reaction mixture. The phases were separated and the aqueous phase was washed with ether (20 ml) and then rendered strongly alkaline with sodium hydroxide solution. The aqueous phase was extracted with ether (2×10 ml) and ethyl acetate (4×10 ml), the combined extracts were dried over sodium sulfate and filtered and the filtrate was concentrated. The crude product obtained (686 mg) was recrystallized from a mixture of ethyl acetate/cyclohexane (35 ml/5 ml). 396 mg N'-[2-(5-benzyloxy-1H-indol-3-yl)-ethyl]-N,N-dimethyl-1-phenyl-cyclohexane-1,4-diamine were obtained as a cis/trans mixture (m.p. 130-134° C.).

Example 27

N'-(9H-Fluoren-1-yl)-N,N-dimethyl-1-phenyl-cyclohexane-1,4-diamine dihydrochloride 1-Aminofluorene (181 mg, 1 mmol) and 4-dimethylamino-4-phenylcyclohexanone (217 mg, 1 mmol) were dissolved in dry 1,2-dichloroethane (10 ml) under argon. Glacial acetic acid (1 mmol) and sodium triacetoxyborohydride (300 mg) were added to this mixture and the mixture was stirred for 24 hours at RT. For working up, the mixture was concentrated and the residue was adjusted to pH 11 with five molar sodium hydroxide solution. The alkaline phase was diluted with water (10 ml) and extracted with ethyl acetate (4×20 ml). The combined extracts were dried over sodium sulfate and the filtrate was concentrated. The crude product was chromatographed over silica gel with ethyl acetate/ethanol (1:1). 200 mg N'-(9H-fluoren-1-yl)-N,N-dimethyl-1-phenyl-cyclohexane-1,4-diamine were obtained as a colorless oil, which, for preparation of the hydrochloride, was dissolved in 2-butanone (5 ml), and 1.85 M ethanolic HCl (0.7 ml) was added. The N'-(9H-fluoren-1-yl)-N,N-dimethyl-1-phenyl-cyclohexane-1,4-diamine dihydrochloride obtained was filtered off with suction and dried (220 mg, m.p. 223-225° C.).

Example 28

N'-Indan-2-yl-N,N-dimethyl-1-phenyl-cyclohexane-1,4-diamine dihydrochloride, cis/trans mixture 2-Aminoindane (266 mg, 2 mmol) and 4-dimethylamino-4-phenylcyclohexanone (434 mg, 2 mmol) were dissolved in dry 1,2-dichloroethane (10 ml) under argon. Glacial acetic acid (2 mmol) and sodium triacetoxyborohydride (600 mg) were added to this mixture and the mixture was stirred for 24 hours at RT. For working up, the mixture was concentrated and the residue was adjusted to pH 11 with five molar sodium hydroxide solution. The alkaline phase was diluted with water (10 ml) and extracted with ethyl acetate (4×20 ml). The combined extracts were dried over sodium sulfate and filtered and the filtrate was concentrated. The crude product was chromatographed over silica gel with ethyl acetate/ethanol (1:1). 490 mg N'-Indan-2-yl-N,N-dimethyl-1-phenyl-cyclohexane-1,4-diamine were obtained as a white solid which, for preparation of the hydrochloride, was dissolved in 2-butanone (10 ml), and 1.85 M ethanolic HCl (2 ml) was added. The mixture of cis- and trans-N'-indan-2-yl-N,N-dimethyl-1-phenyl-cyclohexane-1,4-diamine dihydrochloride obtained was filtered off with suction and dried (540 mg, m.p. 224-226° C.).

Example 29

N'-(9H-Fluoren-9-yl)-N,N-dimethyl-1-phenyl-cyclohexane-1,4-diamine dihydrochloride, cis/trans mixture 9-Aminofluorene (362 mg, 2 mmol) and 4-dimethylamino-4-phenylcyclohexanone (434 mg, 2 mmol) were dissolved in dry 1,2-dichloroethane (10 ml) under argon. Glacial acetic acid (2 mmol) and sodium triacetoxyborohydride (600 mg) were added to this mixture and the mixture was stirred for 24 hours at RT. For working up, the mixture was concentrated and the residue was adjusted to pH 11 with five molar sodium hydroxide solution. The alkaline phase was diluted with water (10 ml) and extracted with ethyl acetate (5×20 ml). The combined extracts were dried over sodium sulfate and filtered and the filtrate was concentrated. The crude product was chromatographed over silica gel with ethyl acetate/ethanol (1:1). 440 mg N'-(9H-fluoren-9-yl)-N,N-dimethyl-1-phenyl-cyclohexane-1,4-diamine were obtained as a white solid which, for preparation of the hydrochloride, was dissolved in 2-butanone (10 ml), and 1.85 M ethanolic HCl (1.55 ml) was added. The mixture of N'-(9H-fluoren-9-yl)-N,N-dimethyl-1-phenyl-cyclohexane-1,4-diamine dihydrochloride obtained was filtered off with suction and dried (460 mg, m.p. 202-205° C.).

Example 30

1-Benzyl-N'-(9H-fluoren-9-yl)-N,N-dimethyl-cyclohexane-1,4-diamine

1-Aminofluorene (181 mg, 1 mmol) and 4-benzyl-4-dimethylamino-cyclohexanone (231 mg, 1 mmol) were dissolved in dry 1,2-dichloroethane (10 ml) under argon. Glacial acetic acid (1 mmol) and sodium triacetoxyborohydride (300 mg) were added to this mixture and the mixture was stirred for 24 hours at RT. For working up, the mixture was concentrated and the residue was adjusted to pH 11 with five molar sodium hydroxide solution. The alkaline phase was diluted with water (10 ml) and extracted with ethyl acetate (4×20 ml). The combined extracts were dried over sodium sulfate and filtered and the filtrate was concentrated. The crude product was chromatographed over silica gel with ethyl acetate/ethanol (1:1). 150 mg 1-benzyl-N'-(9H-fluoren-9-yl)-N,N-dimethyl-cyclohexane-1,4-diamine were obtained as a white solid (m.p. 123-125° C.).

Example 31

1-Benzyl-N'-(1H-indol-3-ylmethyl)-N,N-dimethyl-cyclohexane-1,4-diamine, cis/trans mixture 292 mg C-(1H-Indol-3-yl)-methylamine were partly dissolved in dry 1,2-dichloroethane (10 ml) under argon. After addition of 463 mg 4-benzyl-4-dimethylamino-cyclohexanone (see example 3), glacial acetic acid (4 mmol) and sodium triacetoxyborohydride (550 mg), the suspension was stirred for 72 hours at room temperature. For working up, water (10 ml) was added to the reaction mixture. The organic phase was separated off and the aqueous phase was extracted twice with ether and then rendered strongly alkaline with sodium hydroxide solution. It was extracted again with ethyl acetate (4×10 ml). A pale precipitate precipitated out of the combined ethyl acetate phases even during the processing. After cooling, this was filtered off with suction, washed twice with cold ethyl acetate and dried. 235 mg 1-benzyl-N'-(1H-indol-3-ylmethyl)-N,N-dimethyl-cyclohexane-1,4-diamine were obtained as a cis/trans mixture (m.p. 194-198° C.).

Example 32

N,N-Dimethyl-N'-(1-methyl-1H-indol-3-ylmethyl)-1-phenyl-cyclohexane-1,4-diamine, cis/trans mixture 450 mg C-(1H-indol-3-yl)-methylamine were partly dissolved in dry 1,2-dichloroethane (10 ml) under argon. After addition of 609 mg 4-dimethylamino-4-phenylcyclohexanone, glacial acetic acid (5.6 mmol), sodium sulfate (2 g) and sodium triacetoxyborohydride (770 mg), the suspension was stirred for five days at room temperature. For working up, water (20 ml) was added to the reaction mixture. The organic phase was separated off and the aqueous phase was washed twice with ether (5 ml) and then rendered strongly alkaline with sodium hydroxide solution. It was extracted with ether (2×5 ml) and ethyl acetate (4×10 ml), the combined extracts were dried over sodium sulfate and filtered and the filtrate was concentrated. The crude product obtained was chromatographed over silica gel with methanol/triethylamine (100:1). 52 mg N,N-dimethyl-N'-(1-methyl-1H-indol-3-ylmethyl)-1-phenyl-cyclohexane-1,4-diamine were obtained as a cis/trans mixture.

Example 33

N,N-Dimethyl-N'-(1-methyl-1H-indol-3-ylmethyl)-1-phenyl-cyclohexane-1,4-diamine, polar diastereomer As described for example 32, 106 mg of the polar diastereomer of N,N-dimethyl-N'-(1-methyl-1H-indol-3-ylmethyl)-1-phenyl-cyclohexane-1,4-diamine were also obtained.

Example 34

N'-(2-Benzo[b]thiophen-3-yl-ethyl)-N,N-dimethyl-1-phenyl-cyclohexane-1,4-diamine dihydrochloride, cis/trans mixture Lithium aluminium hydride (1.16 g, 30.3 mmol) was suspended in dry diethyl ether (100 ml). Anhydrous aluminium chloride (4.04 g, 30.3 mmol) was introduced into this suspension under argon. After five minutes, a solution of benzo[b]thiophene-3-acetonitrile (5.25 g, 30.3 mmol) in dry diethyl ether (70 ml) was added. When the addition was complete, the mixture was heated under reflux for four days. Lithium aluminium hydride (930 mg) and aluminium chloride (500 mg) were added again to the reaction mixture and the mixture was heated under reflux for a further eight hours. For working up, it was neutralized with an aqueous solution of potassium sodium tartrate (80 ml, 20 wt. %). When the evolution of gas had ended, the phases were separated and the cloudy aqueous phase was filtered off with suction over a glass frit. The residue on the frit was washed with ethyl acetate and the clear aqueous phase was extracted with ethyl acetate (3×50 ml). The organic phases were dried over sodium sulfate and filtered and the filtrate was concentrated. Crude benzo[b]thiophen-3-ylethylamine (3.7 g) was obtained as a red-brown oil. Treatment with methanolic hydrochloric acid gave a tacky hydrochloride, which was immediately converted back into the free base. 794 mg (15%) benzo[b]thiophen-3-yl-ethylamine were obtained as a yellow oil, which was employed for the further synthesis.

Benzo[b]thiophen-3-yl-ethylamine (289 mg, 1.6 mmol) was dissolved in dry 1,2-dichloroethane (10 ml) under argon and, after addition of 4-dimethylamino-4-phenylcyclohexanone (354 mg, 1.6 mmol) and sodium sulfate (2 g), the mixture was stirred for one hour at RT. Sodium triacetoxyborohydride (440 mg, 2.0 mmol) was then added to the reaction mixture in one portion. After 3 days, glacial acetic acid (4 mmol) was subsequently added and the mixture was stirred for a further 24 hours at RT. For working up, water (20 ml) was added and the reaction mixture was filtered with suction. The solid obtained was dissolved with two molar sodium carbonate solution and ethyl acetate. The organic phase was separated off, dried over sodium sulfate and filtered and the filtrate concentrated. The solid but tacky residue obtained (213 mg) was dissolved in 2-butanone (5 ml), and ethanolic HCl (500 µl, 1.5 mmol) was added at RT. After two hours, the solution was concentrated to dryness and the residue was suspended in diethyl ether (5 ml), filtered off with suction and rinsed with diethyl ether (3×3 ml). A mixture of cis- and trans-N'-(2-benzo[b]thiophen-3-yl-ethyl)-N,N-dimethyl-1-phenyl-cyclohexane-1,4-diamine dihydrochloride (217 mg, m.p. 164-167° C.) was obtained as a beige-brown solid.

Example 35

N'-(2-Benzo[b]thiophen-3-yl-ethyl)-1-benzyl-N,N-dimethyl-cyclohexane-1,4-diamine dihydrochloride, cis/trans mixture Benzo[b]thiophen-3-ylethylamine (350 mg, 1.9 mmol) was dissolved in dry 1,2-dichloroethane (10 ml) under argon and, after addition of 4-benzyl-4-dimethylamino-cyclohexanone (463 mg, 2 mmol), glacial acetic acid (2 mmol) and anhydrous sodium sulfate (2 g), the mixture was stirred for one hour at RT. Sodium triacetoxyborohydride (550 mg, 2.5 mmol) was then added in one portion and the mixture was stirred for four days at RT. For working up, the mixture was diluted with 1,2-dichloroethane (10 ml) and water (15 ml). The precipitate which remained was filtered off with suction (379 mg, m.p. 225-233° C.). By extraction of the aqueous phase, which had been adjusted to pH 11 with five molar sodium hydroxide solution, with ethyl acetate, 353 mg of a yellow oil were obtained. From the two part amounts, it was possible, by renewed dissolving in dilute hydrochloric acid, extraction with diethyl ether (2×15 ml) and subsequent adjustment of the aqueous phase to pH 11 with five molar sodium hydroxide solution and extraction with ethyl acetate (3×20 ml) for the crude product (438 mg, viscous oil) to be isolated. 366 mg of the diastereoisomer mixture obtained were dissolved in 2-butanone (30 ml), and ethanolic hydrochloric acid (847 µl, 2.8 mmol) was added at RT. A precipitate formed, which rapidly dissolved again and precipitated out again during the after-stirring time (four days at RT). After a further thirty minutes in the refrigerator, the precipitate was filtered off with suction, washed with cold 2-butanone (3×3 ml) and dried. The pale yellow solid obtained was a mixture of cis- and trans-N'-(2-benzo[b]thiophen-3-yl-ethyl)-1-benzyl-N,N-dimethyl-cyclohexane-1,4-diamine dihydrochloride (338 mg, m.p. 225-229° C.).

Example 36

N'-Acenaphthen-1-yl-N,N-dimethyl-1-phenyl-cyclohexane-1,4-diamine dihydrochloride, polar diastereomer 339 mg Acenaphthen-1-ylamine and 435 mg 4-dimethylamino-4-phenyl-cyclohexanone were dissolved in dry 1,2-dichloroethane (20 ml) under argon. Glacial acetic acid (2 mmol) and 600 mg sodium triacetoxyborohydride were added to this mixture and the mixture was stirred for 24 hours at RT. For working up, the reaction mixture was concentrated and the residue was adjusted to pH 11 with five molar sodium hydroxide solution. The alkaline phase was diluted with water (10 ml) and extracted with ethyl acetate (4×20 ml). The combined extracts were dried over sodium sulfate, filtered and concentrated. The crude product was chromatographed over silica gel with ethyl acetate/ethanol (1:1). 130 mg of the polar diastereomer of N'-acenaphthen-1-yl-N,N-dimethyl-1-phenyl-cyclohexane-1,4-diamine were obtained as a white solid, from which the corresponding dihydrochloride was precipitated with 1.85 M ethanolic hydrochloric acid (0.5 ml) in 2-butanone (5 ml) (151 mg; m.p. 214-216° C.).

Example 37

N'-Acenaphthen-1-yl-N,N-dimethyl-1-phenyl-cyclohexane-1,4-diamine dihydrochloride, nonpolar diastereomer As described for example 36, 250 mg of the nonpolar diastereomer of N'-acenaphthen-1-yl-N,N-dimethyl-1-phenyl-cyclohexane-1,4-diamine were also obtained as a white solid, from which the corresponding dihydrochloride was precipitated with 1.85 M ethanolic hydrochloric acid (0.9 ml) in 2-butanone (10 ml) (300 mg; m.p. 190-192° C.).

Example 38

N'-Benzo[b]thiophen-5-yl-1-benzyl-N,N-dimethyl-cyclohexane-1,4-diamine dihydrochloride, nonpolar diastereomer 300 mg 5-Aminobenzothiophene and 463 mg 4-benzyl-4-dimethylamino-cyclohexanone were dissolved in dry 1.2-dichloroethane (20 ml) under argon. Glacial acetic acid (2 mmol) and 600 mg sodium triacetoxyborohydride were added to this mixture and the mixture was stirred for 24 hours at RT. For working up, the reaction mixture was concentrated and the residue was adjusted to pH 11 with five molar sodium hydroxide solution. The alkaline phase was diluted with water (10 ml) and extracted with ethyl acetate (6×20 ml). The combined extracts were dried over sodium sulfate and filtered and the filtrate was concentrated. The crude product was chromatographed over silica gel with ethyl acetate/ethanol (1:1). 520 mg of the nonpolar diastereomer of N'-benzo[b]thiophen-5-yl-1-benzyl-N,N-dimethyl-cyclohexane-1,4-diamine were obtained as a white solid, from which the corresponding dihydrochloride was precipitated with 1.85 M ethanolic hydrochloric acid (1.93 ml) in 2-butanone (15 ml) (621 mg; m.p. 140-142° C.).

Example 39

N'-Benzo[b]thiophen-5-yl-N,N-dimethyl-1-phenyl-cyclohexane-1,4-diamine hydrochloride, nonpolar diastereomer 300 mg 5-Aminobenzothiophene and 435 mg 4-dimethylamino-4-phenyl-cyclohexanone were dissolved in dry 1,2-dichloroethane (20 ml) under argon. Glacial acetic acid (2 mmol) and 600 mg sodium triacetoxyborohydride were added to this mixture and the mixture was stirred for 24 hours at RT. For working up, the reaction mixture was concentrated and the residue was adjusted to pH 11 with five molar sodium hydroxide solution. The alkaline phase was diluted with water (10 ml) and extracted with ethyl acetate (3×20 ml). The combined extracts were dried over sodium sulfate and filtered and the filtrate was concentrated. The crude product was chromatographed over silica gel with ethyl acetate/ethanol (1:1). 230 mg of the nonpolar diastereomer of N'-benzo[b]thiophen-5-yl-N,N-dimethyl-1-phenyl-cyclohexane-1,4-diamine were obtained as a white solid, from which the corresponding hydrochloride was precipitated with 1.85 M ethanolic hydrochloric acid (0.54 ml) in 2-butanone (8 ml) (243 mg; m.p. 155-157° C.).

Example 40

N'-Benzothiazol-6-yl-N,N-dimethyl-1-phenyl-cyclohexane-1,4-diamine dihydrochloride, nonpolar diastereomer 300 mg 6-Aminobenzothiazole and 435 mg 4-dimethylamino-4-phenyl-cyclohexanone were dissolved in dry 1,2-dichloroethane (20 ml) under argon. Glacial acetic acid (2 mmol) and 600 mg sodium triacetoxyborohydride were added to this mixture and the mixture was stirred for 24 hours at RT. For working up, the reaction mixture was concentrated and the residue was adjusted to pH 11 with five molar sodium hydroxide solution. The alkaline phase was diluted with water (10 ml) and extracted with ethyl acetate (3×20 ml). The combined extracts were dried over sodium sulfate and filtered and the filtrate was concentrated. The crude product was chromatographed over silica gel with ethyl acetate/ethanol (1:1). 220 mg of the nonpolar diastereomer of N'-benzothiazol-6-yl-N,N-dimethyl-1-phenyl-cyclohexane-1,4-diamine were obtained as a yellow solid, from which the corresponding dihydrochloride was precipitated with 1.85 M ethanolic hydrochloric acid (0.83 ml) in 2-butanone (10 ml) (197 mg; m.p. 144-147° C.).

Example 41

N'-Benzo[1,2,5]thiadiazol-4-yl-N,N-dimethyl-1-phenyl-cyclohexane-1,4-diamine dihydrochloride, polar diastereomer 302 mg Benzo[1,2,5]thiadiazol-4-ylamine and 435 mg 4-dimethylamino-4-phenyl-cyclohexanone were dissolved in dry 1,2-dichloroethane (20 ml) under argon. Glacial acetic acid (2 mmol) and 600 mg sodium triacetoxyborohydride were added to this mixture and the mixture was stirred for 24 hours at RT. For working up, the reaction mixture was concentrated and the residue was adjusted to pH 11 with five molar sodium hydroxide solution. The alkaline phase was diluted with water (10 ml) and extracted with ethyl acetate (3×20 ml). The combined extracts were dried over sodium sulfate and filtered and the filtrate was concentrated. The crude product was chromatographed over silica gel with ethyl acetate/ethanol (1:1). 40 mg of the polar diastereomer of N'-benzo[1,2,5]thiadiazol-4-yl-N,N-dimethyl-1-phenyl-cyclohexane-1,4-diamine were obtained as a red solid, from which the corresponding hydrochloride was precipitated with 1.85 M ethanolic hydrochloric acid (0.15 ml) in 2-butanone (2 ml) (35 mg; m.p. 122-125° C.).

Example 42

N'-[2-(1H-Indol-3-yl)-1-methyl-ethyl]-N,N-dimethyl-1-phenyl-cyclohexane-1,4-diamine dihydrochloride, nonpolar diastereomer DL-α-Methyltryptamine (3.00 g, 17.2 mmol) was dissolved in dry 1,2-dichloroethane (10 ml) under argon. After addition of 4-dimethylamino-4-phenyl-cyclohexanone (3.70 g) and glacial acetic acid (1.5 ml) the mixture was stirred for one hour at RT. Sodium triacetoxyborohydride (4.7 g) was then added and the suspension was stirred for four days at RT. For working up, 1,2-dichloroethane (20 ml) and water (50 ml) were added to the reaction mixture. The clear phases were separated and the aqueous phase was washed with ether (2×20 ml) and then rendered strongly alkaline with five molar sodium hydroxide solution. The aqueous phase was extracted with ethyl acetate (5×30 ml), the combined extracts were dried over sodium sulfate and filtered and the filtrate was concentrated. The crude product obtained (5.8 g of a beige-brown solid) was first coarsely fractionated over silica gel with methanol/triethylamine (199:1) and then finely purified again. 1.20 g of the nonpolar diastereomer of N'-[2-(1H-indol-3-yl)-1-methyl-ethyl]-N,N-dimethyl-1-phenyl-cyclohexane-1,4-diamine were obtained (m.p. 158-160° C.). From 1 g of this compound, the corresponding dihydrochloride was precipitated with chlorotrimethylsilane (840 µl) in 2-butanone/acetone (100 ml/30 ml) (977 mg; m.p. 170-174° C.).

Example 43

N'-Adamantan-2-yl-N,N-dimethyl-1-phenyl-cyclohexane-1,4-diamine dihydrochloride 302 mg 2-Adamantylamine and 434 mg 4-dimethylamino-4-phenyl-cyclohexanone were dissolved in dry tetrahydrofuran (15 ml) and 1,2-dichloroethane (5 ml) under argon. 600 mg sodium triacetoxyborohydride were added to this mixture and the mixture was stirred for 23 hours at RT. For working up, the reaction mixture was concentrated and the residue washed with one molar hydrochloric acid (20 ml) and ether (40 ml). The aqueous phase was washed with ether (2×20 ml), rendered alkaline with five molar sodium hydroxide solution and extracted with ether (3×30 ml). The combined extracts were dried over sodium sulfate and filtered and the filtrate was concentrated. The crude product was chromatographed over silica gel with ethyl acetate/methanol (4:1). 130 mg N'-Adamantan-2-yl-N,N-dimethyl-1-phenyl-cyclohexane-1,4-diamine were obtained as a beige-colored solid, from which the corresponding dihydrochloride (132 mg), which decomposed on heating from 237° C., was precipitated with 3.3 M ethanolic hydrochloric acid (0.34 ml) in 2-butanone (6 ml).

Example 44

N'-(9-Ethyl-9H-carbazol-3-yl)-N,N-dimethyl-1-phenyl-cyclohexane-1,4-diamine dihydrochloride, nonpolar diastereomer 421 mg 3-Amino-9-ethylcarbazole and 435 mg 4-dimethylamino-4-phenyl-cyclohexanone were dissolved in dry 1,2-dichloroethane (20 ml) under argon. Glacial acetic acid (2 mmol) and 600 mg sodium triacetoxyborohydride were added to this mixture and the mixture was stirred for 24 hours at RT. For working up, the reaction mixture was concentrated and the residue was adjusted to pH 11 with five molar sodium hydroxide solution. The alkaline phase was diluted with water (10 ml) and extracted with ethyl acetate (3×20 ml). The combined extracts were dried over sodium sulfate and filtered and the filtrate was concentrated. The crude product was chromatographed over silica gel with ethyl acetate/ethanol (1:1). 288 mg of the nonpolar diastereomer of N'-(9-ethyl-9H-carbazol-3-yl)-N,N-dimethyl-1-phenyl-cyclohexane-1,4-diamine were obtained as a brown solid, from which the corresponding dihydrochloride was precipitated with 1.85 M ethanolic hydrochloric acid (0.95 ml) in 2-butanone (10 ml) (339 mg; m.p. 145-150° C.).

Example 45

N'-(3H-Benzotriazol-5-yl)-N,N-dimethyl-1-phenyl-cyclohexane-1,4-diamine hydrochloride, nonpolar diastereomer 268 mg 5-Aminobenzotriazole and 435 mg 4-dimethylamino-4-phenyl-cyclohexanone were dissolved in dry 1,2-dichloroethane (20 ml) under argon. Glacial acetic acid (2 mmol) and 600 mg sodium triacetoxyborohydride were added to this mixture and the mixture was stirred for 24 hours at RT. For working up, the reaction mixture was concentrated and the residue was adjusted to pH 11 with five molar sodium hydroxide solution. The alkaline phase was diluted with water (10 ml) and extracted with ethyl acetate (3×20 ml). The combined extracts were dried over sodium sulfate and filtered and the filtrate was concentrated. The crude product was chromatographed over silica gel with ethyl acetate/ethanol (1:1). 135 mg of the nonpolar diastereomer of N'-(3H-benzotriazol-5-yl)-N,N-dimethyl-1-phenyl-cyclohexane-1,4-diamine were obtained as a white solid, from which the corresponding hydrochloride was precipitated with 1.85 M ethanolic hydrochloric acid (0.54 ml) in 2-butanone (5 ml) (98 mg; m.p. 168-173° C.).

Example 46

N'-(3H-Benzotriazol-5-yl)-N,N-dimethyl-1-phenyl-cyclohexane-1,4-diamine hydrochloride, polar diastereomer As described for example 45, 122 mg of the polar diastereomer of N'-(3H-benzotriazol-5-yl)-N,N-dimethyl-1-phenyl-cyclohexane-1,4-diamine were also obtained as a white solid, from which the corresponding dihydrochloride was precipitated with 1.85 M ethanolic hydrochloric acid (0.5 ml) in 2-butanone (5 ml) (119 mg; m.p. 185-189° C.).

Example 47

N'-(9H-Fluoren-9-yl)-N,N-dimethyl-1-thiophen-2-yl-cyclohexane-1,4-diamine dihydrochloride, cis/trans mixture 2-Iodothiophene (22.9 g) was dissolved in THF (80 ml) under argon, and 2M isopropylmagnesium chloride (35.7 ml) in THF was added thereto at 0° C. in the course of 30 minutes. After a reaction time of one hour at 3-5° C., 8-dimethylamino-1,4-dioxa-spiro[4.5]decane-8-carbonitrile (10 g), dissolved in tetrahydrofuran (20 ml), was added and stirring was carried out for 20 hours at room temperature. For working up, saturated NH$_4$Cl solution (85 ml) was added, the mixture was extracted with diethyl ether (3×100 ml), and the combined extracts were washed with water (50 ml) and saturated NaCl solution (50 ml), dried and concentrated. The crude product obtained (21.3 g of dark brown oil) was dissolved in 2-butanone (140 ml) and converted with chlorotrimethylsilane (9.1 ml) into the hydrochloride of dimethyl-(8-thiophen-2-yl-1,4-dioxa-spiro[4.5]dec-8-yl)-amine (white solid; 8.74 g).

Dimethyl-(8-thiophen-2-yl-1,4-dioxa-spiro[4.5]dec-8-yl)-amine hydrochloride (8.68 g) was dissolved in 7.5M hydrochloric acid (29 ml), stirred for 48 hours at room temperature and then extracted with diethyl ether (2×50 ml). The aqueous phase was rendered alkaline with 5M sodium hydroxide solution, while cooling with ice, extracted with dichloromethane (3×50 ml), dried and concentrated. 4-Dimethylamino-4-thiophen-2-yl-cyclohexanone was obtained as a yellow solid (5.66 g; m.p. 108-110° C.).

362 mg 9-Aminofluorene and 434 mg 4-dimethylamino-4-thiophen-2-yl-cyclohexanone were dissolved in dry 1,2-dichloroethane (10 ml) under argon. Glacial acetic acid (2 mmol) and 600 mg sodium triacetoxyborohydride were added to this mixture and the mixture was stirred for 24 hours at RT. For working up, the reaction mixture was concentrated and the residue was adjusted to pH 11 with five molar sodium hydroxide solution. The alkaline phase was diluted with water (10 ml) and extracted with ethyl acetate (5×20 ml). The combined extracts were dried over sodium sulfate and filtered and the filtrate was concentrated. The crude product was chromatographed over silica gel with ethyl acetate/ethanol (1:1). 440 mg of a cis/trans mixture of N'-(9H-fluoren-9-yl)-N,N-dimethyl-1-thiophen-2-yl-cyclohexane-1,4-diamine were obtained as a white solid, from which the corresponding dihydrochloride was precipitated with 1.85 Methanolic hydrochloric acid (1.55 ml) in 2-butanone (10 ml) (460 mg; m.p. 202-205° C.).

Example 48

N'-Cyclooctyl-N,N-dimethyl-1-phenyl-cyclohexane-1,4-diamine dihydrochloride 254 mg Cyclooctylamine and 434 mg 4-dimethylamino-4-phenyl-cyclohexanone were dissolved in dry tetrahydrofuran (15 ml) and 1,2-dichloroethane (5 ml) under argon. Glacial acetic acid (120 mg) and 600 mg sodium triacetoxyborohydride were added to this mixture and the mixture was stirred for 18 hours at RT. For working up, the reaction mixture was concentrated and the residue was washed with one molar hydrochloric acid (20 ml) and with ether (2×30 ml). The aqueous phase was rendered alkaline with five molar sodium hydroxide solution and extracted with ether (3×30 ml). The combined extracts were dried over sodium sulfate and filtered and the filtrate was concentrated. The crude product (515 mg) was chromatographed over silica gel with methanol. 108 mg N'-cyclooctyl-N,N-dimethyl-1-phenyl-cyclohexane-1,4-diamine were obtained as a colorless oil, from which the corresponding dihydrochloride was precipitated with 3.3 M ethanolic hydrochloric acid (0.25 ml) in 2-butanone (2 ml) (102 mg; m.p. 247-249° C.).

Example 49

N'-(1H-Indol-3-ylmethyl)-N,N-dimethyl-1-phenyl-cyclohexane-1,4-diamine dihydrochloride, nonpolar diastereomer 970 mg C-(1H-Indol-3-yl)methylamine and 1.44 mg 4-dimethylamino-4-phenyl-cyclohexanone were dissolved in dry tetrahydrofuran (15 ml) and 1,2-dichloroethane (50 ml) under argon. Glacial acetic acid (13.2 mmol) and 1.82 g sodium triacetoxyborohydride were added to this mixture and the mixture was stirred for 72 hours at RT. For working up, the reaction mixture was concentrated, water (20 ml) and ether (30 ml) were added to the residue and the mixture was stirred vigorously. The aqueous phase was separated off, washed with ether (2×15 ml), adjusted to pH 11 with five molar sodium hydroxide solution and extracted with ethyl acetate (4×25 ml). The combined extracts were dried over sodium sulfate and filtered and the filtrate was concentrated. The crude product (2.11 g) was chromatographed over silica gel with methanol/triethylamine (199:1). 465 mg of the nonpolar diastereomer of N'-(1H-indol-3-ylmethyl)-N,N- dimethyl-1-phenyl-cyclohexane-1,4-diamine were obtained (m.p. 182-184° C.), from which the corresponding dihydrochloride was precipitated with chlorotrimethylsilane (443 µl) in 2-butanone/acetone (20 ml/50 ml) (498 mg; m.p. 164-168° C.).

Example 50

N'-(1H-Indol-3-ylmethyl)-N,N-dimethyl-1-phenyl-cyclohexane-1,4-diamine dihydrochloride, polar diastereomer As described for example 49, 360 mg of the polar diastereomer of N'-(1H-indol-3-ylmethyl)-N,N-dimethyl-1-phenyl-cyclohexane-1,4-diamine were also obtained, from which the corresponding dihydrochloride was precipitated with chlorotrimethylsilane (328 µl) in 2-butanone/acetone (10 ml/25 ml) (435 mg; m.p. 185-188° C.).

Example 51

N'-Benzo[b]thiophen-3-ylmethyl-N,N-dimethyl-1-phenyl-cyclohexane-1,4-diamine dihydrochloride, nonpolar diastereomer Benzothiophene-3-carbaldehyde (4.0 g, 24.6 mmol) was dissolved in a mixture of pyridine (25 ml) and ethanol (25 ml). Hydroxylamine hydrochloride (3.4 g, 49.2 mmol) was added, while stirring. The mixture was stirred for 30 minutes at RT and then heated under reflux for eight hours. A red-brown solution formed. For working up, the solution was concentrated and the residue was freed from residual pyridine by distillation with ethanol (3×50 ml). Water (50 ml) was added to the oily residue and the mixture was stirred vigorously overnight. The pink solid present was filtered off with suction, washed with water and dried in vacuo. 4.3 g benzothiophene-3-carbaldehyde oxime were obtained (m.p. 87-89° C.).

Benzothiophene-3-carbaldehyde oxime (3.96 g, 22.3 mmol) was dissolved in methanol (100 ml) and five molar sodium hydroxide solution (100 ml), and Devarda alloy (14.1 g) was added in portions under argon. Heating and evolution of hydrogen occurred here. The mixture was stirred for 16 hours. Working up was carried out by slow addition of water (100 ml), a vigorous reaction starting again. The mixture was filtered over Celite, the methanol was removed in vacuo and the aqueous phase which remained was extracted with diethyl ether (3×50 ml). After concentration of the organic phase, 1.43 g C-benzo[b] thiophen-3-yl-methylamine remained as a green oil. 3.3 M ethanolic hydrochloric acid (3.6 ml, 12 mmol) was added to a solution of this amine (1.3 g, 8 mmol) in 2-butanone (5 ml), 1.18 g C-benzo[b]thiophen-3-yl-methylamine hydrochloride precipitating out as a white crystalline solid with a melting point of 254-256° C.

449 mg C-benzo[b]thiophen-3-yl-methylamine and 434 mg 4-dimethylamino-4-phenyl-cyclohexanone were dissolved in dry tetrahydrofuran (20 ml) and 1,2-dichloroethane (7 ml) under argon. Glacial acetic acid (165 mg) and 825 mg sodium triacetoxyborohydride were added to this mixture and the mixture was stirred for 41 hours at RT. For working up, the reaction mixture was concentrated and the residue was washed with one molar hydrochloric acid (20 ml) and with ether (2×20 ml). The aqueous phase was adjusted to pH 8-9 with one molar sodium hydroxide solution and extracted with ether (3×20 ml). The combined extracts were dried over sodium sulfate and filtered and the filtrate was concentrated. The yellow crystalline crude product (787 mg) was dissolved in methanol (7 ml) for chromatographic separation, the nonpolar diastereomer precipitating out. 247 mg of the nonpolar diastereomer of N'-benzo [b]thiophen-3-ylmethyl-N,N-dimethyl-1-phenyl-cyclohexane-1,4-diamine were obtained as a white solid (m.p. 138-140° C.), from which the corresponding dihydrochloride was precipitated with 3.3 M ethanolic hydrochloric acid (0.8 ml) in 2-butanone (25 ml) (187 mg; m.p. 225-230° C.).

Example 52

N'-Benzo[b]thiophen-3-ylmethyl-N,N-dimethyl-1-phenyl-cyclohexane-1,4-diamine dihydrochloride, polar diastereomer As described for example 51, the methanolic solution of the crude product was chromatographed over silica gel with methanol. 113 mg of the polar diastereomer of N'-benzo[b] thiophen-3-ylmethyl-N,N-dimethyl-1-phenyl-cyclohexane-1,4-diamine were obtained as a colorless oil, from which the corresponding dihydrochloride was precipitated as a white solid with 3.3 M ethanolic hydrochloric acid (0.28 ml) in 2-butanone (10 ml) (120 mg; m.p. 252-254° C.).

Example 53

N'-Anthracen-2-yl-N,N-dimethyl-1-phenyl-cyclo-hexane-1,4-diamine hydrochloride, nonpolar diastereomer 386 mg 2-Aminoanthracene and 434 mg 4-dimethylamino-4-phenyl-cyclohexanone were dissolved in dry 1,2-dichloroethane (20 ml) under argon. Glacial acetic acid (2 mmol) and 600 mg sodium triacetoxyborohydride were added to this mixture and the mixture was stirred for 24 hours at RT. For working up, the reaction mixture was concentrated and the residue was adjusted to pH 11 with five molar sodium hydroxide solution and extracted with ethyl acetate (4×20 ml). The combined extracts were dried over sodium sulfate and filtered and the filtrate was concentrated. The crude products was chromatographed over silica gel with ethyl acetate/ethanol (1:1). 132 mg of the nonpolar diastereomer of N'-anthracen-2-yl-N,N-dimethyl-1-phenyl-cyclohexane-1,4-diamine were obtained as a green solid, from which the corresponding hydrochloride was precipitated with 1.85 M ethanolic hydrochloric acid (0.46 ml) in 2-butanone (5 ml) (104 mg; m.p. 169-172° C.).

Example 54

N'-Benzo[b]thiophen-3-ylmethyl-1-benzyl-N,N-dimethyl-cyclohexane-1,4-diamine dihydrochloride, nonpolar diastereomer 391 mg C-benzo[b]thiophen-3-yl-methylamine and 554 mg 4-benzyl-4-dimethylamino-cyclohexanone were dissolved in dry tetrahydrofuran (18 ml) and 1,2-dichloroethane (6 ml) under argon. Glacial acetic acid (144 mg) and 720 mg sodium triacetoxyborohydride were added to this mixture and the mixture was stirred for 22 hours at RT. For working up, the reaction mixture was concentrated, the residue was taken up in one molar hydrochloric acid (20 ml) and the mixture was washed with ether (2×20 ml). The aqueous phase was adjusted to pH 8-9 with one molar sodium hydroxide solution and extracted with ether (3×20 ml). The combined extracts were dried over sodium sulfate and filtered and the filtrate was concentrated. The pale yellow oil obtained (904 mg) was chromatographed over silica gel with methanol. 368 mg of the nonpolar diastereomer of N'-benzo[b]thiophen-3-ylmethyl-1-benzyl-N,N-dimethyl-cyclohexane-1,4-diamine were obtained, from which the corresponding dihydrochloride was precipitated with 3.3 M ethanolic hydrochloric acid (0.88 ml) in 2-butanone (25 ml) (364 mg; m.p. 246-255° C.).

Example 55

N'-Benzo[b]thiophen-3-ylmethyl-1-benzyl-N,N-dimethyl-cyclohexane-1,4-diamine dihydrochloride, polar diastereomer As described for example 54, 347 mg of the polar diastereomer of N'-benzo[b]thiophen-3-ylmethyl-1-benzyl-N,N-dimethyl-cyclohexane-1,4-diamine were also obtained, from which the corresponding dihydrochloride was precipitated with 3.3 M ethanolic hydrochloric acid (0.83 ml) in 2-butanone (25 ml) (418 mg; m.p. 242-248° C.).

Example 56

N'-[2-(1H-Indol-3-yl)-ethyl]-N,N-dimethyl-1-naphthalen-2-yl-cyclohexane-1,4-diamine dihydrochloride, nonpolar diastereomer A Grignard solution was prepared in dry tetrahydrofuran (65 ml) from magnesium (2.05 g) and 2-bromonaphthalene (17.7 g). This Grignard solution was stirred for a further one hour at boiling temperature. 8-Dimethylamino-1,4-dioxa-spiro[4.5]decane-8-carbonitrile (9.0 g) dissolved in dry tetrahydrofuran (70 ml) was then added dropwise at RT and the mixture was stirred overnight at RT. When the reaction was complete, the batch was quenched with saturated ammonium chloride solution, while cooling with ice, extracted with diethyl ether (2×70 ml), dried over $Na_2SO_4$ and concentrated. For working up, the crude product (24.2 g) was dissolved in 2-butanone (130 ml), and $Me_3SiCl$ (14.8 ml) was added thereto while cooling with ice. After six hours, the dimethyl-(8-naphthalen-2-yl-1,4-dioxa-spiro[4.5]dec-8-yl)-amine which had precipitated out was filtered off with suction (white solid; 6.09 g).

Dimethyl-(8-naphthalen-2-yl-1,4-dioxa-spiro[4.5]dec-8-yl)-amine hydrochloride (6.09 g) was dissolved in 7.5N hydrochloric acid, stirred for 32 hours at RT and then extracted with diethyl ether (3×30 ml). The aqueous phase was rendered alkaline with 25% ammonia solution, while cooling with ice, and extracted with 1,2-dichloroethane (3×30 ml). The combined extracts were dried with $Na_2SO_4$ and concentrated. 4.48 g of 4-dimethylamino-4-naphthalen-2-yl-cyclohexanone were obtained as a white solid (m.p. 81-83° C.).

The dihydrochloride of the nonpolar diastereomer of N'-[2-(1H-indol-3-yl)-ethyl]-N,N-dimethyl-1-naphthalen-2-yl-cyclohexane-1,4-diamine was obtained analogously to the examples described above by reductive amination of 4-dimethylamino-4-naphthalen-2-yl-cyclohexanone with tryptamine.

Example 57

N'-[2-(1H-Indol-3-yl)-ethyl]-N,N-dimethyl-1-phenyl-cyclohexane-1,4-diamine dihydrochloride, nonpolar diastereomer 1.12 g tryptamine and 1.52 g 4-dimethylamino-4-phenyl-cyclohexanone were dissolved in dry tetrahydrofuran (12 ml) and 1,2-dichloroethane (40 ml) under argon. Glacial acetic acid (801 µl) and 1.92 g sodium triacetoxyborohydride were added to this mixture and the mixture was stirred for four days at RT. For working up, the reaction mixture was concentrated and the residue was taken up in water (20 ml), two molar hydrochloric acid (5 ml) and ether (35 ml). The aqueous phase was separated off, washed with ether (2×15 ml), adjusted to pH 11 with sodium hydroxide solution and extracted with ethyl acetate (3×20 ml). The combined extracts were dried over sodium sulfate and filtered and the filtrate was concentrated. The beige-brown residue obtained (2.0 g) was chromatographed over silica gel with methanol which contained 0.75 vol. % triethylamine. 553 mg of the nonpolar diastereomer of N'-[2-(1H-indol-3-yl)-ethyl]-N,N-dimethyl-1-phenyl-cyclohexane-1,4-diamine were obtained (m.p. 175-178° C.), from which the corresponding dihydrochloride was obtained with chlorotrimethylsilane in 2-butanone/acetone (20 ml/50 ml) (600 mg; m.p. 216-218° C.).

Example 58

N'-[2-(1H-Indol-3-yl)-ethyl]-N,N-dimethyl-1-phenyl-cyclohexane-1,4-diamine dihydrochloride, polar diastereomer As described for example 57, 546 mg of the polar diastereomer of N'-[2-(1H-indol-3-yl)-ethyl]-N,N-dimethyl-1-phenyl-cyclohexane-1,4-diamine were also obtained (m.p. 175-180° C.), from which the corresponding dihydrochloride was obtained with chlorotrimethylsilane (573 µl) in 2-butanone/acetone (3 ml/30 ml) (520 mg; m.p. 223-229° C.).

Example 59

N'-[2-(1H-Indol-3-yl)-1-methyl-ethyl]-N,N-dimethyl-1-phenyl-cyclohexane-1,4-diamine dihydrochloride, polar diastereomer As described for example 42, 546 mg of the polar diastereomer of N'-[2-(1H-indol-3-yl)-1-methyl-ethyl]-N,N-dimethyl-1-phenyl-cyclohexane-1,4-diamine were also obtained (m.p. 50-55° C.), from which the corresponding dihydrochloride was obtained as a pale pink solid with chlorotrimethylsilane (1.0 ml) in 2-butanone (50 ml) (1.1 g; m.p. 194-199° C.).

Example 60

Methyl 2-(4-dimethylamino-4-phenyl-cyclohexylamino)-3-(1H-indol-3-yl)-propionate dihydrochloride, nonpolar diastereomer 4-Dimethylamino-4-phenylcyclohexanone (435 mg, 2 mmol.), glacial acetic acid (57 µl, 1 mmol.) and red-hot sodium sulfate (2 g) were added to L-tryptophan methyl ester (438 mg, 2 mmol.) in 1,2-dichloroethane (20 ml). After two hours' stirring at RT, sodium triacetoxyborohydride (660 mg, 3 mmol.) was added and stirring was continued.

After 3 days, the reaction mixture was concentrated and the residue was suspended in diethyl ether (20 ml) and 1M NaOH (5 ml). After extraction of the aqueous phase with diethyl ether and ethyl acetate (in each case 3×10 ml), the combined organic phases were washed twice in a separating funnel with 1M NaOH (5 ml), dried and concentrated. The viscous residue (718 mg) was purified by flash chromatography twice [50 g silica gel, eluant: ethyl acetate/methanol (3:1) and also ethyl acetate/MeOH (1:1)] and the diastereomers were separated thereby. 270 mg of the nonpolar diastereomer of methyl 2-(4-dimethylamino-4-phenyl-cyclohexylamino)-3-(1H-indol-3-yl)-propionate were obtained, from which the corresponding dihydrochloride was obtained as a white solid with chlorotrimethylsilane (244 µl) in 2-butanone/acetone (8 ml/4 ml) (291 mg, m.p. 175-180° C.).

Example 61

Methyl 2-(4-dimethylamino-4-phenyl-cyclohexylamino)-3-(1H-indol-3-yl)-propionate dihydrochloride, polar diastereomer As described for example 60, (140 mg, m.p. 60-65° C.) of the polar diastereomer of methyl 2-(4-dimethylamino-4-phenyl-cyclohexylamino)-3-(1H-indol-3-yl)-propionate were also obtained, from which the corresponding dihydrochloride was obtained as a white solid with chlorotrimethylsilane (126 µl) in 2-butanone/acetone (7 ml/3 ml) (129 mg; 180-185° C.).

Example 62

N'-[2-(1H-Indol-3-yl)-1-methyl-ethyl]-N,N-dimethyl-1-naphthalen-2-yl-cyclohexane-1,4-diamine dihydrochloride, nonpolar diastereomer 4-Dimethylamino-4-naphthalen-2-yl-cyclohexanone (534 mg) and DL-α-methyltryptamine (348 mg) were dissolved in a mixture of tetrahydrofuran (20 ml) and 1,2-dichloroethane (5 ml) under argon. Acetic acid (120 mg) was added and, after a reaction time of 15 minutes, sodium triacetoxyborohydride (600 mg) was added thereto. After 64 hours, the reaction mixture was filtered with suction. After taking up the white solid obtained in 1M sodium hydroxide solution (20 ml), extraction with diethyl ether (3×20 ml) and concentration of the dried combined extracts, an oily residue (520 mg) was obtained. Separation of the mixture by chromatography was effected first with methanol, yielding 295 mg (m.p. 68-70° C.) of the nonpolar diastereomer as a white solid. The nonpolar diamine was dissolved in 2-butanone (5 ml), and 3.3N ethanolic hydrochloric acid (0.52 ml) was added thereto, an oily solid precipitating out. After concentration of the reaction mixture and addition of diethyl ether, the crystalline dihydrochloride of the nonpolar diastereomer of N'-[2-(1H-indol-3-yl)-1-methyl-ethyl]-N,N-dimethyl-1-naphthalen-2-yl-cyclohexane-1,4-diamine was obtained (319 mg; m.p. 206-210° C.).

Example 63

N'-Benzo[1,3]dioxol-5-ylmethyl-N,N-dimethyl-1-phenyl-cyclohexane-1,4-diamine dihydrochloride, cis/trans mixture 3,4-(Methylenedioxy)benzylamine (250 µl) and 4-dimethylamino-4-phenylcyclohexanone (434 mg) were dissolved in dry 1,2-dichloroethane (10 ml) with the exclusion of oxygen. Glacial acetic acid (2 mmol.) and sodium triacetoxyborohydride (600 mg) were added to this mixture. Stirring was then carried out for 24 hours at RT. For working up, the mixture was concentrated, adjusted to pH 11 with 5M NaOH, diluted with water (10 ml) and extracted with ethyl acetate (4×20 ml). The combined organic extracts were dried with $Na_2SO_4$ and concentrated. The colorless oil obtained (795 mg) was dissolved in 2-butanone (13 ml), and the dihydrochloride of N'-benzo[1,3]dioxol-5-ylmethyl-N,N-dimethyl-1-phenyl-cyclohexane-1,4-diamine was obtained as a mixture of the cis/trans isomers with chlorotrimethylsilane (718 µl) (white solid; 790 mg; m.p. 128-131° C.).

Example 64

N'-[2-(6-Fluoro-1H-indol-3-yl)-ethyl]-N,N-dimethyl-1-phenyl-cyclohexane-1,4-diamine dihydrochloride, nonpolar diastereomer 6-Fluorotryptamine (410 mg) and 4-dimethylamino-4-phenylcyclohexanone (545 mg) were dissolved in THF (18 ml) and 1,2-dichloroethane (6 ml) under argon, and acetic acid (138 mg) was added to the solution. After 15 minutes, sodium triacetoxyborohydride (690 mg) and THF (5 ml) were added. After 40 hours, the mixture was concentrated and the residue was taken up in 1M hydrochloric acid (20 ml) and extracted with ether (2×20 ml). The aqueous phase was rendered alkaline with 1M sodium hydroxide solution (30 ml) and extracted with ether (3×30 ml). A white solid (785 mg) precipitated between the phases and was separated off. The solid was a mixture of the two diastereomers, which also occurred when the ethereal phase was concentrated. The mixtures (985 mg) were together separated by column chromatography with methanol/conc. ammonia (500:1). The nonpolar diastereomer was obtained as a white solid (321 mg, m.p. 185-187° C.) and was dissolved in ethanol (20 ml), while heating, and 3.3N ethanolic HCl (0.79 ml) was added thereto. After an hour of stirring at RT, the white dihydrochloride of the nonpolar diamine of N'-[2-(6-fluoro-1H-indol-3-yl)-ethyl]-N,N-dimethyl-1-phenyl-cyclohexane-1,4-diamine was obtained (344 mg; m.p. 190-195° C.).

Example 65

N'-[2-(6-Fluoro-1H-indol-3-yl)-ethyl]-N,N-dimethyl-1-phenyl-cyclohexane-1,4-diamine dihydrochloride, polar diastereomer As described for example 64, 305 mg of the polar diastereomer of N'-[2-(6-fluoro-1H-indol-3-yl)-ethyl]-N,N-dimethyl-1-phenyl-cyclohexane-1,4-diamine were also obtained, from which the corresponding dihydrochloride was obtained in ethanol (20 ml) with 3.3N ethanolic HCl (0.73 ml) (270 mg; m.p. 208-211° C.).

Example 66

N'-[2-(1H-Indol-3-yl)-ethyl]-N,N,N'-trimethyl-1-phenyl-cyclohexane-1,4-diamine dihydrochloride, nonpolar diastereomer N-ω-Methyltryptamine ([2-(1H-indol-3-yl)ethyl]methylamine, 348 mg) was dissolved in dry 1,2-dichloroethane (10 ml) under argon. After addition of 4-dimethylamino-4-phenylcyclohexanone (435 mg) and glacial acetic acid (114 µl), a bulky precipitate formed. The suspension was stirred for two hours at RT before sodium triacetoxyborohydride (660 mg) was added. The reaction mixture was stirred for two days at RT and was concentrated for working up, the residue was dissolved in water (15 ml) and diethyl ether (20 ml) and the organic phase was separated off. The aqueous phase was extracted with diethyl ether (2×10 ml) and adjusted to pH 10 with 1M NaOH. A white solid precipitated out here and was filtered off with suction, washed and dried (174 mg, m.p. 208-210° C., nonpolar diastereomer). The aqueous phase was brought to pH 11 with 1M NaOH and extracted with ethyl acetate (4×25 ml). The extracts were combined, dried with $Na_2SO_4$ and concentrated in vacuo. The residue (469 mg) was separated by flash chromatography with methanol/triethylamine (99:1). The nonpolar diastereomer so obtained (172 mg) was dissolved while warm in 2-butanone/acetone (15 ml/15 ml), and the hydrochloride of N'-[2-(1H-indol-3-yl)-ethyl]-N,N,N'-trimethyl-1-phenyl-cyclohexane-1,4-diamine was precipitated as a white solid at RT with chlorotrimethylsilane (174 µl) (173 mg; m.p. 195-198° C.).

Example 67

N'-[2-(1H-Indol-3-yl)-ethyl]-N,N,N'-trimethyl-1-phenyl-cyclohexane-1,4-diamine dihydrochloride, polar diastereomer As described for example 66, 129 mg of the polar diastereomer of N'-[2-(1H-indol-3-yl)-ethyl]-N,N,N'-trimethyl-1-phenyl-cyclohexane-1,4-diamine were also obtained and were converted into the corresponding dihydrochloride while warm in 2-butanone/acetone (15 ml/3 ml) with chlorotrimethylsilane (121 µl) (white solid; 141 mg; m.p. 198-206° C.).

Example 68

N,N-Dimethyl-N'-[2-(7-methyl-1H-indol-3-yl)-ethyl]-1-phenyl-cyclohexane-1,4-diamine dihydrochloride, nonpolar diastereomer 7-Methyltryptamine (348 mg) and 4-dimethylamino-4-phenylcyclohexanone (435 mg) were dissolved in dry 1,2-dichloroethane (5 ml) and tetrahydrofuran (15 ml) with the exclusion of oxygen. Glacial acetic acid (2 mmol.) and sodium triacetoxyborohydride (600 mg) were added to this mixture and the mixture was stirred for 24 hours at RT. For working up, the mixture was concentrated, 1M HCl (20 ml) and diethyl ether (40 ml) were added to the batch, and the acid aqueous phase was extracted with diethyl ether (2×20 ml) and adjusted to pH 11 with 5M NaOH. The alkaline phase was diluted with water (10 ml) and extracted with ethyl acetate (3×20 ml). The combined extracts were dried with $Na_2SO_4$ and concentrated, and the crude product obtained was separated on silica gel with $EtOH/NH_3$ (500:1). The nonpolar diastereomer was obtained as a brown oil (321 mg), dissolved in 2-butanone (10 ml) and converted into the dihydrochloride with chlorotrimethylsilane (270 µl) (white solid; 420 mg; m.p. 189-191° C.).

Example 69

N,N-Dimethyl-N'-[2-(7-methyl-1H-indol-3-yl)-ethyl]-1-phenyl-cyclohexane-1,4-diamine dihydrochloride, polar diastereomer As described for example 68, 144 mg of the polar diastereomer were also obtained as a brown oil, dissolved in 2-butanone (5 ml) and converted into the corresponding hydrochloride with chlorotrimethylsilane (121 µl) (white solid; 146 mg; m.p. 244-246° C.).

Example 70

N'-[2-(5-Fluoro-1H-indol-3-yl)-ethyl]-N,N-dimethyl-1-phenyl-cyclohexane-1,4-diamine dihydrochloride, nonpolar diastereomer To a mixture of tetrahydrofuran (12 ml) and 1,2-dichloroethane (4 ml) there were added, under argon, first 2-(5-fluoro-1H-indol-3-yl)ethylamine (282 mg) and 4-dimethylamino-4-phenylcyclohexanone (343 mg), and acetic acid (0.09 ml) was added thereto. After 15 minutes, NaBH(OAc)$_3$ (474 mg) was added, and stirring was carried out for 40 hours at RT. The reaction mixture was concentrated, and the residue was taken up in 1M hydrochloric acid (20 ml) and extracted with ether (2×30 ml). A white precipitate (191 mg) separated out here and was separated off. The aqueous solution was then rendered alkaline with 1M NaOH (28 ml) and extracted with ether (2×30 ml) and ethyl acetate (2×30 ml). The combined organic extracts were dried over sodium sulfate and concentrated. The residue (468 mg) consisted of two products, just like the solid separated off previously. They were together (459 mg) purified by column chromatography with methanol/ammonia (500:1). The nonpolar diastereomer was obtained as a white solid (218 mg; m.p. 191-192° C.), was dissolved in ethanol (15 ml), with heating, and 3.3N ethanolic hydrochloric acid (0.47 ml, 1.56 mmol.) was added thereto. Because no solid had yet precipitated after 90 minutes, 2-butanone (5 ml) was added. Crystallisation of the hydrochloride then began after a short time (184 mg; m.p. 230-237° C.).

Example 71

N'-[2-(5-Fluoro-1H-indol-3-yl)-ethyl]-N,N-dimethyl-1-phenyl-cyclohexane-1,4-diamine dihydrochloride, polar diastereomer As described for example 70, the polar diastereomer (189 mg; m.p. 200-201° C.) was also obtained, 159 mg thereof were dissolved in ethanol (15 ml) and 2-butanone (5 ml) and converted into the dihydrochloride with 3.3N ethanolic hydrochloric acid (0.38 ml) (124 mg; m.p. 262-265° C.).

Example 72

N'-Acenaphthen-5-ylmethyl-N,N-dimethyl-1-phenyl-cyclohexane-1,4-diamine dihydrochloride, nonpolar diastereomer Acenaphthen-5-ylmethylamine (366 mg) and 4-dimethylamino-4-phenylcyclohexanone (434 mg) were dissolved in dry 1,2-dichloroethane (10 ml) with the exclusion of oxygen. Glacial acetic acid (2 mmol.) and sodium triacetoxyborohydride (600 mg) were added to this mixture and the mixture was stirred for 24 hours at RT. For working up, the mixture was concentrated and the residue was adjusted to pH 11 with 5M NaOH. The alkaline phase was diluted with water (10 ml) and extracted with ethyl acetate (3×20 ml). The combined organic phases were dried with $Na_2SO_4$ and concentrated. The crude product obtained was purified by chromatography with ethyl acetate/EtOH (1:1). The nonpolar diastereomer was obtained as a colorless oil (330 mg), dissolved in 2-butanone (10 ml) and converted with chlorotrimethylsilane (272 µl) into the corresponding dihydrochloride (white solid; 393 mg; m.p. 164-167° C.).

Example 73

N'-[2-(1H-Indol-3-yl)-1-methyl-ethyl]-N,N-dimethyl-1-thiophen-2-yl-cyclohexane-1,4-diamine dihydrochloride, nonpolar diastereomer DL-α-Methyltryptamine (N'-[2-(1H-indol-3-yl)-1-methylethyl]-N,N-dimethyl-1-thiophen-2-yl-cyclohexane-1,4-diamine, 348 mg) was dissolved in dry 1,2-dichloroethane (20 ml) under argon. After addition of 4-dimethylamino-4-thiophen-2-yl-cyclohexanone (447 mg) and glacial acetic acid (114 µl), a bulky precipitate formed. The suspension was stirred for one hour at RT. Sodium triacetoxyborohydride (660 mg) was then added and the reaction mixture was stirred for two days at RT. For working up, the mixture was diluted with 1,2-dichloroethane (10 ml) and water (15 ml), the organic phase was separated off, and the aqueous phase was again extracted with 1,2-dichloroethane (2×5 ml), rendered alkaline with 5M NaOH and extracted with ethyl acetate (4×15 ml). The combined organic phases were dried, concentrated and purified by flash chromatography (50 g silica gel 60, eluant: methanol/NEt$_3$ (99:1)). The nonpolar diastereomer (202 mg, m.p. 158-161° C.) was dissolved in 2-butanone (5 ml) and converted with chlorotrimethylsilane (202 µl) into the corresponding dihydrochloride (white solid, 207 mg; m.p. 162-165° C.).

Example 74

N'-[2-(1H-Indol-3-yl)-1-methyl-ethyl]-N,N-dimethyl-1-thiophen-2-yl-cyclohexane-1,4-diamine dihydrochloride, cis/trans mixture As described for example 73, a mixture of the diastereomers was also isolated (195 mg), dissolved in 2-butanone (4 ml) and converted with chlorotrimethylsilane (194 µl) into the corresponding dihydrochloride (white solid; 232 mg; polar/nonpolar=70:30).

Example 75

N'-[2-(7-Benzyloxy-1H-indol-3-yl)-ethyl]-N,N-dimethyl-1-phenyl-cyclohexane-1,4-diamine dihydrochloride, nonpolar diastereomer 7-Benzyloxytryptamine (200 mg) was dissolved in dry 1,2-dichloroethane (10 ml) and THF (10 ml) under argon. After addition of 4-dimethylamino-4-phenylcyclohexanone (180 mg) and glacial acetic acid (43 µl), the mixture was stirred for one hour at RT and then sodium triacetoxyborohydride (248 mg) was added thereto. The reaction mixture was stirred for three days at RT. For working up, the mixture was concentrated, the residue was dissolved in water (15 ml), 2M HCl (2 ml) and diethyl ether (20 ml), the organic phase was separated off, and the aqueous phase was washed with diethyl ether (2×15 ml), brought to pH 11 with 1M NaOH and extracted with ethyl acetate (4×10 ml). The combined ethyl acetate extracts were dried and concentrated, and the residue obtained (351 mg) was purified by flash chromatography (45 g silica gel 60, eluant: MeOH/NEt$_3$ (99:1)). The nonpolar diastereomer (188 mg) was dissolved in 2-butanone/acetone (6 ml/6 ml) while warm and converted with chlorotrimethylsilane (147 µl) into the corresponding dihydrochloride (white solid; 176 mg; m.p. 162-166° C.).

Example 76

N'-Cyclooctyl-N,N-dimethyl-1-thiophen-2-yl-cyclohexane-1,4-diamine dihydrochloride, nonpolar diastereomer 4-Dimethylamino-4-phenylcyclohexanone (447 mg, 2 mmol.) was dissolved in 1,2-dichloroethane (25 ml) under argon, and cyclooctylamine (254 mg) and acetic acid (120 mg) were added to the solution. The mixture was stirred for 15 minutes at RT and then sodium triacetoxyborohydride (600 mg) was added. After 48 hours at RT, the reaction mixture was concentrated in a rotary evaporator and the residue was taken up in 1M hydrochloric acid (20 ml) and washed with diethyl ether (2×30 ml). The aqueous solution was then rendered alkaline with 1M NaOH (28 ml) and extracted with Et$_2$O (3×30 ml). The combined organic extracts were dried over sodium sulfate and concentrated. The oily residue (586 mg) was purified by chromatography with methanol/ammonia (500:1). The nonpolar product was a colorless oil (280 mg) and, dissolved in 2-butanone (20 ml), was converted with 3.3N ethanolic hydrochloric acid (0.76 ml) into the corresponding dihydrochloride (white solid; 273 mg; m.p. 205-207° C.).

Example 77

N'-Adamantan-2-yl-N,N-dimethyl-1-thiophen-2-yl-cyclohexane-1,4-diamine dihydrochloride, nonpolar diastereomer 2-Adamantyl-amine (302 mg) and 4-dimethylamino-4-phenylcyclohexanone (446 mg) were dissolved under argon in a mixture of THF (15 ml) and 1,2-dichloroethane (5 ml). After 15 minutes, sodium triacetoxyborohydride (600 mg) was added to the mixture and stirring was carried out for 45 hours at room temperature. For working up, the mixture was concentrated, the residue was taken up in 1M HCl (20 ml) and diethyl ether (40 ml), the phases were separated and the aqueous phase was washed with diethyl ether (2×30 ml). The aqueous phase was rendered alkaline with 5M sodium hydroxide solution and extracted with diethyl ether (3×30 ml). After concentration of the combined organic extracts, the crude product obtained was separated by chromatography with methanol. The nonpolar diastereomer (286 mg) was dissolved in 2-butanone (15 ml) and converted with 3.3N ethanolic hydrochloric acid (0.606 ml) into the corresponding dihydrochloride (white solid; 300 mg; m.p. 266° C.).

Example 78

3-[2-(4-Dimethylamino-4-phenyl-cyclohexylamino)-ethyl]-1H-indol-5-ol dihydrochloride, nonpolar diastereomer Serotonin (405 mg) was dissolved in 1,2-dichloroethane/THF (5 ml/20 ml), and 4-dimethylamino-4-phenylcyclohexanone (500 mg), glacial acetic acid (131 µl) and red-hot sodium sulfate (2 g) were added thereto. After one hour's stirring at RT, sodium triacetoxyborohydride (759 mg) was added and stirring was carried out for a further two days. For working up, the mixture was concentrated, the residue was suspended in diethyl ether (15 ml), water (10 ml) and 2M HCl (1 ml), further diethyl ether (20 ml) was added, and the organic phase was coarsely separated off. The aqueous phase was first brought to pH 9 with 1M NaOH and extracted with ethyl acetate (3×5 ml), then adjusted to pH 11 and again extracted with ethyl acetate (5×10 ml). The organic extracts were dried and concentrated and the residue was purified by flash chromatography (eluant: MeOH/NEt$_3$ 99.5:0.5). 267 mg of the nonpolar diastereomer (m.p. 90-100° C.) were isolated and, dissolved in ethanol/2-butanone (3 ml/15 ml), were converted with 3.3M ethanolic HCl (642 µl) into the corresponding dihydrochloride (white solid; 304 mg; m.p. 215-217° C.).

Example 79

3-[2-(4-Dimethylamino-4-phenyl-cyclohexylamino)-ethyl]-1H-indol-5-ol dihydrochloride, polar diastereomer As described for example 78, 124 mg of the polar diastereomer (m.p. 185-187° C.) were also obtained and, dissolved in ethanol/2-butanone (6 ml/15 ml), were converted with 3.3M ethanolic HCl (298 µl) into the corresponding dihydrochloride (white solid; 123 mg; m.p. 230-233° C.).

Example 80

N'-[2-(5-Methoxy-1H-indol-3-yl)-ethyl]-N,N-dimethyl-1-phenyl-cyclohexane-1,4-diamine dihydrochloride, nonpolar diastereomer 6-Methoxytryptamine (495 mg) was dissolved until clear in dry 1,2-dichloroethane and THF (5 ml/15 ml) under argon. After addition of 4-dimethylamino-4-phenylcyclohexanone (565 mg) and glacial acetic acid (148 µl), stirring was carried out for two hours at RT, before sodium triacetoxyborohydride (858 mg) was added. The reaction mixture was stirred for two days at RT. For working up, water (15 ml) and 5.5M HCl (1.5 ml) were added to the reaction mixture. The phases were separated, the aqueous phase (pH 3) was washed with diethyl ether (3×10 ml) and then brought to pH 11 with 1M NaOH and extracted with ethyl acetate (5×15 ml). The combined extracts were dried with Na$_2$SO$_4$ and concentrated. The residue that remained (1.0 g; m.p. 129-153° C.) was purified by flash chromatography (eluant: MeOH/NEt$_3$ 99.25:0.75). The nonpolar diastereomer (550 mg, m.p. 164-169° C.) was separated off cleanly, dissolved in 2-butanone/acetone (15 ml/16 ml) while warm, and converted with chlorotrimethylsilane (533 µl) into the corresponding dihydrochloride (white solid; 633 mg; m.p. 165-175° C.).

Example 81

N'-[2-(5-Methoxy-1H-indol-3-yl)-ethyl]-N,N-dimethyl-1-phenyl-cyclohexane-1,4-diamine dihydrochloride, polar diastereomer As described for example 80, the polar diastereomer (320 mg; m.p. 136-140° C.) was also obtained, dissolved in 2-butanone/acetone (15 ml/3 ml) and converted with chlorotrimethylsilane (310 µl) into the corresponding dihydrochloride (white solid; 362 mg; m.p. 206-210° C.).

Example 82

N,N-Dimethyl-N'-[2-(5-methyl-1H-indol-3-yl)-ethyl]-1-phenyl-cyclohexane-1,4-diamine dihydrochloride, nonpolar diastereomer 5-Methyltryptamine (348 mg) and 4-dimethylamino-4-phenylcyclohexanone (435 mg) were dissolved in dry 1,2-dichloroethane (5 ml) and tetrahydrofuran (15 ml) with the exclusion of oxygen. Glacial acetic acid (114 µl) and sodium triacetoxyborohydride (600 mg) were added to this mixture and the mixture was stirred for 24 hours at RT. For working up, the mixture was concentrated, the residue was taken up in 1M HCl (20 ml) and diethyl ether (40 ml), the phases were separated, and the aqueous phase was extracted with diethyl ether (2×20 ml) and adjusted to pH 11 with 5M NaOH. The aqueous phase was diluted with water (10 ml) and extracted with ethyl acetate (3×20 ml). The combined organic extracts were dried with Na$_2$SO$_4$ and concentrated. The residue was purified by chromatography with MeOH/NH$_3$ (500:1). The nonpolar diastereomer (brown oil, 379 mg) was dissolved in 2-butanone (10 ml) and converted by addition of chlorotrimethylsilane (319 µl) into the corresponding dihydrochloride (white solid; 405 mg; m.p. 234-236° C.).

Example 83

N,N-Dimethyl-N'-[2-(5-methyl-1H-indol-3-yl)-ethyl]-1-phenyl-cyclohexane-1,4-diamine dihydrochloride, polar diastereomer As described for example 82, the polar diastereomer (266 mg) was also dissolved in 2-butanone (10 ml) and converted with Me$_3$SiCl (224 µl, 1.76 mmol.) into the corresponding dihydrochloride (white solid; 272 mg; m.p. 248-250° C.).

Example 84

Dimethyl-[1-phenyl-4-(1,3,4,9-tetrahydro-b-carbolin-2-yl)-cyclohexyl]-amine dihydrochloride 2,3,4,9-Tetrahydro-1H-β-carboline (345 mg) and 4-dimethylamino-4-phenylcyclohexanone (435 mg) were dissolved in a mixture of THF (10 ml) and 1,2-dichloroethane (15 ml) under argon, and acetic acid (120 mg, 2 mmol.) was added thereto. After 15 minutes, NaBH(OAc)$_3$ (600 mg) was added, stirring was carried out for 68 hours, the reaction mixture was concentrated and the residue was taken up in 1N hydrochloric acid (20 ml) and washed with ether (2×20 ml). The aqueous solution was rendered alkaline with 1M NaOH (30 ml) and extracted with ether (3×30 ml). After drying and concentration of the combined extracts, a semi-solid crude product was obtained which, after separation by column chromatography with methanol/NH$_3$ (500:3), yielded the nonpolar diastereomer (334 mg, m.p. 147-150° C.) which, dissolved with heating in 2-butanone (20 ml) and ethanol (10 ml), was converted with 3.3M ethanolic hydrochloric acid (0.8 ml) into the corresponding dihydrochloride (335 mg; 264-269° C.).

Example 85

N-(4-Dimethylamino-4-phenyl-cyclohexyl)-N-[2-(4-fluoro-phenyl)-ethyl]-acetamide hydrochloride, nonpolar diastereomer 4-(Fluorophenyl)ethylamine (1.15 g) and 4-dimethylamino-4-phenylcyclohexanone (1.8 g) were dissolved in dry 1,2-dichloroethane (20 ml) and tetrahydrofuran (60 ml) with the exclusion of oxygen. Glacial acetic acid (8.28 mmol.) and sodium triacetoxyborohydride (2.48 g, 11.59 mmol.) were added to this mixture and the mixture was stirred for 24 hours at RT. For working up, the mixture was concentrated, 1M HCl (20 ml) and diethyl ether (40 ml) were added to the batch, the phases were separated and the aqueous phase was extracted with diethyl ether (2×20 ml) and adjusted to pH 11 with 5N NaOH. The aqueous phase was diluted with water (10 ml) and extracted with ethyl acetate (3×20 ml). The combined organic extracts were dried over $Na_2SO_4$ and concentrated and the residue was purified by chromatography on silica gel with methanol. The nonpolar diastereomer (531 mg, 1.55 mmol.) was dissolved in anhydrous pyridine (10 ml), and acetic anhydride (1.59 g, 15.59 mmol.) was added thereto with stirring. After 24 hours, a few pieces of ice were added to the reaction mixture and the reaction mixture was concentrated as far as possible in a rotary evaporator. 1M NaOH (20 ml) was added to the residue. The aqueous phase was extracted with ethyl acetate (3×30 ml) and the combined organic extracts were dried with $Na_2SO_4$ and concentrated. The acetamide obtained (545 mg) was dissolved in 2-butanone (10 ml) and converted with chlorotrimethylsilane (0.270 ml) into the corresponding hydrochloride (white solid; 302 mg; m.p. 196-201° C.).

Example 86

2-(4-Dimethylamino-4-phenyl-cyclohexylamino)-3-(5-fluoro-1H-indol-3-yl)-propionic acid methyl ester dihydrochloride, nonpolar diastereomer 4-Dimethylamino-4-phenylcyclohexanone (935 mg), sodium sulfate (4 g) and glacial acetic acid (245 µl, 4.4 mmol.) were added under argon to rac-5-fluorotryptophan methyl ester (1,030 mg) in 1,2-dichloroethane (approx. 40 ml). After one hour's stirring at RT, sodium triacetoxyborohydride (1.4 g, 6.5 mmol.) was added. The mixture was stirred for three days at RT. For working up, the mixture was concentrated, the residue was taken up in ethyl acetate (40 ml) and 1N NaOH (35 ml), the phases were separated and the aqueous phase was extracted three times with ethyl acetate (10 ml each time). The combined extracts were dried and concentrated and the residue obtained (1.73 g) purified by flash chromatography (eluant: MeOH/EtOAc 1:3). The nonpolar diastereomer obtained (911 mg, m.p. 55-62° C.) was dissolved in 2-butanone/acetone (7 ml/1 ml) and converted with chlorotrimethylsilane (174 µl) into the corresponding dihydrochloride (beige solid; 135 mg; m.p. 172-182° C.).

Example 87

N-(4-Dimethylamino-4-phenyl-cyclohexyl)-N-(3-phenyl-propyl)-acetamide hydrochloride, nonpolar diastereomer 3-Phenylpropylamine (676 mg) and 4-dimethylamino-4-phenylcyclohexanone (1.086 g) were dissolved in dry 1,2-dichloroethane (5 ml) and tetrahydrofuran (15 ml) with the exclusion of oxygen. Glacial acetic acid (5 mmol.) and sodium triacetoxyborohydride (1.5 g, 7 mmol.) were added to this mixture and the mixture was stirred for 24 hours at RT. For working up, the mixture was concentrated, and 1M HCl (20 ml) and diethyl ether (40 ml) were added to the batch. The aqueous phase was washed with diethyl ether (2×20 ml), separated off, adjusted to pH 11 with 5N NaOH, diluted with water (10 ml) and extracted with ethyl acetate (3×20 ml). The combined organic extracts were dried with $Na_2SO_4$ and concentrated. The crude product obtained was purified by chromatography on silica gel with methanol. 761 mg of the nonpolar diastereomer were obtained.

453 mg were dissolved in anhydrous pyridine (10 ml), and acetic anhydride (1.374 g) was added with stirring. After 24 hours' stirring at RT, a few pieces of ice were added and the mixture was concentrated as far as possible in a rotary evaporator. 1N NaOH (20 ml) was added to the residue and the mixture was extracted with ethyl acetate (3×30 ml). The combined organic extracts were dried over $Na_2SO_4$ and concentrated. The acetamide obtained (528 mg) was dissolved in 2-butanone (10 ml) and converted with chlorotrimethylsilane (0.353 ml) into the corresponding hydrochloride (white solid; 282 mg; m.p. 206-211° C.).

Example 88

2-(4-Dimethylamino-4-phenyl-cyclohexylamino)-3-(6-fluoro-1H-indol-3-yl)-propionic acid methyl ester dihydrochloride, nonpolar diastereomer 4-Dimethylamino-4-phenylcyclohexanone (877 mg), sodium sulfate (2 g) and glacial acetic acid (230 µl, 4 mmol.) were added under argon to rac-6-fluorotryptophan methyl ester (952 mg) in 1,2-dichloroethane (approx. 30 ml). After one hour's stirring at RT, sodium triacetoxyborohydride (1.33 g, 6 mmol.) was added and the mixture was stirred for two days at RT. For working up, the mixture was concentrated, the residue was taken up in ethyl acetate (30 ml) and 1M NaOH (25 ml), the clear phases were separated in a separating funnel, the aqueous phase was extracted three times with ethyl acetate (10 ml each time) and the combined extracts were dried and concentrated by evaporation. The residue obtained (1.72 g) was purified by flash chromatography (eluant: MeOH/EtOAc 1:2, then MeOH/EtOAc 1:1 and MeOH/$NH_3$ 400:1). A portion (261 mg) of the nonpolar diastereomer (868 mg) was dissolved in 2-butanone (7 ml), and the corresponding dihydrochloride was precipitated with chlorotrimethylsilane (227 µl) (white solid; 224 mg; m.p. 164-169° C.).

Example 89

N-(4-Dimethylamino-4-phenyl-cyclohexyl)-2-(1H-indol-3-yl)-acetamide hydrochloride, polar diastereomer 4-Dimethylamino-4-phenylcyclohexanone (10 g) and hydroxylamine hydrochloride (4.8 g) were dissolved in absolute ethanol (120 ml), basic ion exchanger Amberlyst A 21 (30.7 g) was added to the solution, and stirring was carried out overnight at RT. The ion exchanger was filtered off and washed with ethanol (3×50 ml) on the frit. The ethanol was removed in vacuo and the residue was adjusted to pH 11 with 5M NaOH, diluted with water and extracted with ethyl acetate (4×30 ml). The combined extracts were dried with $Na_2SO_4$ and concentrated. 11 g of 4-dimethylamino-4-phenyl-cyclohexanone oxime were obtained.

4-Dimethylamino-4-phenyl-cyclohexanone oxime (11 g) was dissolved in methanol (200 ml) and diluted with 5M NaOH (200 ml). Devarda alloy (30 g) was added in portions to this mixture. The reaction temperature here was between 50-60° C. 15 minutes after completion of the addition, the mixture was diluted with water (150 ml), methanol was removed in vacuo, and the aqueous solution was extracted with ether (5×50 ml). The combined extracts were dried over Na$_2$SO$_4$ and concentrated. N,N-Dimethyl-1-phenylcyclohexane-1,4-diamine was obtained as a yellow oil (10.0 g).

N-Methylmorpholine (235 µl, 2.1 mmol.) and 2-chloro-4,6-dimethoxy-1,3,5-triazine (371 mg, 2.11 mmol.) were added to a solution of indol-3-ylacetic acid (257 mg) in abs. THF (10 ml). Stirring was then carried out for one hour at RT. The polar diastereomer of N,N-dimethyl-1-phenylcyclohexane-1,4-diamine (320 mg) was then added to the batch, and stirring was carried out for 12 hours at RT. For working up, the mixture was concentrated, the batch was adjusted to pH 11 with 5M NaOH, the phases were separated, and the aqueous phase was diluted with water (10 ml) and extracted with ethyl acetate (3×20 ml). The combined organic extracts were dried with Na$_2$SO$_4$ and concentrated. The amide obtained was purified by column chromatography with ethyl acetate/ethanol (1:1) and (120 mg) dissolved in 2-butanone (3 ml) and converted with chlorotrimethylsilane (61 µl) into the corresponding hydrochloride (white solid; 128 mg; 100-102° C.).

Example 90

2-(4-Dimethylamino-4-thiophen-2-yl-cyclohexylamino)-3-(1H-indol-3-yl)-propionic acid methyl ester dihydrochloride, nonpolar diastereomer The hydrochloride of L-tryptophan methyl ester (1.01 g) was stirred vigorously for 15 minutes with 1,2-dichloroethane (20 ml) and saturated NaHCO$_3$ solution (20 ml) and the aqueous phase was immediately extracted with 1,2-dichloroethane (2×20 ml). After drying with Na$_2$SO$_4$, the organic phase was concentrated to 40 ml, and 4-dimethylamino-4-phenylcyclohexanone (893 mg, 4 mmol.) was added thereto under argon. Glacial acetic acid (0.228 ml, 4 mmol.) and Na$_2$SO$_4$ (2 g) were added to the clear solution. After a reaction time of 15 minutes, NaBH(OAc)$_3$ (1.2 g) was added to the reaction mixture, and stirring was carried out for 4 days at room temperature. For working up, saturated NaHCO$_3$ solution (40 ml) was added and stirring was carried out for 15 minutes. The aqueous phase was extracted with dichloromethane (2×20 ml). The combined organic phases were dried and then concentrated, yielding a light-brown oil. Purification by column chromatography was carried out with ethyl acetate and methanol. The nonpolar diastereomer (918 mg; m.p. 108-112° C.) was dissolved in 2-butanone (15 ml) and converted with chlorotrimethylsilane (0.4 ml) into the corresponding dihydrochloride (white solid; 326 mg; m.p. 197-202° C.).

Example 91

N-(4-Dimethylamino-4-phenyl-cyclohexyl)-2-(5-methoxy-1H-indol-3-yl)-acetamide hydrochloride, nonpolar diastereomer The nonpolar diastereomer of N,N-dimethyl-1-phenyl-cyclohexane-1,4-diamine (387 mg) and 4-(4,6-dimethoxy-1,3,5-triazin-2-yl)-4-methyl-morpholinium chloride (267 mg, 2.0 mmol.) were added to a solution of (5-methoxy-1H-indol-3-yl)acetic acid (364 mg) in abs. methanol (20 ml). Stirring was then carried out for 24 hours at RT. For working up, the mixture was concentrated, the batch was diluted with water (10 ml) and the mixture was adjusted to pH 11 with 5M NaOH and extracted with ethyl acetate (3×20 ml). The combined organic extracts were dried over Na$_2$SO$_4$ and concentrated by evaporation. After column chromatography with MeOH, the nonpolar amide (154 mg; colorless oil) was dissolved in 2-butanone (5 ml) and converted with chlorotrimethylsilane (72 µl) into the corresponding hydrochloride (white solid; 168 mg; m.p. 143-145° C.).

Example 92

Measurement of the ORL1 Binding

The cyclohexane-1,4-diamine compounds of the general formula I were investigated in a receptor binding assay with $^3$H-nociceptinlorphanin FQ with membranes of recombinant CHO-ORL1 cells. This test system was conducted in accordance with the method described by Ardati et al. (Mol. Pharmacol., 51, 1997, p. 816-824). The concentration of $^3$H-nociceptin/orphanin FQ in these experiments was 0.5 nM. The binding assays were carried out with in each case 20 µg membrane protein per 200 µl batch in 50 mM Hepes, pH 7.4, 10 mM MgCl$_2$ and 1 mM EDTA. The binding to the ORL1 receptor was determined using in each case 1 mg WGA-SPA beads (Amersham-Pharmacia, Freiburg), by incubation of the batch for one hour at room temperature and subsequent measurement in a Trilux scintillation counter (Wallac, Finland). The affinity is stated as the K$_i$ value in µM.

| Example | ORL1 Ki/µM |
| --- | --- |
| 1 | 0.010 |
| 2 | 0.050 |
| 3 | 0.50 |
| 4 | 0.30 |
| 5 | 0.14 |
| 6 | 0.040 |
| 7 | 0.0030 |
| 8 | 0.28 |
| 9 | 0.34 |
| 10 | 0.12 |
| 11 | 0.38 |
| 12 | 0.25 |
| 13 | 0.22 |
| 14 | 0.10 |
| 15 | 0.093 |
| 16 | 0.066 |
| 17 | 0.010 |
| 18 | 0.027 |
| 19 | 0.0051 |
| 20 | 0.0054 |
| 21 | 0.0099 |
| 22 | 0.0060 |
| 23 | 0.250 |
| 24 | 0.0011 |
| 25 | 0.0020 |
| 26 | 0.210 |
| 27 | 0.017 |
| 28 | 0.039 |
| 29 | 0.19 |
| 30 | 0.49 |
| 31 | 0.051 |
| 32 | 0.0069 |
| 33 | 0.057 |
| 34 | 0.0084 |
| 35 | 0.45 |
| 36 | 0.54 |
| 37 | 0.0090 |
| 38 | 0.60 |
| 39 | 0.10 |
| 40 | 0.26 |
| 41 | 0.29 |
| 42 | 0.0013 |
| 43 | 0.042 |
| 44 | 0.066 |
| 45 | 0.63 |

-continued

| Example | ORL1 Ki/μM |
|---|---|
| 46 | 0.75 |
| 47 | 0.045 |
| 48 | 0.030 |
| 49 | 0.0026 |
| 50 | 0.039 |
| 51 | 0.0033 |
| 52 | 0.15 |
| 53 | 0.33 |
| 54 | 0.42 |
| 55 | 0.45 |
| 56 | 0.75 |
| 57 | 0.0015 |
| 58 | 0.25 |
| 59 | 0.18 |
| 60 | 0.0090 |
| 61 | 0.090 |
| 62 | 0.39 |
| 63 | 0.051 |
| 64 | 0.0036 |
| 65 | 0.17 |
| 66 | 0.0033 |
| 67 | 0.051 |
| 68 | 0.017 |
| 69 | 0.18 |
| 70 | 0.0004 |
| 71 | 0.18 |
| 72 | 0.019 |
| 73 | 0.0037 |
| 74 | 0.013 |
| 75 | 0.10 |
| 76 | 0.020 |
| 77 | 0.0063 |
| 78 | 0.0092 |
| 79 | 0.095 |
| 80 | 0.023 |
| 81 | 0.55 |
| 82 | 0.0015 |
| 83 | 0.095 |
| 84 | 0.043 |
| 85 | 0.002 |
| 86 | 0.004 |
| 87 | 0.023 |
| 89 | 0.014 |
| 90 | 0.025 |
| 90 | 0.004 |
| 91 | 0.006 |

Measurement of th ORL1 Binding

The cyclohexane-1,4-diamine compounds of the general formula I were investigated in a receptor binding assay with $^3$H-nociceptin/orphanin FQ with membranes of recombinant CHO-ORL1 cells. This test system was conducted in accordance with the method described by Ardati et al. (Mol. Pharmacol., 51, 1997,p. 816-824). The concentration of $^3$H-nociceptin/orphanin FQ in these experiments was 0.5 nM. The binding assays were carried out with in each case 20 μg membrane protein per 200 μl batch in 50 mM Hepes, pH 7.4, 10 mM MgCl$_2$ and 1 mM EDTA. The binding to the ORL1 receptor was determined using in each case 1 mg WGA-SPA beads (Amersham-Pharmacia, Freiburg), by incubation of the batch for one hour at room temperature and subsequent measurement in a Trilux scintillation counter (Wallac, Finland). The affinity is stated as the K$_i$ value.

Example 93

Analgesia Test in the Tail Flick Test in the Mouse

The mice were each placed individually into a test cage and the base of the tail was exposed to the focused heat ray of an electric lamp (tail-flick type 50/08/1.bc, Labtec, Dr. Hess). The intensity of the lamp was adjusted so that the time from switching on of the lamp to the sudden twitching away of the tail (latency of pain) in untreated mice was from 3 to 5 seconds. Before administration of the solutions comprising the compound according to the invention or of the particular comparison solutions, the mice were pre-tested twice in the course of five minutes and the mean of those measurements was calculated as the pre-test mean.

The solutions of the compound of the general formula I according to the invention and the comparison solutions were then administered intravenously. Pain measurement was carried out in each case 10, 20, 40 and 60 minutes following the intravenous administration. The analgesic activity was determined as the increase in the latency of pain (% of the maximum possible antinociceptive effect) according to the following formula:

$$[(T_1-T_0)/(T_2-T_0)]\times 100$$

where time $T_0$ is the latency before administration, time $T_1$ is the latency after administration of the active substance combination and time $T_2$ is the maximum exposure time (12 seconds).

The in-depth study of analgesic activity was carried out in the tail flick test in the mouse, as described above.

The tested compounds according to the invention exhibited analgesic activity. The results of selected tests are also compiled in the following table.

TABLE

| Example No. | Antinociceptive activity percentage relative to the control group* |
|---|---|
| 1 | 98 (10) |
| 3 | 40 (10) |
| 4 | 44 (10) |
| 7 | 100 (1) |
| 12 | 47 (10) |
| 27 | 49 (2.15) |
| 60 | 100 (1) |
| 85 | 91 (1) |
| 86 | 100 (1) |
| 88 | 100 (10) |
| 89 | 37 (1) |
| 90 | 94 (1) |
| 91 | 100 (1) |

*The dosage in mg/kg on intravenous administration is given in brackets in each case.

The studied compounds according to the invention exhibit good analgesic activity.

Example 94

Parenteral Solution of a Substituted Cyclohexane-1,4-diamine Compound According to the Invention 38 g of one of the substituted cyclohexane-1,4-diamine compounds according to the invention, here according to Example 91, are dissolved in 1 l of water for injection purposes at room temperature and the solution is then adjusted to isotonic conditions by addition of anhydrous glucose for injection purposes.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A substituted cyclohexane-1,4-diamine compound corresponding to formula I

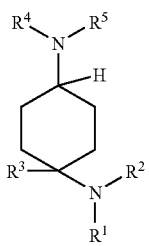

wherein
$R^1$ and $R^2$ are independently selected from the group consisting of H and $C_{1-8}$-alkyl saturated or unsaturated, branched or unbranched, mono- or polysubstituted or unsubstituted; wherein $R^1$ and $R^2$ are not both H; or
$R^3$ is selected from the group consisting of $C_{1-8}$-alkyl and $C_{3-8}$-cycloalkyl, each saturated or unsaturated, branched or unbranched, mono- or polysubstituted or unsubstituted; aryl and heteroaryl, each unsubstituted or mono- or polysubstituted and aryl, $C_{3-8}$-cycloalkyl and heteroaryl, each bound via a saturated or unsaturated, branched or unbranched, substituted or unsubstituted $C_{1-4}$-alkyl group and each unsubstituted or mono- or polysubstituted;
$R^4$ is selected from the group consisting of H; $C_{1-8}$-alkyl, which is saturated branched or unbranched, mono- or polysubstituted or unsubstituted; $C(X)R^7$, $C(X)NR^7R^8$, $C(X)OR^9$, $C(X)SR^9$, and $S(O_2)R^9$, where X=O or S;
$R^7$ is selected from the group consisting of H; $C_{1-8}$-alkyl and $C_{3-8}$-cycloalkyl, each saturated or unsaturated, branched or unbranched, mono- or polysubstituted or unsubstituted; aryl and heteroaryl, each unsubstituted or mono- or polysubstituted; and aryl, $C_{3-8}$-cycloalkyl and heteroaryl, each bound via a saturated or unsaturated, branched or unbranched, substituted or unsubstituted $C_{1-4}$-alkyl group and each unsubstituted or mono- or polysubstituted;
$R^8$ is selected from the group consisting of H; $C_{1-4}$-alkyl, saturated or unsaturated, branched or unbranched, mono- or polysubstituted or unsubstituted; or
$R^7$ and $R^8$ together form a ring and denote $CH_2CH_2OCH_2CH_2$, $CH_2CH_2NR^{10}CH_2CH_2$ or $(CH_2)_{3-6}$, where
$R^{10}$ is selected from the group consisting of H; $C_{1-8}$-alkyl and $C_{3-8}$-cycloalkyl, each saturated or unsaturated, branched or unbranched, mono- or polysubstituted or unsubstituted; aryl- and heteroaryl, each mono- or polysubstituted or unsubstituted; and aryl, $C_{3-8}$-cycloalkyl and heteroaryl, each bound via $C_{1-3}$-alkylene and each mono- or polysubstituted or unsubstituted; and
where $R^9$ is selected from the group consisting of $C_{1-8}$-alkyl and $C_{3-8}$-cycloalkyl, each case saturated or unsaturated, branched or unbranched, mono- or polysubstituted or unsubstituted; aryl and heteroaryl, each unsubstituted or mono- or polysubstituted; and aryl, $C_{3-8}$-cycloalkyl and heteroaryl, each bound via a saturated or unsaturated, branched or unbranched, substituted or unsubstituted $C_{1-4}$-alkyl group and each unsubstituted or mono- or polysubstituted; and
$R^5$ is selected from the group consisting of $C_{3-8}$-cycloalkyl, aryl and heteroaryl, each unsubstituted or mono- or polysubstituted; —$CHR^{11}R^{12}$; —$CHR^{11}$—$CH_2R^{12}$; —$CHR^{11}$—$CH_2$—$CH_2R^{12}$; —$CHR^{11}$—$CH_2$—$CH_2$—$CH_2R^{12}$; —$C(Y)R^{12}$; —$C(Y)$—$CH_2R^{12}$; —$C(Y)$—$CH_2$—$CH_2R^{12}$ and —$C(Y)$—$CH_2$—$CH_2$—$CH_2R^{12}$, where Y=O, S or $H_2$;
$R^{11}$ is selected from the group consisting of H; $C_{1-7}$-alkyl, saturated or unsaturated, branched or unbranched, mono- or polysubstituted or unsubstituted; and $C(O)O$—$C_{1-6}$-alkyl, saturated or unsaturated, branched or unbranched, mono- or polysubstituted or unsubstituted;
$R^{12}$ is selected from the group consisting of H; $C_{3-8}$-cycloalkyl, aryl and heteroaryl, each unsubstituted or mono- or polysubstituted; or
$R^4$ and $R^5$ together form a heterocyclic radical having between 3 and 8 atoms in the ring, which is saturated or unsaturated; mono- or polysubstituted or unsubstituted, and which heterocyclic radical may optionally be condensed with further rings, or
$R^4$ and $R^5$ together form a heterocyclic radical having between 5 and 7 atoms in the ring, which is saturated or unsaturated; mono- or polysubstituted or unsubstituted, and which heterocyclic radical may optionally be condensed with further rings and, in addition to the N attached to the cyclohexane, 0 to 1 further heteroatoms selected from the group consisting of N, S and O are in the ring,
wherein monosubstituted means replacement of hydrogen and polysubstituted means replacement of more than one hydrogen, with
for alkyl and cycloalkyl: F, Cl, Br, I, $NH_2$, SH or OH and in the case of $C_{3-8}$-cycloalkyl, also with $OC_{1-3}$-alkyl or $C_{1-3}$-alkyl, which may themselves be mono- or polysubstituted or unsubstituted; and
for aryl and heteroaryl: $R^{22}$, $OR^{22}$, halogen, $CF_3$, CN, $NO_2$, $NR^{23}R^{24}$, saturated $C_{1-6}$-alkyl, $C_{1-6}$-alkoxy, $C_{3-8}$-cycloalkoxy, $C_{3-8}$-cycloalkyl or $C_{2-6}$-alkylene; wherein
$R^{22}$ represents H; $C_{1-10}$-alkyl; aryl or heteroaryl; or an aryl or heteroaryl bonded via $C_{1-3}$-alkyl, saturated or unsaturated, or via a $C_{1-3}$-alkylene group, wherein the aryl and heteroaryl may not themselves be substituted by aryl or heteroaryl;
$R^{23}$ and $R^{24}$, which are identical or different, represent H; $C_{1-10}$-alkyl; aryl or heteroaryl; or an aryl or heteroaryl bonded via $C_{1-3}$-alkyl, saturated or unsaturated, or via a $C_{1-3}$-alkylene group, wherein the aryl and heteroaryl may not themselves be substituted by aryl or heteroaryl;
or $R^{23}$ and $R^{24}$ together represent $CH_2CH_2OCH_2CH_2$, $CH_2CH_2NR^{25}CH_2CH_2$ or $(CH_2)_{3-6}$; and $R^{25}$ represents H, $C_{1-10}$-alkyl; aryl or heteroaryl; or an aryl or heteroaryl bonded via $C_{1-3}$-alkyl, saturated or unsaturated, or via a $C_{1-3}$-alkylene group, wherein the aryl and heteroaryl may not themselves be substituted by aryl or heteroaryl,
provided that if $R^3$ is substituted or unsubstituted phenyl and at least one of $R^1$ or $R^2$ is H or $C_{1-8}$-alkyl, then $R^4$ is not alkyl and $R^4$ and $R^5$ do not together form a heterocyclic radical, or a solvate or salt thereof with a physiologically acceptable acid or base.

2. A compound according to claim 1, wherein said compound is in the form of a racemate.

3. A compound according to claim 1, wherein said compound is in the form of a pure stereoisomer.

4. A compound according to claim 3, wherein said stereoisomer is in the form of a pure enantiomer.

5. A compound according to claim 3, wherein said stereoisomer is in the form of a pure diastereomer.

6. A compound according to claim 1, wherein said compound is in the form of a mixture of stereoisomers in an arbitrary mixing ratio.

7. A compound according to claim 1, wherein said compound is in the form of a free base.

8. A compound according to claim 1, wherein said compound is in the form of a salt with a physiologically acceptable acid.

9. A compound according to claim 1, wherein said compound is in the form of a solvate.

10. A compound according to claim 1, wherein $R^3$ is selected from the group consisting of $C_{3-8}$-cycloalkyl, aryl and heteroaryl, each unsubstituted or mono- or polysubstituted; and aryl, $C_{3-8}$-cycloalkyl and heteroaryl, each bound via a saturated or unsaturated, unbranched, substituted or unsubstituted $C_{1-4}$-alkyl group and each unsubstituted or mono- or polysubstituted.

11. A compound according to claim 1, wherein $R^4$ is H.

12. A compound according to claim 1, wherein $R^4$ is selected from the group consisting of H, $C(X)R^7$, $C(X)NR^7R^8$, $C(X)OR^9$, $C(X)SR^9$ and $S(O_2)R^9$, where X=O or S.

13. A compound according to claim 1, wherein
$R^4$ and $R^5$ together form a heterocyclic radical having between 5 and 7 atoms in the ring, and, in addition to the N attached to the cyclohexane, 0 to 1 further heteroatoms selected from the group consisting of N, S and O are in the ring.

14. A compound according to claim 1, wherein
$R^4$ and $R^5$ together form a heterocyclic radical which is condensed with further rings which are either aromatic or heteroaromatic rings which may optionally be condensed with further rings which are either aromatic or heteroaromatic.

15. A compound according to claim 1, wherein $R^4$ and $R^5$ together form a heterocyclic radical which is condensed with one or two further rings.

16. A compound according to claim 1, wherein $R^4$ is either H or $C_{1-8}$-alkyl, which is saturated branched or unbranched, mono- or polysubstituted or unsubstituted.

17. A compound according to claim 1, wherein $R^5$ is selected from the group consisting of $C_{3-8}$-cycloalkyl, aryl and heteroaryl, each unsubstituted or mono- or polysubstituted.

18. A compound according to claim 1, wherein $R^5$ is selected from the group consisting of —$CHR^{11}R^{12}$, —$CHR^{11}$—$CH_2R^{12}$, —$CHR^{11}$—$CH_2$—$CH_2R^{12}$, —$CHR^{11}$—$CH_2$—$CH_2$—$CH_2R_{12}$, —$C(Y)R_{12}$, —$C(Y)$—$CH_2R^{12}$, —$C(Y)$—$CH_2$—$CH_2R^{12}$ and —$C(Y)$—$CH_2$—$CH_2$—$CH_2R^{12}$, where Y=O, S or $H_2$.

19. A compound according to claim 18, wherein $R^5$ is selected from the group consisting of —$CHR^{11}R^{12}$, —$CHR^{11}$—$CH_2R^{12}$, —$CHR^{11}$—$CH_2$—$CH_2R^{12}$, —$C(Y)R^{12}$, —$C(Y)$—$CH_2R^{12}$ and —$C(Y)$—$CH_2$—$CH_2R^{12}$, where Y=O or S.

20. A compound according to claim 18, wherein $R^5$ is selected from the group consisting of —$CHR^{11}R^{12}$, —$CHR^{11}$—$CH_2R^{12}$, —$CHR^{11}$—$CH_2$—$CH_2R^{12}$, —$C(Y)R^{12}$ and —$C(Y)$—$CH_2R^{12}$, where Y=O.

21. A compound according to claim 1, wherein said compound is
N'-benzyl-N,N-dimethyl-1-phenyl-cyclohexane-1,4-diamine hydrochloride, as a nonpolar diastereomer;
N'-benzyl-N,N-dimethyl-1-phenyl-cyclohexane-1,4-diamine hydrochloride, as a polar diastereomer;
1,N'-dibenzyl-N,N-dimethyl-cyclohexane-1,4-diamine hydrochloride, as a nonpolar diastereomer;
1,N'-dibenzyl-N,N-dimethyl-cyclohexane-1,4-diamine hydrochloride, as a polar diastereomer;
N-(4-benzyl-4-dimethylamino-cyclohexyl)-N-propyl-benzamide hydrochloride;
N,N-dimethyl-1-phenyl-N'-propyl-cyclohexane-1,4-diamine hydrochloride, as a nonpolar diastereomer;
N-(4-dimethylamino-4-phenyl-cyclohexyl)-N-propyl-benzamide hydrochloride, as a nonpolar diastereomer;
N-(4-dimethylamino-4-phenyl-cyclohexyl)-N-propyl-benzamide hydrochloride, as a polar diastereomer;
1,N'-dibenzyl-N,N,N'-trimethyl-cyclohexane-1,4-diamine hydrochloride, as a nonpolar diastereomer;
1,N'-dibenzyl-N,N,N'-trimethyl-cyclohexane-1,4-diamine hydrochloride, as a polar diastereomer;
N-(4-benzyl-4-dimethylamino-cyclohexyl)-N-methyl-benzamide hydrochloride, as a polar diastereomer;
N-(4-benzyl-4-dimethylamino-cyclohexyl)-N-ethyl-benzamide hydrochloride, as a polar diastereomer;
1-benzyl-N'-(1H-indol-3-ylmethyl)-N,N-dimethyl-cyclohexane-1,4-diamine dihydrochloride;
1-benzyl-N'-[2-(1H-indol-3-yl)-1-methyl-ethyl]-N,N-dimethyl-cyclohexane-1,4-diamine, as a cis/trans mixture;
1-benzyl-N'-indan-5-yl-N,N-dimethyl-cyclohexane-1,4-diamine hydrochloride;
1-benzyl-N'-indan-1-yl-N,N-dimethyl-cyclohexane-1,4-diamine dihydrochloride, as a cis/trans mixture;
N'-indan-1-yl-N,N-dimethyl-1-phenyl-cyclohexane-1,4-diamine;
N'-(1H-indol-5-yl)-N,N-dimethyl-1-phenyl-cyclohexane-1,4-diamine;
N'-(1H-indol-3-ylmethyl)-N,N-dimethyl-1-phenyl-cyclohexane-1,4-diamine, as a cis/trans mixture;
N'-(1H-indol-3-ylmethyl)-N,N-dimethyl-1-phenyl-cyclohexane-1,4-diamine, as a nonpolar diastereomer;
N'-[2-(1H-indol-3-yl)-ethyl]-N,N-dimethyl-1-phenyl-cyclohexane-1,4-diamine, as a nonpolar diastereomer;
N'-[2-(1H-indol-3-yl)-ethyl]-N,N-dimethyl-1-phenyl-cyclohexane-1,4-diamine, as a cis/trans mixture;
N'-indan-5-yl-N,N-dimethyl-1-phenyl-cyclohexane-1,4-diamine, as a nonpolar diastereomer;
N'-[2-(1H-indol-3-yl)-1-methyl-ethyl]-N,N-dimethyl-1-phenyl-cyclohexane-1,4-diamine, as a nonpolar diastereomer;
N'-[2-(1H-indol-3-yl)-1-methyl-ethyl]-N,N-dimethyl-1-phenyl-cyclohexane-1,4-diamine, as a cis/trans mixture;
N'-[2-(5-benzyloxy-1H-indol-3-yl)-ethyl]-N,N-dimethyl-1-phenyl-cyclohexane-1,4-diamine, as a cis/trans mixture;
N'-(9H-fluoren-1-yl)-N,N-dimethyl-1-phenyl-cyclohexane-1,4-diamine dihydrochloride;
N'-indan-2-yl-N,N-dimethyl-1-phenyl-cyclohexane-1,4-diamine dihydrochloride, as a cis/trans mixture;
N'-(9H-fluoren-9-yl)-N,N-dimethyl-1-phenyl-cyclohexane-1,4-diamine dihydrochloride, as a cis/trans mixture;

1-benzyl-N'-(9H-fluoren-9-yl)-N,N-dimethyl-cyclohexane-1,4-diamine;
1-benzyl-N'-(1H-indol-3-ylmethyl)-N,N-dimethyl-cyclohexane-1,4-diamine, as a cis/trans mixture;
N,N-dimethyl-N'-(1-methyl-1H-indol-3-ylmethyl)-1-phenyl-cyclohexane-1,4-diamine, as a cis/trans mixture;
N,N-dimethyl-N'-(1-methyl-1H-indol-3-ylmethyl)-1-phenyl-cyclohexane-1,4-diamine, as a polar diastereomer;
N'-(2-benzo[b]thiophen-3-yl-ethyl)-N,N-dimethyl-1-phenyl-cyclohexane-1,4-diamine dihydrochloride, as a cis/trans mixture;
N'-(2-benzo[b]thiophen-3-yl-ethyl)-1-benzyl-N,N-dimethylcyclohexane-1,4-diamine dihydrochloride, as a cis/trans mixture;
N'-acenaphthen-1-yl-N,N-dimethyl-1-phenyl-cyclohexane-1,4-diamine dihydrochloride, as a polar diastereomer;
N'-acenaphthen-1-yl-N,N-dimethyl-1-phenyl-cyclohexane-1,4-diamine dihydrochloride, as a nonpolar diastereomer;
N'-benzo[b]thiophen-5-yl-1-benzyl-N,N-dimethyl-cyclohexane-1,4-diamine dihydrochloride, as a nonpolar diastereomer;
N'-benzo[b]thiophen-5-yl-N,N-dimethyl-1-phenyl-cyclohexane-1,4-diamine hydrochloride, as a nonpolar diastereomer;
N'-benzothiazol-6-yl-N,N-dimethyl-1-phenyl-cyclohexane-1,4-diamine dihydrochloride, as a nonpolar diastereomer;
N'-benzo[1,2,5]thiadiazol-4-yl-N,N-dimethyl-1-phenyl-cyclohexane-1,4-diamine dihydrochloride, as a polar diastereomer;
N'-[2-(1H-indol-3-yl)-1-methyl-ethyl]-N,N-dimethyl-1-phenyl-cyclohexane-1,4-diamine dihydrochloride, as a nonpolar diastereomer;
N'-adamantan-2-yl-N,N-dimethyl-1-phenyl-cyclohexane-1,4-diamine dihydrochloride;
N'-(9-ethyl-9H-carbazol-3-yl)-N,N-dimethyl-1-phenyl-cyclohexane-1,4-diamine dihydrochloride, as a nonpolar diastereomer;
N'-(3H-benzotriazol-5-yl)-N,N-dimethyl-1-phenyl-cyclohexane-1,4-diamine hydrochloride, as a nonpolar diastereomer;
N'-(3H-benzotriazol-5-yl)-N,N-dimethyl-1-phenyl-cyclohexane-1,4-diamine hydrochloride, as a polar diastereomer;
N'-(9H-fluoren-9-yl)-N,N-dimethyl-1-thiophen-2-yl-cyclohexane-1,4-diamine dihydrochloride, as a cis/trans mixture;
N'-cyclooctyl-N,N-dimethyl-1-phenyl-cyclohexane-1,4-diamine dihydrochloride;
N'-(1H-indol-3-ylmethyl)-N,N-dimethyl-1-phenyl-cyclohexane-1,4-diamine dihydrochloride, as a nonpolar diastereomer;
N'-(1H-indol-3-ylmethyl)-N,N-dimethyl-1-phenyl-cyclohexane-1,4-diamine dihydrochloride, as a polar diastereomer;
N'-benzo[b]thiophen-3-ylmethyl-N,N-dimethyl-1-phenyl-cyclohexane-1,4-diamine dihydrochloride, as a nonpolar diastereomer;
N'-benzo[b]thiophen-3-ylmethyl-N,N-dimethyl-1-phenyl-cyclohexane-1,4-diamine dihydrochloride, as a polar diastereomer;
N'-anthracen-2-yl-N,N-dimethyl-1-phenyl-cyclohexane-1,4-diamine hydrochloride, as a nonpolar diastereomer;
N'-benzo[b]thiophen-3-ylmethyl-1-benzyl-N,N-dimethyl-cyclohexanae-1,4-diamine dihydrochloride, as a nonpolar diastereomer;
N'-benzo[b]thiophen-3-ylmethyl-1-benzyl-N,N-dimethyl-cyclohexane-1,4-diamine dihydrochloride, as a polar diastereomer;
N'-[2-(1H-indol-3-yl)-ethyl]-N,N-dimethyl-1-naphthalen-2-yl-cyclohexane-1,4-diamine dihydrochloride, as a nonpolar diastereomer;
N'-[2-(1H-indol-3-yl)-ethyl]-N,N-dimethyl-1-phenyl-cyclohexane-1,4-diamine dihydrochloride, as a nonpolar diastereomer;
N'-[2-(1H-indol-3-yl)-ethyl]-N,N-dimethyl-1-phenyl-cyclohexane-1,4-diamine dihydrochloride, as a polar diastereomer;
N'-[2-(1H-indol-3-yl)-1-methyl-ethyl]-N,N-dimethyl-1-phenyl-cyclohexane-1,4-diamine dihydrochloride, as a polar diastereomer;
Methyl 2-(4-dimethylamino-4-phenyl-cyclohexylamino)-3-(1H-indol-3-yl)-propionate dihydrochloride, as a nonpolar diastereomer;
Methyl 2-(4-dimethylamino-4-phenyl-cyclohexylamino)-3-(1H-indol-3-yl)-propionate dihydrochloride as a polar diastereomer;
N'-[2-(1H-indol-3-yl)-1-methyl-ethyl]-N,N,-dimethyl-1-naphthalen-2-yl-cyclohexane-1,4-diamine dihydrochloride, as a nonpolar diastereomer;
N'-benzo[1,3]dioxol-5-ylmethyl-N,N-dimethyl-1-phenyl-cyclohexane-1,4-diamine dihydrochloride, as a cis/trans mixture;
N'-[2-(6-fluoro-1H-indol-3-yl)-ethyl]-N,N-dimethyl-1-phenyl-cyclohexane-1,4-diamine dihydrochloride, as a nonpolar diastereomer;
N'[2-(6-fluoro-1H-indol-3-yl)-ethyl]-N,N-dimethyl-1-phenyl-cyclohexane-1,4-diamine dihydrochloride, as a polar diastereomer;
N'-[2-(1H-indol-3-yl)-ethyl]-N,N,N'-trimethyl-1-phenyl-cyclohexane-1,4-diamine dihydrochloride, as a nonpolar diastereomer;
N'-[2-(1H-indol-3-yl)-ethyl]-N,N,N'-trimethyl-1-phenyl-cyclohexane-1,4-diamine dihydrochloride, as a polar diastereomer;
N,N-dimethyl-N'-[2-(7-methyl-1H-indol-3-yl)-ethyl]-1-phenyl-cyclohexane-1,4-diamine dihydrochloride, as a nonpolar diastereomer;
N,N-dimethyl-N'-[2-(7-methyl-1H-indol-3-yl)-ethyl]-1-phenyl-cyclohexane-1,4-diamine dihydrochloride, as a polar diastereomer;
N'-[2-(5-fluoro-1H-indol-3-yl)-ethyl]-N,N-dimethyl-1-phenyl-cyclohexane-1,4-diamine dihydrochloride, as a nonpolar diastereomer;
N'-[2-(5-fluoro-1H-indol-3-yl)-ethyl]-N,N-dimethyl-1-phenyl-cyclohexane-1,4-diamine dihydrochloride, as a polar diastereomer;
N'-acenaphthen-5-ylmethyl-N,N-dimethyl-1-phenyl-cyclohexane-1,4-diamine dihydrochloride, as a nonpolar diastereomer;
N'-[2-(1H-indol-3-yl)-1-methyl-ethyl]-N,N-dimethyl-1-thiophen-2-yl-cyclohexane-1,4-diamine dihydrochloride, as a nonpolar diastereomer;
N'-[2-(1H-indol-3-yl)-1-methyl-ethyl]-N,N-dimethyl-1-thiophen-2-yl-cyclohexane-1,4-diamine dihydrochloride, as a cis/trans mixture;
N'-[2-(7-benzyloxy-1H-indol-3-yl)-ethyl]-N,N-dimethyl-1-phenyl-cyclohexane-1,4-diamine dihydrochloride, as a nonpolar diastereomer;

N'-cyclooctyl-N,N-dimethyl-1-thiophen-2-yl-cyclohexane-1,4-diamine dihydrochloride, as a nonpolar diastereomer;

N'-adamantan-2-yl-N,N-dimethyl-1-thiophen-2-yl-cyclohexane-1,4-diamine dihydrochloride, as a nonpolar diastereomer;

3-[2-(4-dimethylamino-4-phenyl-cyclohexylamino)-ethyl]-1H-indol-5-ol dihydrochloride, as a non polar diastereomer;

3-[2-(4-dimethylamino-4-phenyl-cyclohexylamino)-ethyl]-1H-indol-5-ol dihydrochloride, as a polar diastereomer;

N'-[2-(5-methoxy-1H-indol-3-yl)-ethyl]-N,N-dimethyl-1-phenyl-cyclohexane-1,4-diamine dihydrochloride, as a nonpolar diastereomer;

N'-[2-(5-methoxy-1H-indol-3-yl)-ethyl]-N,N-dimethyl-1-phenyl-cyclohexane-1,4-diamine dihydrochloride, as a polar diastereomer;

N,N-dimethyl-N'-[2-(5-methyl-1H-indol-3-yl)-ethyl]-1-phenyl-cyclohexane-1,4-diamine dihydrochloride, as a nonpolar diastereomer;

N,N-dimethyl-N'-[2-(5-methyl-1H-indol-3-yl)-ethyl]-1-phenyl-cyclohexane-1,4-diamine dihydrochloride, as a polar diastereomer; dimethyl-[1-phenyl-4-(1,3,4,9-tetrahydro-b-carbolin-2-yl)-cyclohexyl]-amine dihydrochloride;

N-(4-dimethylamino-4-phenyl-cyclohexyl)-N-[2-(4-fluoro-phenyl)-ethyl]-acetamide hydrochloride, as a nonpolar diastereomer; 2-(4-dimethylamino-4-phenyl-cyclohexylamino)-3-(5-fluoro-1H-indol-3-yl)-propionic acid methyl ester dihydrochloride, as a nonpolar diastereomer;

N-(4-dimethylamino-4-phenyl-cyclohexyl)-N-(3-phenyl-propyl)-acetamide hydrochloride, as a nonpolar diastereomer;

2-(4-dimethylamino-4-phenyl-cyclohexylamino)-3-(6-fluoro-1H-indol-3-yl)-propionic acid methyl ester dihydrochloride, as a nonpolar diastereomer;

N-(4-dimethylamino-4-phenyl-cyclohexyl)-2-(1H-indol-3-yl)-acetamide hydrochloride, as a polar diastereomer; 2-(4-dimethylamino-4-thiophen-2-yl-cyclohexylamino)-3-(1H-indol-3-yl)-propionic acid methyl ester dihydrochloride, as a nonpolar diastereomer; or N-(4-dimethylamino-4-phenyl-cyclohexyl)-2-(5-methoxy-1H-indol-3-yl)-acetamide hydrochloride, as a nonpolar diastereomer.

22. A pharmaceutical composition comprising as an active ingredient a pharmaceutically effective amount of a compound according to claim 1 and a pharmaceutically acceptable carrier or adjuvant.

23. A pharmaceutical composition according to claim 22, wherein said compound is in the form of a racemate.

24. A pharmaceutical composition according to claim 22, wherein said compound is in the form of a pure stereoisomer.

25. A pharmaceutical composition according to claim 22, wherein said compound is in the form of a mixture of stereoisomers in an arbitrary mixing ratio.

26. A pharmaceutical composition according to claim 22, wherein said compound is in the form of a free base.

27. A pharmaceutical composition according to claim 22, wherein said compound is in the form of a salt with a physiologically acceptable acid.

28. A pharmaceutical composition according to claim 22, wherein said compound is in the form of a solvate.

29. A pharmaceutical composition according to claim 22, wherein in the compound contained therein $R^3$ is selected from the group consisting of $C_{3-8}$-cycloalkyl, aryl and heteroaryl, each unsubstituted or mono- or polysubstituted; and aryl, $C_{3-8}$-cycloalkyl and heteroaryl, bound via a saturated or unsaturated, unbranched, substituted or unsubstituted $C_{1-4}$-alkyl group and each unsubstituted or mono- or polysubstituted.

30. A pharmaceutical composition according to claim 22, wherein in the compound contained therein $R^4$ is H.

31. A pharmaceutical composition according to claim 22, wherein in the compound contained therein $R^4$ is selected from the group consisting of H, $C(X)R^7$, $C(X)NR^7R^8$, $C(X)OR^9$, $C(X)SR^9$ and $S(O_2)R^9$, where X=O or S.

32. A pharmaceutical composition according to claim 22, wherein in the compound contained therein $R^4$ and $R^5$ together form a heterocyclic radical having between 5 and 7 atoms in the ring, and, in addition to the N attached to the cyclohexane, 0 to 1 further heteroatoms selected from the group consisting of N, S and O are in the ring.

33. A pharmaceutical composition according to claim 22, wherein in the compound contained therein $R^4$ and $R^5$ together form a heterocyclic radical which is condensed with further rings which are either aromatic or heteroaromatic rings which may optionally be condensed with further rings which are either aromatic or heteroaromatic.

34. A pharmaceutical composition according to claim 22, wherein in the compound contained therein $R^4$ and $R^5$ together form a heterocyclic radical which is condensed with one or two further rings.

35. A pharmaceutical composition according to claim 22, wherein in the compound contained therein $R^4$ is either H or $C_{1-8}$-alkyl, which is saturated or unsaturated, branched or unbranched, mono- or polysubstituted or unsubstituted.

36. A pharmaceutical composition according to claim 22, wherein in the compound contained therein $R^5$ is selected from the group consisting of $C_{3-8}$-cycloalkyl, aryl and heteroaryl, each unsubstituted or mono- or polysubstituted.

37. A pharmaceutical composition according to claim 22, wherein in the compound contained therein $R^5$ is selected from the group consisting of —$CHR^{11}R^{12}$, —$CHR^{11}$—$CH_2R^{12}$, —$CHR^{11}$—$CH_2$—$CH_2R^{12}$, —$CHR^{11}$—$CH_2$—$CH_2$—$CH_2R^{12}$, —$C(Y)R^{12}$, —$C(Y)$—$CH_2R^{12}$, —$C(Y)$—$CH_2$—$CH_2R^{12}$ and —$C(Y)$—$CH_2$—$CH_2$—$CH_2R^{12}$, where Y=O, S or $H_2$.

38. A pharmaceutical composition according to claim 22, comprising at least one compound according to claim 1 and either an opioid or an anaesthetic.

39. A pharmaceutical composition according to claim 38 wherein said pharmaceutical composition comprises an opioid and said opioid is morphine.

40. A pharmaceutical composition according to claim 38 wherein said pharmaceutical composition comprises an anaesthetic and said anaesthetic is either hexobarbital or halothane.

41. A method of alleviating pain in a patient, said method comprising administering to said patient a pharmaceutically effective amount of a compound according to claim 1.

42. A method according to claim 41, wherein said pain is acute, neuropathic or chronic pain.

43. A method according to claim 41, wherein said compound is in the form of a racemate.

44. A method according to claim 41, wherein said compound is in the form of a pure stereoisomer.

45. A method according to claim 41, wherein said compound is in the form of a mixture of stereoisomers in an arbitrary mixing ratio.

46. A method according to claim 41, wherein said compound is in the form of a free base.

47. A method according to claim 41, wherein said compound is in the form of a salt with a physiologically compatible acid.

48. A method according to claim 41, wherein said compound is in the form of a solvate.

49. A method according to claim 41, wherein if $R^3$ is substituted or unsubstituted phenyl and at least one of $R^1$ or $R^2$ is H or $C_{1-8}$-alkyl, then $R^4$ is not alkyl and $R^4$ and $R^5$ do not together form a heterocyclic radical.

50. A method according to claim 41, wherein in the compound used,
   $R^3$ is selected from the group consisting of $C_{3-8}$-cycloalkyl, aryl and heteroaryl, each unsubstituted or mono- or polysubstituted; and aryl, $C_{3-8}$-cycloalkyl and heteroaryl, each bound via a saturated or unsaturated, unbranched, substituted or unsubstituted $C_{1-4}$-alkyl group and each unsubstituted or mono- or polysubstituted.

51. A method according to claim 41, wherein in the compound used,
   $R^4$ and $R^5$ together form a heterocyclic radical having between 5 and 7 atoms in the ring, and in addition to the N atom attached to the cyclohexane 0 to 1 further heteroatoms selected from the group consisting of N, S or O are in the ring.

52. A method according to claim 41, wherein in the compound used,
   $R^4$ and $R^5$ together form a heterocyclic radical which is condensed with further rings which are either aromatic or heteroaromatic rings, which rings may optionally be condensed with further rings which are either aromatic or heteroaromatic.

53. A method according to claim 41, wherein in the compound used, $R^4$ and $R^5$ together form a heterocyclic radical which is condensed with one or two further rings.

54. A method according to claim 41, wherein in the compound used
   $R^4$ is either H or $C_{1-8}$-alkyl, which is saturated or unsaturated, branched or unbranched, mono- or polysubstituted or unsubstituted.

55. A method according to claim 41, wherein in the compound used
   $R^5$ is selected from the group consisting of $C_{3-8}$-cycloalkyl, aryl and heteroaryl, each unsubstituted or mono- or polysubstituted.

56. A method according to claim 41, wherein in the compound used
   $R^5$ is selected from the group consisting of —$CHR^{11}R^{12}$, —$CHR^{11}$—$CH_2R^{12}$, —$CHR^{11}$—$CH_2$—$CH_2R^{12}$, —$CHR^{11}$—$CH_2$—$CH_2$—$CH_2R^{12}$, —$C(Y)R^{12}$, —$C(Y)$—$CH_2R^{12}$, —$C(Y)$—$CH_2$—$CH_2R^{12}$ or —$C(Y)$—$CH_2$—$CH_2$—$CH_2R^{12}$, where Y=O, S or $H_2$.

57. A method according to claim 41, wherein said method comprises coadministering an opioid analgesic in combination with said compound of claim 1.

58. A method according to claim 41, wherein in the compound used, $R^4$ and $R^5$ together do not form a heterocyclic radical.

59. A compound according to claim 1, wherein $R^4$ and $R^5$ together do not form a heterocyclic radical.

60. A pharmaceutical composition according to claim 22, wherein in said compound, $R^4$ and $R^5$ together do not form a heterocyclic radical.

61. A process for the preparation of a compound corresponding to claim 1 comprising the steps of:
   a. reacting a cyclohexane-1,4-dione, protected with groups $S^1$ and $S^2$, corresponding to formula II with a cyanide, in the presence of a compound of the formula $HNR^{01}R^{02}$ to give a protected N-substituted 1-amino-4-oxo-cyclohexane-carbonitrile compound corresponding to formula III;

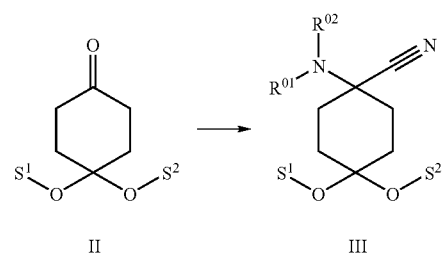

and optionally performing one or more of acylating, alkylating and sulfonating the compound corresponding to formula III, and optionally repeating the acylating, alkylating and sulfonating and where $R^{01}$ or $R^{02}$ or $R^{06}$=H protected with a protective group, once a protective group is split off an acylation, alkylation or sulfonation is optionally carried out and where $R^{01}$ or $R^{02}$ or $R^{06}$=H, once a protective group is introduced an acylation, alkylation or sulfonation is optionally carried out, b. reacting the aminonitrile corresponding to formula III with an organometallic reagent of the formula metal-$R^3$, so that a compound according to formula IVa is formed;

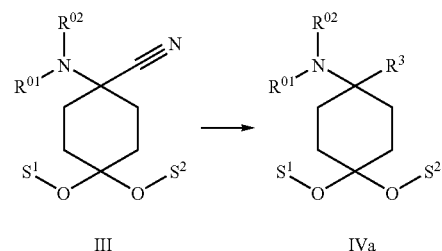

and optionally performing one or more of acylating, alkylating and sulfonating the compound corresponding to formula IVa, and optionally repeating the acylating, alkylating and sulfonating and where $R^{01}$ or $R^{02}$ or $R^{06}$=H protected with a protective group, once a protective group is split off an acylation, alkylation or sulfonation is optionally carried out and where $R^{01}$ or $R^{02}$ or $R^{06}$=H, once a protective group is introduced an acylation, alkylation or sulfonation is optionally carried out, c. splitting off the protective groups $S^1$ and $S^2$ from the compound corresponding to formula IVa, so that a 4-substituted 4-aminocyclohexanone compound according to formula IV is formed;

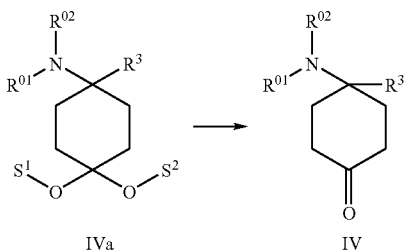

IVa → IV and optionally performing one or more of acylating, alkylating or sulfonating the compound corresponding to formula IV, and optionally repeating the acylating, akylating, and sulfonating and where $R^{01}$ or $R^{02}$ or $R^{06}$=H protected with a protective group, once a protective group is split off an acylation, alkylation or sulfonation is optionally carried out and where $R^{01}$ or $R^{02}$ or $R^{06}$=H, once a protective group is introduced an acylation, alkylation or sulfonation is optionally carried out, d. reductively aminating the 4-substituted 4-aminocyclohexanone compound corresponding to formula IVa with a compound of the formula $HNR^{04}R^{05}$, so that a cyclohexane-1,4-diamine compound corresponding to formula V is formed;

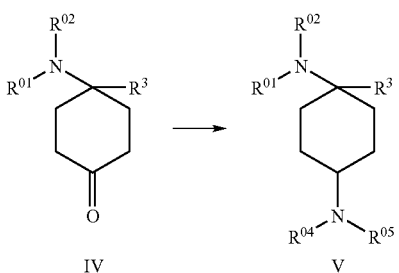

IV → V and optionally performing one or more of acylating, alkylating or sulfonating the compound corresponding to formula V, and optionally repeating the acylating, akylating, and sulfonating and where $R^{01}$ or $R^{02}$ or $R^{04}$ or $R^{05}$ or $R^{06}$=H protected with a protective group, once a protective group is split off an acylation, alkylation or sulfonation is optionally carried out and where $R^{01}$ or $R^{02}$ or $R^{04}$ or $R^{05}$ or $R^{06}$=H, once a protective group is introduced an acylation, alkylation or sulfonation is optionally carried out, until a compound according to formula I is formed, wherein $R^{01}$ and $R^{02}$ are independently selected from the group consisting of H; H provided with a protective group; $C_{1-8}$-alkyl and $C_{3-8}$-cycloalkyl, each saturated or unsaturated, branched or unbranched, mono- or polysubstituted or unsubstituted; and aryl-, and heteroaryl, each mono- or polysubstituted or unsubstituted; and aryl, $C_{3-8}$-cycloalkyl and heteroaryl, each bound via a $C_{1-3}$-alkylene and each mono- or polysubstituted or unsubstituted;

or the radicals $R^{01}$ and $R^{02}$ together form a ring and denote $CH_2CH_2OCH_2CH_2$, $CH_2CH_2NR^{06}CH_2CH_2$ or $(CH_2)_{3-6}$, where $R^{06}$ is selected from the group consisting of H; H provided with a protective group; $C_{1-8}$-alkyl and $C_{3-8}$-cycloalkyl, each saturated or unsaturated, branched or unbranched, mono- or polysubstituted or unsubstituted; and aryl-, and heteroaryl, each mono- or polysubstituted or unsubstituted; and aryl, $C_{3-8}$-cycloalkyl and heteroaryl, each bound via a $C_{1-3}$-alkylene and each mono- or polysubstituted or unsubstituted;

$R^{04}$ is selected from the group consisting of H, H provided with a protective group; and $C_{1-8}$-alkyl, which is saturated or unsaturated, branched or unbranched, mono- or polysubstituted or unsubstituted;

$R^{05}$ is selected from the group consisting of H, H provided with a protective group; and $C_{3-8}$-cycloalkyl, aryl and heteroaryl, each unsubstituted or mono- or polysubstituted; $—CHR^{11}R^{12}$, $—CHR^{11}—CH_2R^{12}$, $—CHR^{11}—CH_2—CH_2R^{12}$, $—CHR^{11}—CH_2—CH_2—CH_2R^{12}$, $—C(Y)R^{12}$, $—C(Y)—CH_2R^{12}$, $—C(Y)—CH_2—CH_2R^{12}$ and $—C(Y)—CH_2—CH_2—CH_2R^{12}$, where $Y=H_2$, where $R^{11}$ is either H or $C_{1-7}$-alkyl, which is saturated or unsaturated, branched or unbranched, mono- or polysubstituted or unsubstituted;

and where $R^{12}$ is selected from the group consisting of H; $C_{3-8}$-cycloalkyl, aryl and heteroaryl, each unsubstituted or mono- or polysubstituted, or $R^{04}$ and $R^{05}$ together form a heterocyclic radical having between 3 and 8 atoms in the ring, which is saturated or unsaturated; mono- or polysubstituted or unsubstituted, and $S^1$ and $S^2$ independently of one another are chosen from protective groups or together denote a protective group.

62. A process for the preparation of a compound corresponding to claim 1 comprising the steps of:

a. reductively aminating a cyclohexane-1,4-dione, protected with the groups $S^1$ and $S^2$, corresponding to formula II with a compound of the formula $HNR^{04}R^{05}$, so that a 4-aminocyclohexanone compound according to formula VI is formed;

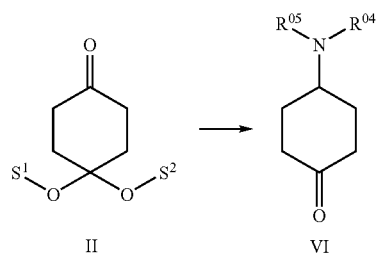

II → VI and optionally performing one or more of acylating, alkylating and sulfonating the compound corresponding to formula VI and optionally repeating the acylating, alkylating and sulfonating and where $R^{04}$ or $R^{05}$=H protected with a protective group, once a protective group is split off an acylation, alkylation or sulfonation is optionally carried out or in the case of a compound where $R^{04}$ or $R^{05}$=H, once a protective group is introduced an acylation, alkylation or sulfonation is optionally carried out, b. reacting the 4-aminocyclohexanone compound corresponding to formula VI with a cyanide in the presence of a compound of the formula $HNR^{O1}R^{O2}$ to give a cyclohexanone-nitrile compound corresponding to formula VII,

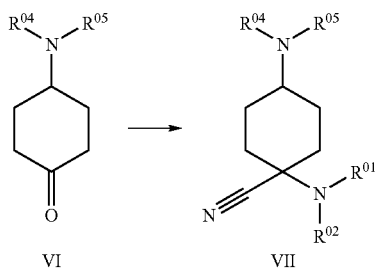

VI    VII and optionally performing one or more of acylating, alkylating and sulfonating and optionally repeating the acylating, alkylating and sulfonating and where $R^{O1}$ or $R^{O2}$ or $R^{O4}$ or $R^{O5}$ or $R^{O6}$=H protected with a protective group, once a protective group is split off an acylation, alkylation or sulfonation is optionally carried out or in the case of a compound where $R^{O1}$ or $R^{O2}$ or $R^{O4}$ or $R^{O5}$ or $R^{O6}$=H, once a protective group is introduced an acylation, alkylation or sulfonation is optionally carried out, c. reacting the cyclohexanone-nitrile compound of the formula VII with an organometallic reagent of the formula metal-$R^3$ and the protective groups $S^1$ and $S^2$ are split off, so that a cyclohexane-1,4-diamine compound according to formula V is formed,

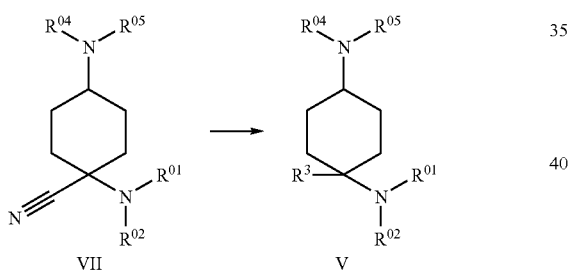

VII    V and optionally performing one or more of acylating, alkylating or sulfonating the compound corresponding to formula V and where $R^{O1}$ or $R^{O2}$ or $R^{O4}$ or $R^{O5}$ or $R^{O6}$=H protected with a protective group, once a protective group is split off an acylation, alkylation or sulfonation is optionally carried out and/or in the case of a compound where $R^{O1}$ or $R^{O2}$ or $R^{O4}$ or $R^{O5}$ or $R^{O6}$=H, once a protective group is introduced an acylation, alkylation or sulfonation is optionally carried out, until a compound according to formula I is formed, wherein $R^{O1}$ and $R^{O2}$ are independently selected from the group consisting of H; H provided with a protective group; $C_{1-8}$-alkyl and $C_{3-8}$-cycloalkyl, each saturated or unsaturated, branched or unbranched, mono- or polysubstituted or unsubstituted; aryl-, and heteroaryl, each mono- or polysubstituted or unsubstituted; and aryl, $C_{3-8}$-cycloalkyl and heteroaryl, each bound via a $C_{1-3}$-alkylene and each mono- or polysubstituted or unsubstituted;

or $R^{O1}$ and $R^{O2}$ together form a ring and denote $CH_2CH_2OCH_2CH_2$, $CH_2CH_2NR^{O6}CH_2CH_2$ or $(CH_2)_{3-6}$, where $R^{O6}$ is selected from the group consisting of H; H provided with a protective group; $C_{1-8}$-alkyl and $C_{3-8}$-cycloalkyl, each saturated or unsaturated, branched or unbranched, mono- or polysubstituted or unsubstituted; aryl-, and heteroaryl, each mono- or polysubstituted or unsubstituted; and aryl, $C_{3-8}$-cycloalkyl and heteroaryl, each bound via a $C_{1-3}$-alkylene and each mono- or polysubstituted or unsubstituted;

$R^{O4}$ is selected from the group consisting of H, H provided with a protective group; and $C_{1-8}$-alkyl, which is saturated or unsaturated, branched or unbranched, mono- or polysubstituted or unsubstituted;

$R^{O5}$ is selected from the group consisting of H, H provided with a protective group; $C_{3-8}$-cycloalkyl, aryl and heteroaryl, each unsubstituted or mono- or polysubstituted; $—CHR^{11}R^{12}$, $—CHR^{11}—CH_2R^{12}$, $—CHR^{11}—CH_2—CH_2R^{12}$, $—CHR^{11}—CH_2—CH_2—CH_2R^{12}$, $—C(Y)R^{12}$, $—C(Y)—CH_2R^{12}$, $—C(Y)—CH_2—CH_2R^{12}$ and $—C(Y)—CH_2—CH_2—CH_2R^{12}$, where $Y=H_2$, where $R^{11}$ is either H or $C_{1-7}$-alkyl, which is saturated or unsaturated, branched or unbranched, mono- or polysubstituted or unsubstituted;

where $R^{12}$ is selected from the group consisting of H; $C_{3-8}$-cycloalkyl, aryl and heteroaryl, each unsubstituted or mono- or polysubstituted, or $R^{O4}$ and $R^{O5}$ together form a heterocyclic radical having between 3 and 8 atoms in the ring, which is saturated or unsaturated; mono- or polysubstituted or unsubstituted, and $S^1$ and $S^2$ are independently selected from protective groups or together denote a protective group.

* * * * *